(12) United States Patent
Nasoff et al.

(10) Patent No.: US 12,049,511 B2
(45) Date of Patent: Jul. 30, 2024

(54) ENGINEERED CD46-SPECIFIC EFFECTOR CELLS AND USES THEREOF IN THE TREATMENT OF CANCER

(71) Applicant: FORTIS THERAPEUTICS, INC., La Jolla, CA (US)

(72) Inventors: Marc Nasoff, La Jolla, CA (US); Joshua Park, La Jolla, CA (US)

(73) Assignee: FORTIS THERAPEUTICS, INC., La Jolla, CA (US)

( * ) Notice: Subject to any disclaimer, the term of this patent is extended or adjusted under 35 U.S.C. 154(b) by 505 days.

(21) Appl. No.: 16/349,258

(22) PCT Filed: Nov. 10, 2017

(86) PCT No.: PCT/US2017/061153
§ 371 (c)(1),
(2) Date: May 10, 2019

(87) PCT Pub. No.: WO2018/089829
PCT Pub. Date: May 17, 2018

(65) Prior Publication Data
US 2019/0300620 A1  Oct. 3, 2019

Related U.S. Application Data

(60) Provisional application No. 62/420,508, filed on Nov. 10, 2016.

(51) Int. Cl.
| | |
|---|---|
| *C07K 16/28* | (2006.01) |
| *A61K 35/17* | (2015.01) |
| *A61K 38/17* | (2006.01) |
| *A61K 38/19* | (2006.01) |
| *A61K 38/20* | (2006.01) |
| *A61K 38/21* | (2006.01) |
| *A61K 39/00* | (2006.01) |
| *A61K 39/395* | (2006.01) |
| *A61P 35/00* | (2006.01) |
| *C07K 14/705* | (2006.01) |
| *C07K 14/725* | (2006.01) |
| *C07K 19/00* | (2006.01) |
| *C12N 5/0783* | (2010.01) |
| *C12N 15/63* | (2006.01) |
| *A61K 9/00* | (2006.01) |
| *A61K 31/675* | (2006.01) |
| *A61K 31/7076* | (2006.01) |
| *A61K 45/06* | (2006.01) |

(52) U.S. Cl.
CPC .......... *C07K 16/2896* (2013.01); *A61K 35/17* (2013.01); *A61K 38/177* (2013.01); *A61K 38/1774* (2013.01); *A61K 38/191* (2013.01); *A61K 38/20* (2013.01); *A61K 38/2013* (2013.01); *A61K 38/2046* (2013.01); *A61K 38/208* (2013.01); *A61K 38/2086* (2013.01); *A61K 38/217* (2013.01); *A61K 39/001112* (2018.08); *A61K 39/001129* (2018.08); *A61K 39/3955* (2013.01); *A61P 35/00* (2018.01); *C07K 14/7051* (2013.01); *C07K 14/70517* (2013.01); *C07K 14/70521* (2013.01); *C07K 14/70578* (2013.01); *C07K 19/00* (2013.01); *C12N 5/0638* (2013.01); *C12N 5/0646* (2013.01); *C12N 15/63* (2013.01); *A61K 9/0019* (2013.01); *A61K 9/0029* (2013.01); *A61K 31/675* (2013.01); *A61K 31/7076* (2013.01); *A61K 2039/5156* (2013.01); *A61K 2039/5158* (2013.01); *A61K 2039/54* (2013.01); *A61K 2039/545* (2013.01); *A61K 2039/572* (2013.01); *A61K 2039/884* (2018.08); *A61K 45/06* (2013.01); *C07K 2317/55* (2013.01); *C07K 2317/565* (2013.01); *C07K 2317/622* (2013.01); *C07K 2317/73* (2013.01); *C07K 2319/02* (2013.01); *C07K 2319/03* (2013.01); *C07K 2319/33* (2013.01); *C12N 2510/00* (2013.01)

(58) Field of Classification Search
CPC .......... C07K 16/2896; C07K 19/00; A61K 16/2896; A61K 35/17
See application file for complete search history.

(56) References Cited

U.S. PATENT DOCUMENTS

| | | | |
|---|---|---|---|
| 4,414,148 A | 11/1983 | Jansen et al. | |
| 4,439,196 A | 3/1984 | Higuchi | |
| 4,447,224 A | 5/1984 | DeCant, Jr. et al. | |
| 4,447,233 A | 5/1984 | Mayfield | |
| 4,469,863 A | 9/1984 | Ts'o et al. | |
| 4,474,814 A | 10/1984 | Fujita et al. | |

(Continued)

FOREIGN PATENT DOCUMENTS

| | | |
|---|---|---|
| EP | 0188256 A2 | 7/1986 |
| EP | 0404097 A2 | 12/1990 |

(Continued)

OTHER PUBLICATIONS

Kawalekar et al, Feb. 16, 2016. Immunity. 44: 380-390.*

(Continued)

*Primary Examiner* — Zachary C Howard
(74) *Attorney, Agent, or Firm* — DLA Piper LLP (US)

(57) ABSTRACT

Engineered effector cells, such as chimeric antigen receptors (CARs), are used for enhanced immunogenic response to specific antigen, such as CD46. Disclosed herein are compositions and methods of treatment a cancer overexpressing CD46, which comprises a pharmaceutical composition comprising an engineered effector cell.

19 Claims, 15 Drawing Sheets
Specification includes a Sequence Listing.

(56) References Cited

U.S. PATENT DOCUMENTS

| | | |
|---|---|---|
| 4,475,196 A | 10/1984 | La Zor |
| 4,486,194 A | 12/1984 | Ferrara |
| 4,487,603 A | 12/1984 | Harris |
| 4,522,811 A | 6/1985 | Eppstein et al. |
| 4,542,225 A | 9/1985 | Blattler et al. |
| 4,545,985 A | 10/1985 | Pastan et al. |
| 4,569,789 A | 2/1986 | Blattler et al. |
| 4,589,071 A | 5/1986 | Yamamuro et al. |
| 4,596,556 A | 6/1986 | Morrow et al. |
| 4,618,492 A | 10/1986 | Blattler et al. |
| 4,625,014 A | 11/1986 | Senter et al. |
| 4,659,839 A | 4/1987 | Nicolotti et al. |
| 4,671,958 A | 6/1987 | Rodwell et al. |
| 4,680,338 A | 7/1987 | Sundoro |
| 4,694,778 A | 9/1987 | Learn et al. |
| 4,699,784 A | 10/1987 | Shih et al. |
| 4,790,824 A | 12/1988 | Morrow et al. |
| 4,816,567 A | 3/1989 | Cabilly et al. |
| 4,866,132 A | 9/1989 | Obligin et al. |
| 4,894,443 A | 1/1990 | Greenfield et al. |
| 4,921,963 A | 5/1990 | Skov et al. |
| 4,941,880 A | 7/1990 | Burns |
| 4,956,778 A | 9/1990 | Naito |
| 4,957,735 A | 9/1990 | Huang |
| 4,975,369 A | 12/1990 | Beavers et al. |
| 5,034,506 A | 7/1991 | Summerton et al. |
| 5,064,413 A | 11/1991 | McKinnon et al. |
| 5,064,849 A | 11/1991 | Suzuki et al. |
| 5,075,431 A | 12/1991 | Shively et al. |
| 5,081,235 A | 1/1992 | Shively et al. |
| 5,091,513 A | 2/1992 | Huston et al. |
| 5,132,405 A | 7/1992 | Huston et al. |
| 5,169,939 A | 12/1992 | Gefter et al. |
| 5,202,238 A | 4/1993 | Fell, Jr. et al. |
| 5,204,244 A | 4/1993 | Fell et al. |
| 5,216,141 A | 6/1993 | Benner |
| 5,223,409 A | 6/1993 | Ladner et al. |
| 5,231,026 A | 7/1993 | Chang |
| 5,235,033 A | 8/1993 | Summerton et al. |
| 5,256,334 A | 10/1993 | Smid et al. |
| 5,264,586 A | 11/1993 | Nicolaou et al. |
| 5,292,867 A | 3/1994 | Chang |
| 5,312,335 A | 5/1994 | McKinnon et al. |
| 5,346,981 A | 9/1994 | Sarpeshkar et al. |
| 5,354,847 A | 10/1994 | Liu et al. |
| 5,374,548 A | 12/1994 | Caras |
| 5,383,851 A | 1/1995 | McKinnon, Jr. et al. |
| 5,386,023 A | 1/1995 | Sanghvi et al. |
| 5,399,163 A | 3/1995 | Peterson et al. |
| 5,399,331 A | 3/1995 | Loughrey et al. |
| 5,403,484 A | 4/1995 | Ladner et al. |
| 5,416,016 A | 5/1995 | Low et al. |
| 5,427,908 A | 6/1995 | Dower et al. |
| 5,428,156 A | 6/1995 | Mease et al. |
| 5,472,693 A | 12/1995 | Gourlie et al. |
| 5,482,856 A | 1/1996 | Fell, Jr. et al. |
| 5,491,088 A | 2/1996 | Hellstrom et al. |
| 5,500,362 A | 3/1996 | Robinson et al. |
| 5,502,167 A | 3/1996 | Waldmann et al. |
| 5,545,806 A | 8/1996 | Lonberg et al. |
| 5,545,807 A | 8/1996 | Surani et al. |
| 5,569,825 A | 10/1996 | Lonberg et al. |
| 5,571,698 A | 11/1996 | Ladner et al. |
| 5,580,717 A | 12/1996 | Dower et al. |
| 5,602,240 A | 2/1997 | De Mesmaeker et al. |
| 5,625,126 A | 4/1997 | Lonberg et al. |
| 5,633,425 A | 5/1997 | Lonberg et al. |
| 5,637,684 A | 6/1997 | Cook et al. |
| 5,644,048 A | 7/1997 | Yau |
| 5,661,016 A | 8/1997 | Lonberg et al. |
| 5,700,825 A | 12/1997 | Hofer et al. |
| 5,733,743 A | 3/1998 | Johnson et al. |
| 5,770,429 A | 6/1998 | Lonberg et al. |
| 5,789,650 A | 8/1998 | Lonberg et al. |
| 5,814,318 A | 9/1998 | Lonberg et al. |
| 5,831,012 A | 11/1998 | Nilsson et al. |
| 5,849,738 A | 12/1998 | Lee et al. |
| 5,872,107 A | 2/1999 | Schinazi et al. |
| 5,874,299 A | 2/1999 | Lonberg et al. |
| 5,877,397 A | 3/1999 | Lonberg et al. |
| 5,885,793 A | 3/1999 | Griffiths et al. |
| 5,939,045 A | 8/1999 | Suzuki et al. |
| 5,939,598 A | 8/1999 | Kucherlapati et al. |
| 5,945,439 A | 8/1999 | Richter et al. |
| 5,969,108 A | 10/1999 | McCafferty et al. |
| 6,001,329 A | 12/1999 | Buchsbaum et al. |
| 6,004,533 A | 12/1999 | Collins et al. |
| 6,010,681 A | 1/2000 | Margerum et al. |
| 6,010,682 A | 1/2000 | Unger et al. |
| 6,015,897 A | 1/2000 | Theodore et al. |
| 6,017,522 A | 1/2000 | Butterfield et al. |
| 6,022,522 A | 2/2000 | Sweet et al. |
| 6,022,523 A | 2/2000 | DeGrado et al. |
| 6,022,966 A | 2/2000 | Gustavson et al. |
| 6,028,066 A | 2/2000 | Unger |
| 6,030,840 A | 2/2000 | Mullinax et al. |
| 6,040,498 A | 3/2000 | Stomp et al. |
| 6,045,775 A | 4/2000 | Ericcson et al. |
| 6,045,821 A | 4/2000 | Garrity et al. |
| 6,048,979 A | 4/2000 | Vasilevskis et al. |
| 6,051,207 A | 4/2000 | Klaveness et al. |
| 6,056,939 A | 5/2000 | Desreux et al. |
| 6,060,040 A | 5/2000 | Tournier et al. |
| 6,071,490 A | 6/2000 | Griffiths et al. |
| 6,071,494 A | 6/2000 | Unger |
| 6,075,010 A | 6/2000 | Theodore et al. |
| 6,075,181 A | 6/2000 | Kucherlapati et al. |
| 6,077,499 A | 6/2000 | Griffiths et al. |
| 6,088,613 A | 7/2000 | Unger |
| 6,090,408 A | 7/2000 | Li et al. |
| 6,090,800 A | 7/2000 | Unger et al. |
| 6,093,382 A | 7/2000 | Wedeking et al. |
| 6,096,290 A | 8/2000 | Collins et al. |
| 6,106,866 A | 8/2000 | Ranney |
| 6,114,598 A | 9/2000 | Kucherlapati et al. |
| 6,117,412 A | 9/2000 | Klaveness et al. |
| 6,120,751 A | 9/2000 | Unger |
| 6,120,768 A | 9/2000 | Griffiths et al. |
| 6,123,921 A | 9/2000 | Meade et al. |
| 6,123,923 A | 9/2000 | Unger et al. |
| 6,132,764 A | 10/2000 | Li et al. |
| 6,139,819 A | 10/2000 | Unger et al. |
| 6,143,274 A | 11/2000 | Tweedle et al. |
| 6,143,276 A | 11/2000 | Unger |
| 6,149,890 A | 11/2000 | Uggeri et al. |
| 6,150,584 A | 11/2000 | Kucherlapati et al. |
| 6,153,775 A | 11/2000 | Schroder et al. |
| 6,159,445 A | 12/2000 | Klaveness et al. |
| 6,162,963 A | 12/2000 | Kucherlapati et al. |
| 6,172,197 B1 | 1/2001 | McCafferty et al. |
| 6,177,562 B1 | 1/2001 | Uggeri et al. |
| 6,183,721 B1 | 2/2001 | Albert et al. |
| 6,187,285 B1 | 2/2001 | Meyer et al. |
| 6,190,923 B1 | 2/2001 | Johnson |
| 6,232,068 B1 | 5/2001 | Linsley et al. |
| 6,469,779 B2 | 10/2002 | Baer et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,642,051 B1 | 11/2003 | Lynch et al. |
| 6,669,936 B2 | 12/2003 | Kingsman et al. |
| 6,670,188 B1 | 12/2003 | Vogels et al. |
| 6,815,184 B2 | 11/2004 | Stomp et al. |
| 6,818,749 B1 | 11/2004 | Kashmiri et al. |
| 7,378,504 B2 | 5/2008 | Graziano et al. |
| 7,528,126 B2 | 5/2009 | Howard et al. |
| 8,843,320 B2 | 9/2014 | Shaughnessy et al. |
| 8,865,873 B2 | 10/2014 | Liu et al. |
| 9,567,402 B2 | 2/2017 | Liu |
| 9,593,162 B2 | 3/2017 | Liu et al. |
| 10,400,045 B2 | 9/2019 | Liu |
| 10,479,839 B2 | 11/2019 | Liu et al. |

(56) References Cited

U.S. PATENT DOCUMENTS

| | | |
|---|---|---|
| 11,208,493 B2 | 12/2021 | Liu |
| 2003/0108966 A1 | 6/2003 | Mather |
| 2005/0186214 A1 | 8/2005 | Liu et al. |
| 2007/0128202 A1 | 6/2007 | Mather |
| 2010/0233165 A1 | 9/2010 | Liu et al. |
| 2011/0033378 A1 | 2/2011 | Dimasi et al. |
| 2012/0015906 A1 | 1/2012 | Shaughnessy, Jr. et al. |
| 2014/0205593 A1 | 7/2014 | Huang et al. |
| 2014/0271685 A1 | 9/2014 | Liu et al. |
| 2015/0071937 A1 | 3/2015 | Liu et al. |
| 2015/0368352 A1 | 12/2015 | Liu |
| 2016/0032008 A1 | 2/2016 | Zeng et al. |
| 2016/0361360 A1* | 12/2016 | Chang ............... A61P 37/06 |
| 2017/0233488 A1 | 8/2017 | Liu et al. |
| 2017/0240643 A1 | 8/2017 | Liu |
| 2017/0362330 A1 | 12/2017 | Liu et al. |
| 2018/0280532 A1 | 10/2018 | Goldenberg |
| 2020/0040094 A1 | 2/2020 | Liu |
| 2020/0199245 A1 | 6/2020 | Liu et al. |
| 2020/0255537 A1 | 8/2020 | Liu et al. |

FOREIGN PATENT DOCUMENTS

| | | |
|---|---|---|
| EP | 1184458 A1 | 3/2002 |
| JP | 2005511525 A | 4/2005 |
| JP | 2017513709 A | 6/2017 |
| WO | WO-9100996 A1 | 1/1991 |
| WO | WO-9203918 A1 | 3/1992 |
| WO | WO-9311161 A1 | 6/1993 |
| WO | WO-9312227 A1 | 6/1993 |
| WO | WO-9411026 A2 | 5/1994 |
| WO | WO-9413804 A1 | 6/1994 |
| WO | WO-9425585 A1 | 11/1994 |
| WO | WO-9515335 A2 | 6/1995 |
| WO | WO-9617958 A1 | 6/1996 |
| WO | WO-9713852 A1 | 4/1997 |
| WO | WO-9824884 A1 | 6/1998 |
| WO | WO-9945962 A1 | 9/1999 |
| WO | WO-9955720 A1 | 11/1999 |
| WO | WO-0114424 A2 | 3/2001 |
| WO | WO-0243478 A2 | 6/2002 |
| WO | WO-03032814 A2 | 4/2003 |
| WO | WO-2005062977 A2 | 7/2005 |
| WO | WO-2007059782 A1 | 5/2007 |
| WO | WO-2009039192 A2 | 3/2009 |
| WO | WO-2012031273 A2 | 3/2012 |
| WO | WO-2015105995 A2 | 7/2015 |
| WO | WO-2016019300 A1 | 2/2016 |
| WO | WO-2016040683 A1 | 3/2016 |
| WO | WO-2016042461 A1 | 3/2016 |
| WO | WO-2016100985 A2 | 6/2016 |
| WO | WO-2018089807 A2 | 5/2018 |
| WO | WO-2018089829 A1 | 5/2018 |

OTHER PUBLICATIONS

Benjamini et al, 1991. Immunology: A Short Course, 2nd edition, p. 40 only.*
Ferrara et al (2015. mAbs. 7(1): 32-41).*
He et al. Targeting Prostate Cancer Cells In Vivo Using a Rapidly Internalizing Novel Human Single-Chain Antibody Fragment. J Nucl Med 51(3):427-432 (2010).
Le Friec et al. The CD46-Jagged1 interaction is critical for human TH1 immunity. Nat Immunol 13(12):1213-1221 (2012).
Altschul et al. Basic Local Alignment Search Tool. J. Mol. Biol. 215: 403-410 (1990).
Altschul, et al. Gapped BLAST and PSI-BLAST: a new generation of protein database search programs. Nucleic Acids Res 25:3389-3402 (1997).
Barbas et al. Recognition of DNA by Synthetic Antibodies. J Am. Chem. Soc., 116:2161-2162 (1994).
Beaucage et al. Deoxynucleoside phosphoramidites—A new class of key intermediates for deoxypolynucleotide synthesis. Tetra. Lett. 22:1859-1862 (1981).
Becerril et al. Toward selection of internalizing antibodies from phage libraries. Biochem. Biophys. Res. Commun. 255:386-393 (1999).
Beiboer, Sigrid H. et al. Guided Selection of a Pan Carcinoma Specific Antibody Reveals Similar Binding Characteristics yet Structural Divergence Between the Original Murine Antibody and its Human Equivalent. J. Mol. Biol. 296:833-849 (2000).
Birkle et al. Role of tumor-associated gangliosides in cancer progression. Biochimie (Paris) 85(3-4):455-463 (2003).
Bonner et al. Laser capture microdissection: molecular analysis of tissue. Science 278:1481-1483 (1997).
Boulianne et al. Production of functional chimaeric mouse/human antibody. Nature 312:643 (1984).
Brown et al. Chemical synthesis and cloning of a tyrosine tRNA gene. Methods Enzymol. 68:109-51 (1979).
Buchner et al.: A method for increasing the yield of properly folded recombinant fusion proteins: single-chain immunotoxins from renaturation of bacterial inclusion bodies. Anal. Biochem. 205(2):263-270 (1992).
Cai et al. Anti-melanoma antibodies from melanoma patients immunized with genetically modified autologous tumor cells: selection of specific antibodies from single-chain Fv fusion phage libraries. PNAS USA 92:6537-6541 (1995).
Caron et al., Engineered humanized dimeric forms of IgG are more effective antibodies. J. Exp Med. 176:1191-1195 (1992).
Chaudhary et al. A proper amino terminus of diphtheria toxin is important for cytotoxicity. Bioch. Biophys. Res. Comm. 180:545-551 (1991).
Chothia et al. The predicted structure of immunoglobulin D1.3 and its comparison with the crystal structure. Science 233:755-8 (1986).
Clackson et al. A hot spot of binding energy in a hormone-receptor interface. Science 267:383-386 (1995).
Clynes et al. Inhibitory Fc receptors modulate in vivo cytotoxicity against tumour targets. Nat Med. 6(4):443-6. (Apr. 2000).
Commisso et al. Macropinocytosis of protein is an amino acid supply route in Ras-transformed cells. Nature 497:633-637 (2013).
Conrad et al. Compartment-specific accumulation of recombinant immunoglobulins in plant cells: an essential tool for antibody production and immunomodulation of physiological functions and pathogen activity. Plant Mal. Biol. 38:101-109 (1998).
Covell et al. Linking tumor cell cytotoxicity to mechanism of drug action: an integrated analysis of gene expression, small-molecule screening and structural databases. Proteins 59(3):403-433 (2005).
Cramer et al. Transgenic plants for therapeutic proteins: linking upstream and downstream strategies. Curr. Top. Microbol. Immunol. 240:95-118 (1999).
Dall'Acqua et al. Antibody humanization by framework shuffling. Methods 36:43-60 (2005).
De Kruif et al. Rapid selection of cell subpopulation-specific human monoclonal antibodies from a synthetic phage antibody library. PNAS USA 92:3938-3942 (1995).
Degen et al. MEMD, a new cell adhesion molecule in metastasizing human melanoma cell lines, is identical to ALCAM (activated leukocyte cell adhesion molecule). Am. J. Pathol. 152:805-813 (1998).
Ditzel et al. Determinants of polyreactivity in a large panel of recombinant human antibodies from HIV-1 infection. J Immunol. 157:739-749 (1996).
Emmert-Buck et al. Laser capture microdissection. Science 274(5289):998-1001 (1996).
Epitope Definition, Stedman's Online Medical Dictionary, 27th Edition, Oct. 5, 2010, Wolters Kluwer Health, Inc.; available at www.stedmans.com.
Fan et al. Noninvasive diagnosis of fetal aneuploidy by shotgun sequencing DNA from maternal blood. PNAS 105:16266-16271 (2008).
Fuh et al. Structure-function studies of two synthetic anti-vascular endothelial growth factor Fabs and comparison with the Avastin Fab. J Biol. Chem. 281:6625-6631 (2006).

(56) References Cited

OTHER PUBLICATIONS

Gao et al. De novo identification of tumor-specific internalizing human antibody-receptor pairs by phage-display methods. J Immunol Meth 274:185-197 (2003).
Gao et al. Unusual conformation of a 3'-thioformacetal linkage in a DNA duplex. J. Biomolecular NMR.34:17-34 (1994).
Garraway et al. From Integrated Genomics to Tumor Lineage Dependency. Cancer Res. 66:2506-2508 (2006).
Geuijen et al. A proteomic approach to tumour target identification using phage display, affinity purification and mass spectrometry. Eur. J. Cancer 41:178-187 (2005).
Goding. Monoclonal Antibodies: Principles and Practice, pp. 59-103 (Academic Press) (1986).
Greenspan et al. Defining epitopes: It's not as easy as it seems. Nature Biotechnology 7:936-937 (1999).
Ha et al. High-content analysis of antibody phage-display library selection outputs identifies tumor selective macropinocytosis-dependent rapidly internalizing antibodies. Mol. Cell Proteomics. 13(12):3320-3331 (2014).
Hakomori et al. Tumor-associated carbohydrate antigens defining tumor malignancy: basis for development of anti-cancer vaccines. Adv. Exp. Med. Biol. 491:369-402 (2001).
Hall et . al. A single amino acid mutation in CDR3 of the 3-14-9 L chain abolished expression of the IDA 10-defined idiotype and antigen bindingJ Immunol. 149:1605-1612 (1992).
Hanisch. O-Glycosylation of the mucin type. Biol. Chem. 382:143-149 (2001).
Harding et al. Class switching in human immunoglobulin transgenic mice. Ann. NY Acad. Sci. 764:536-546 (1995).
Hoet et al. Generation of high-affinity human antibodies by combining donor-derived and synthetic complementarity-determining-region diversity. Nature Biotechnology 23(3):344-348 (Mar. 2005).
Holliger et al. "Diabodies": small bivalent and bispecific antibody fragments. PNAS USA 90(14):6444-6448 (1993).
Hood et al. Molecular farming of industrial proteins from transgenic maize. Adv. Exp. Med. Biol. 464:127-147 (1999).
Hoogenboom et al. Multi-subunit proteins on the surface of filamentous phage: methodologies for displaying antibody (Fab) heavy and light chains. Nucleic Acids Res. 19(15):4133-4137 (1991).
Hughes et al. Counting the Uncountable: Statistical Approaches to Estimating Microbial Diversity. Appl. Environ. Microbiol. 67:4399-4406 (2001).
Hughes et al. The Application of Rarefaction Techniques to Molecular Inventories of Microbial Diversity. Meth. Enzymol. 397:292-308 (2005).
Huie et al. Antibodies to human fetal erythroid cells from a nonimmune phage antibody library. PNAS USA 98:2682-2687 (2001).
Jahn et al. Expression of monovalent fragments derived from a human IgM autoantibody in E. coli. The input of the somatically mutated CDR1/CDR2 and of the CDR3 into antigen binding specificity. Immunobiol. 193:400-419 (1995).
Jones et al. Replacing the complementarity-determining regions in a human antibody with those from a mouse. Nature 321:522-525 (1986).
Klimka, A. et al. Human anti-CD30 recombinant antibodies by guided phage antibody selection using cell panning. British Journal of Cancer 83(2):252-260 (2000).
Kobata et al. Altered glycosylation of proteins produced by malignant cells, and application for the diagnosis and immunotherapy of tumours. Immunol. Cell Biol. 83:429-439 (2005).
Kreitman et al.: Purification and characterization of IL6-PE4E, a recombinant fusion of interleukin 6 with Pseudomonas exotoxin. Bioconjug Chem. 4(6):581-5 (1993).
Kristiansen et al. Expression profiling of microdissected matched prostate cancer samples reveals CD166/MEMD and CD24 as new prognostic markers for patient survival. J. Pathol. 205:359-376 (2005).
Kuroiwa et al. Cloned transchromosomic calves producing human immunoglobulin. Nat Biotechnol 20:889-894 (2002).
Lekkerkerker et al. Chapter 2A: Phage antibodies against human dendritic cell subpopulations obtained by flow cytometry-based selection on freshly isolated cells. J. Immunol. Methods 231:53-63 (1972).
Lewis et al. A Facile, Water-Soluble Method for Modification of Proteins with DOTA. Use of Elevated Temperature and Optimized pH To Achieve High Specific Activity and High Chelate Stability in Radiolabeled Immunoconjugates. Bioconjugate Chem. 5:565-576 (1994).
Liu et al. Applying Phage Antibodies to Proteomics: Selecting Single Chain Fv Antibodies to Antigens Blotted on Nitrocellulose. Anal. Biochem. 286:119-128 (2000).
Liu et al. Mapping Tumor Epitope Space by Direct Selection of Single-Chain Fv Antibody Libraries on Prostate Cancer Cells. Cancer Research 64(2):704-710 (2004).
Liu et al. Recombinant full-length human IgG1s targeting hormone-refractory prostate cancer. J Mol Med (Berl). 85(10):1113-1123 (2007).
Liu et al. Towards proteome-wide production of monoclonal antibody by phage display. J Mol Biol. 315(5):1063-1073 (2002).
Lonberg et al. Human antibodies from transgenic mice. Int Rev Immunol. 13(1):65-93 (1995).
Lowman et al. Affinity maturation of human growth hormone by monovalent phage display. J. Mal. Biol. 234:564-578 (1993).
Lu et al. Application of laser capture microdissection to phage display peptide library screening Oral Surg. Oral Med. Oral Pathol. Oral Radiol. Endod. 98:692-697 (2004).
Lundblad et al. Molecular 'pharming'. Biotechnol. Appl. Biochem. 30:99-108 (1999).
Ma et al. Immunotherapeutic potential of antibodies produced in plants. Trends Biotechnol. 13:522-527 (1995).
Ma et al. Plant antibodies for immunotherapy. Plant Physiol. 109:341-346 (1995).
Mariuzza et al. The structural basis of antigen-antibody recognition. Annu Rev Biophys Biophys Chem 16:139-159 (1987).
Marks et al. By-passing immunization: building high affinity human antibodies by chain shuffling. Biotechnology (NY) 10(7):779-783 (1992).
Marks et al. By-passing immunization: Human antibodies from v-gene libraries displayed on phage. J. Mol. Biol. 222:581-597 (1991).
Marks et al. Molecular evolution of proteins on filamentous phage. Mimicking the strategy of the immune system. J. Biol. Chem. 267:16007-16010 (1992).
McCafferty et al. Phage Antibodies: Filamentous Phage Displaying Antibody Variable Domains. Nature 348:552-554 (1990).
McDonagh et al. Engineered anti-CD70 antibody-drug conjugate with increased therapeutic index. Mol Cancer Ther 7:2913-2923 (2008).
McWhirter et al. Antibodies selected from combinatorial libraries block a tumor antigen that plays a key role in immunomodulation. PNAS USA 103(4):1041-1046 (2006).
Meier et al. Peptide Nucleic Acids (PNAs)-Unusual Properties of Nonionic Oligonucleotide Analogues. Angew. Chem. Int. Ed. Engl. 31(8):1008-1010 (1992).
Mian et al. Structure, function and properties of antibody binding sites. J Mol. Biol. 217:133-151 (1991).
Molecular & Cellular Proteomics: Editorial Policies and Practices, Apr. 2006.
Munson et al. Ligand: a versatile computerized approach for characterization of ligand-binding systems. Anal Biochem. 107(1):220-239 (Sep. 1, 1980).
Narang et al. [6] Improved phosphotriester method for the synthesis of gene fragments. Meth. Enzymol. 68:90-99 (1979).
Nielsen et al. PNA hybridizes to complementary oligonucleotides obeying the Watson-Crick hydrogen bonding rules. Letter to Nature 365:566-568 (1993).
Nielsen et al., Therapeutic efficacy of anti-ErbB2 immunoliposomes targeted by a phage antibody selected for cellular endocytosis. Biochim Biophys Acta 1591:109-118 (2002).
Nord et al. Binding proteins selected from combinatorial libraries of an alpha-helical bacterial receptor domain. Nat. Biotechnol. 15:772-777 (1997).

(56) References Cited

OTHER PUBLICATIONS

O'Connell et al. Phage versus phagemid libraries for generation of human monoclonal antibodies. J. Mol. Biol. 321:49-56 (2002).
Paul. Fundamental Immunology, 3rd Edition, Chapter 9, pp. 292-295 (1993).
PCT/US2008/076704 International Search Report and Written Opinion dated May 4, 2009.
Piazza et al. Internalization and recycling of ALCAM/CD166 detected by a fully human single-chain recombinant antibody. J. Cell Sci. 118:1515-1525 (2005).
Pini et al. Design and use of a phage display library. Human antibodies with subnanomolar affinity against a marker of angiogenesis eluted from a two-dimensional gel. J. Biol. Chem. 273:21769-21776 (1998).
Pirollo et al. Tumor-targeting nanoimmunoliposome complex for short interfering RNA delivery. Hum. Gene Ther. 17:117-124 (2006).
Polymenis et al. Critical binding site amino acids of anti-Z-DNA single chain Fv molecules. Role of heavy and light chain CDR3 and relationship to autoantibody activity. J Immunol. 152:5318-5329 (1994).
Poul et al. Selection of tumor-specific internalizing human antibodies from phage libraries. J. Mol. Biol. 301:1149-1161 (2000).
Queen et al. A humanized antibody that binds to the interleukin 2 receptor. PNAS USA 86:10029-10032 (1989).
Rader et al. A phage display approach for rapid antibody humanization: Designed combinatorial V gene libraries. PNAS USA 95(15): 8910-8915 (Jul. 2, 19981).
Reyes-Reyes et al. A new paradigm for aptamer therapeutic AS1411 action: uptake by macropinocytosis and its stimulation by a nucleolin-dependent mechanism. Cancer Research 70(21):8617-8629 (2010).
Riechmann et al., "Reshaping human antibodies for therapy," Nature 332:323-327 (1988).
Ronnmark et al. Human immunoglobulin A (IgA)-specific ligands from combinatorial engineering of protein A. Eur. J Biochem., 269:2647-2655 (2002).
Ruan et al. Identification of clinically significant tumor antigens by selecting phage antibody library on tumor cells in situ using laser capture microdissection. Mol Cell Proteomics 5(12):2364-2373 (2006).
Sahagan et al. A genetically engineered murine/human chimeric antibody retains specificity for human tumor-associated antigen. J Immunol. 137:1066 (1986).
Saifullah et al. Expression and Characterization of a Novel CD6 Ligand in Cells Derived from Joint and Epithelial Tissues. J. Immunol. 173:6125-6133 (2004).
Saito et al. Distribution of Liposomes into Brain and Rat Brain Tumor Models by Convection-Enhanced Delivery Monitored with Magnetic Resonance Imaging. Cancer Res. 64:2572-2579 (2004).
Saito et al. Gadolinium-loaded liposomes allow for real-time magnetic resonance imaging of convection-enhanced delivery in the primate brain. Exp. Neurol. 196:381-389 (2005).
Sawai et al. Synthesis and Properties of Oligoadenylic Acids Containing 2'-5' Phosphoramide Linkage. Chem. Lett. 13(5):805-808 (1984).
Schier et al. Efficient in vitro affinity maturation of phage antibodies using BIAcore guided selections. Human Antibodies and Hybridomas. 7:97-105 (1996).
Schier, et al. Identification of functional and structural amino-acid residues by parsimonious mutagenesis. Gene. 169(2):147-155 (Mar. 9, 1996).
Schier et al., Isolation of picomolar affinity anti-c-erbB-2 single-chain Fv by molecular evolution of the complementarity determining regions in the center of the antibody binding site. J Mol Biol. 263(4):551-567 (1996).
Sharon et al. Expression of a VHC kappa chimaeric protein in mouse myeloma cells. Nature 309:364 (1984).
Sharon et al. Recombinant poly-clonal antibodies for cancer therapy. J. Cell. Biochem. 96:305-313 (2005).
Shopes. A genetically engineered human IgG mutant with enhanced cytolytic activity. J. Immunol. 148: 2918-2922 (1992).
Silacci et al. Design, construction, and characterization of a large synthetic human antibody phage display library. Proteomics 5:2340-2350 (2005).
Simone et al. Laser-capture microdissection: opening the microscopic frontier to molecular analysis. Trends Genet 14(7):272-276 (1998).
Song et al. Antibody mediated in vivo delivery of small interfering RNAs via cell-surface receptors. Nat. Biotechnol. 23:709-717 (2005).
Stevenson et al. A chimeric antibody with dual Fc regions (bisFabFc) prepared by manipulations at the IgG hinge. Anti-Cancer Drug Design 3:219-230 (1989).
Su et al. Characterization of a new Y-90 labeled DOTA-biotin for pretargeting. J Nucl. Med. 36(5 Suppl): 154P (1995).
Sutherland et al. Lysosomal trafficking and cysteine protease metabolism confer target-specific cytotoxicity by peptide-linked anti-CD30-auristatin conjugates. J Biol. Chem. 281:10540-10547 (2006).
Tan et al. A human-mouse chimeric immunoglobulin gene with a human variable region is expressed in mouse myeloma cells. J Immunol. 135:3564-3567 (1985).
Tomizuka et al. Double trans-chromosomic mice: maintenance of two individual human chromosome fragments containing Ig heavy and kappa loci and expression of fully human antibodies. PNAS USA 97:722-727 (2000).
Uchida et al. Diphtheria toxin and related proteins. I. Isolation and properties of mutant proteins serologically related to diphtheria toxin. J Biol. Chem., 248:3838-3844 (1973).
Uchida et al. Reconstitution of diphtheria toxin from two nontoxic cross-reacting mutant proteins. Science 175:901-903 (1972).
Ugorski et al. Sialyl Lewis(a): a tumor-associated carbohydrate antigen involved in adhesion and metastatic potential of cancer cells. Acta Biochim. Pol. 49(2):303-311 (2002).
U.S. Appl. No. 12/724,282 Final Office Action dated Jul. 19, 2013.
U.S. Appl. No. 12/724,282 Office Action dated Dec. 14, 2012.
U.S. Appl. No. 14/205,101 Office Action dated Jan. 5, 2016.
U.S. Appl. No. 14/486,943 Office Action dated Apr. 19, 2016.
U.S. Appl. No. 14/486,943 Office Action dated Sep. 3, 2015.
U.S. Appl. No. 15/390,378 Office Action dated Oct. 3, 2018.
U.S. Appl. No. 15/418,588 Office Action dated Aug. 3, 2018.
U.S. Appl. No. 15/418,588 Office Action dated Feb. 26, 2019.
Van Der Neut Kolfschoten et al. Anti-inflammatory activity of human IgG4 antibodies by dynamic Fab arm exchange. Science 317:1554-1557 (2007).
Von Kiedrowski et al. Parabolic Growth of a Self-Replicating Hexadeoxy nucleotide Bearing a 3'-5'-Phosphaomidate Linkage. Angew. Chem. Int. Ed. Engl 30(4):423-426 (1991).
Waterhouse et al. Combinatorial infection and in vivo recombination: a strategy for making large phage antibody repertoires. Nucleic Acids Res. 21(9):2265-2266 (May 11, 1993).
Wells. Additivity of mutational effects in proteins. Biochemistry. 29(37): 8509-8517 (1990).
Whitelam et al. Antibody production in transgenic plants. Biochem. Soc. Trans. 22:940-944 (1994).
Williams et al. Structure/function analysis of interleukin-2-toxin (DAB486-IL-2). Fragment B sequences required for the delivery of fragment A to the cytosol of target cells. J Biol. Chem. 265:11885-11889 (1990).
Wolff, et al. Monoclonal antibody homodimers: enhanced antitumor activity in nude mice. Cancer Res. Jun. 1, 1993;53(11):2560-5.
Wu et al. Investigations of N-linked macrocycles for 111In and 90Y labeling of proteins. Int J Rad Appl Instrum B 19(2):239-244 (1992).
Yao et al. Targeting Pancreatic Islets with Phage Display Assisted by Laser Pressure Catapult Microdissection. Am. J. Pathol. 166:625-636 (2005).
Yu et al. The amplification of 1q21 is an adverse prognostic factor in patients with multiple myeloma in a Chinese population. Onco Targets Ther 9:295-302 (2016).
Al-Hujaily et al., Development of novel immunotherapies for multiple myeloma. International Journal of Molecular Sciences 17(9):E1506 (2016).
Al-Lazikani et al. Standard conformations for the canonical structures of immunoglobulins. J. Mol Biology 273(4):927-948 (1997).

(56) References Cited

OTHER PUBLICATIONS

Biran et al. Patients with newly diagnosed multiple myeloma and chromosome 1 amplification have poor outcomes despite the use of novel triplet regimens. Am. J. Hematol. 89(6):616-620 (2014).
Bonifant et al., Toxicity and management in CAR T-cell therapy. Molecular Therapy—Oncolytics 3:16011 (2016).
Choileain et al. The dynamic processing of CD46 intracellular domains provides a molecular rheostat for T cell activation. PLoS One 6(1): e16287 (2011).
Crimeen-Irwin et al. Ligand binding determines whether CD46 Is internalized by clathrin- coated pits or macropinocytosis. The Journal of Biological Chemistry 278(47): 46927-46937 (2003).
De Jong et al., Drug delivery and nanoparticles: applications and hazards. International Journal of Nanomedicine 3:133-149 (2008).
Edelman et al. The covalent structure of an entire yG immunoglobulin molecule. PNAS 63(1):78-85 (1969).
Geuijen et al. Affinity ranking of antibodies using flow cytometry: application in antibody phage display-based target discovery. Journal of Immunological Methods 302(1): 68-77 (2005).
Haraldsdottir et al., Integrating anti-EGFR therapies in metastatic colorectal cancer. Journal of Gastrointestinal Oncology 4(3):285-298 (2013).
Honegger et al. Yet another numbering scheme for immunoglobulin variable domains: an automatic modeling and analysis tool. J Mol Biol 309(3):657-70 (2001).
Kabat et al. Sequences of proteins of immunological interest. NIH Publ. No. 91-3242 1:647-669 (1991).
Lefranc et al. IMGT unique numbering for immunoglobulin and T cell receptor variable domains and Ig superfamily V-like domains. Dev Comp Immunol 27(1):55-77 (2003).
MacCallum et al. Antibody-antigen interactions: contact analysis and binding site topography. J Mol Biol. 262(5):732-745 (1996).
Mantaj et al., Covalent bonding of pyrrolobenzodiazepines (PBDs) to terminal guanine residues within duplex and hairpin DNA fragments. PLoS One. 11(4):e0152303 (2016).
Nemec et al. Gain of 1q21 is an unfavorable genetic prognostic factor for multiple myeloma patients treated with high-dose chemotherapy. Biol Blood Marrow Transplant 16:548-554 (2010).
PCT/US2015/049492 International Search Report and Written Opinion dated Nov. 17, 2015.
PCT/US2017/061124 International Search Report and Written Opinion dated May 11, 2018.
PCT/US2017/061124 Invitation to Pay Additional Fees dated Feb. 12, 2018.
PCT/US2017/061153 International Search Report and Written Opinion dated Mar. 27, 2018.
PCT/US2017/061153 Invitation to Pay Additional Fees dated Jan. 26, 2018.
Schweizer et al., Controlled release of therapeutic antibody formats. European Journal of Pharmaceutics and Biopharmaceutics 88(2):291-309 (2014).
Sherbenou et al. Antibody-drug conjugate targeting CD46 eliminates multiple myeloma cells. J Clin Invest 126:4640-4653 (2016).
Sherbenou et al. CD46 Is Amplified in High-Risk Myeloma with Gain of Chromosome Iq and Selectively Targeted By a Novel Anti-CD46 Antibody-Drug Conjugate. Blood 128:384 (2016).
Su et al. Targeting CD46 for both adenocarcinoma and neuroendocrine prostate cancer. JCI Insight. 3(17):e121497 (2018).
U.S. Appl. No. 15/508,059 Office Action dated May 30, 2019.
U.S. Appl. No. 15/508,059 Office Action dated Sep. 7, 2018.
Wang et al., Clinical manufacturing of CAR T cells: foundation of a promising therapy. Molecular Therapy—Oncolytics 3:16015 (2016).
Aggarwal. The Prostate Cancer Clinical Trials Consortium: Clinical Research Site Application. Award No. W81XWH-18-2-0039 (Oct. 2019).
Kovtun et al. Cell killing by antibody-drug conjugates. Cancer Letters 255(2):232-40 (2007).
Masters et al. Clinical toxicity of antibody drug conjugates: a meta-analysis of payloads. Invest New Drug 36:121-135 (2018).
NCT03575819 (version Jun. 20, 2019).

U.S. Appl. No. 17/851,340 Office Action dated Apr. 20, 2023.
Acchione et al. Impact of linker and conjugation chemistry on antigen binding, Fc receptor binding and thermal stability of model antibody-drug conjugates. mAbs 4:362-372 (2012).
Agnelli et al. A SNP microarray and FISH-based procedure to detect allelic imbalances in multiple myeloma: an integrated genomics approach reveals a wide gene dosage effect. Genes. Chromosomes Cancer 48(7):603-614 (2009).
Almagro et al. Humanization of antibodies. Front Biosci 13:1619-1633 (2008).
Angerer et al. Demonstration of tissue-specific gene expression by in situ hybridization. Methods Enzymol 152:649-660 (1987).
Axup et al. Synthesis of site-specific antibody-drug conjugates using unnatural amino acids. PNAS 109(40):16101-16106 (2012).
Badescu et al. Bridging disulfides for stable and defined antibody drug conjugates. Bioconjugate Chemistry 25:1124-1136 (2014).
Ballangrud et al. Response of LNCaP Spheroids After Treatment With an Alpha-Particle Emitter (213Bi)-labeled Anti-Prostate-Specific Membrane Antigen Antibody (J591) Cancer Res. 61:2008-2014 (2001).
Barany et al. The Peptide: Analysis Synthesis, Biology, editors E. Gross and J. Meienhofer. Academic Press, New York (1980) Chapter 1(vol. 2):3-254.
Barringer et al. Blunt-end and single-strand ligations by *Escherichia coli* ligase: influence on an in vitro amplification scheme. Gene 89(1):117-22 (1990).
Beaucage et al. The Functionalization of Oligonucleotides Via Phosphoramidite Derivative. Tetrahedron Report No. 329. 49(10):1925-1963 (1993).
Bird et al. Single-chain antigen-binding proteins. Science 242:423-442 (1988).
Bloeman et al. Adhesion molecules: a new target for immunoliposome-mediated drug delivery. FEBS Lett. 357:140 (1995).
Boeggeman et al. Site specific conjugation of fluoroprobes to the remodeled Fc N-glycans of monoclonal antibodies using mutant glycosyltransferases: application for cell surface antigen detection. Bioconjug. Chem. 20:1228-1236 (2009).
Borchardt et al. Targeted actinium-225 in Vivo Generators for Therapy of Ovarian Cancer Cancer Res. 63:5084-50 (2003).
Borlinghaus et al. Radiosensitizer Conjugation to the Carcinoma 19-9 Monoclonal Antibody. Cancer Research 47(15):4071-4075 (Aug. 1, 1987).
Boswell et al. Differential Effects of Predosing on Tumor and Tissue Uptake of an 111In-Labeled Anti-TENB2 Antibody-Drug Conjugate. Soc. Nuclear Med. 53:1454-1461 (2012).
Boswell et al. Impact of Drug Conjugation on Pharmacokinetics and Tissue Distribution of Anti-STEAP1 Antibody-Drug Conjugates in Rats. Bioconjug Chem. 22(10):1994-2004 (2011).
Brill et al. Synthesis of Oligodeoxynucleoside Phosphorodithioatesvia Thioamidites. J Am Chem Soc 111:2321 (1989).
Briscoe et al. Delivery of superoxide dismutase to pulmonary epithelium via pH-sensitive liposomes. Am. J. Physiol. 1233:134 (1995).
Brummell et al.: Probing the Combining Site of an Anti-Carbohydrate Antibody by Saturation-Mutagenesis: Role of the Heavy-Chain CDR3 Residues; Biochemistry 32: 1180-1187 (1993).
Burks et al.: In vitro scanning saturation mutagenesis of an antibody binding pocket; Proc. Natl. Acad. Sci. USA (94) pp. 412-417 (1997).
Caban et al. Size matters: a view of selenocysteine incorporation from the ribosome. Cell Mol. Life Sci. 63:73-81 (2006).
Carlsson et al. Screening for genetic mutations. Nature 380:207 (1996).
Chaudhary et al. Activity of a recombinant fusion protein between transforming growth factor type alpha and Pseudomonas toxin. PNAS USA 84:4538-4542 (1987).
Chee et al. Accessing genetic information with high-density DNA arrays. Science 274:610-614 (1996).
Cheung et al. Epitope-specific antibody response to the surface antigen of duck hepatitis B virus in infected ducks. Virology 176(2):546-552 (1990).
Clackson et al. Making antibody fragments using phage display libraries. Nature 352(6336):624-628 (1991).

(56) References Cited

OTHER PUBLICATIONS

Colberre-Garapin et al. A new dominant hybrid selective marker for higher eukaryotic cells. J Mol Biol 150:1-14 (1981).
Cole et al. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), New York: Alan R. Liss, Inc. pp. 77-96 (1985).
Connor et al. Monoclonal antibody and liposomes. Pharm. Ther., 28:341-365 (1985).
Crouse et al. Expression and amplification of engineered mouse dihydrofolate reductase minigenes. Mol Cell Biol 3(2):257-266 (1983).
De Mesmaeker et al. Comparison of Rigid and Flexible Backbones in Antisense Oligonucleotides Bioorg Med Chem Lett 4(3):395-398 (1994).
Dempcy et al. Synthesis of a thymidyl pentamer of deoxyribonucleic guanidine and binding studies with DNA homopolynucleotides. PNAS USA 92:6097-6101 (1995).
Dornan et al. Therapeutic potential of an anti-CD79b antibody-drug conjugate, anti-CD79b-vc-MMAE, for the treatment of non-Hodgkin lymphoma. Blood 114(13):2721-2729 (2009).
Egholm et al. Peptide Nucleic Acids (PNA) Oligonucleotide Analogues with an Achiral Peptide Backbone. J Am Chem Soc 114:1895-1897 (1992).
Fortina, et al. Digital mRNA profiling. Nat Biotechnol. Mar. 2008;26(3):293-4.
Francisco et al. cAC10-vcMMAE, an anti-CD30-monomethyl auristatin E conjugate with potent and selective antitumor activity. Blood 102(4):1458-65 (2003).
Frka-Petesic et al. Aggregation of Antibody Drug Conjugates at Room Temperature: SAXS and Light Scattering Evidence for Colloidal Instability of a Specific Subpopulation. Langmuir 32(19):4848-61 (2016).
Galush et al. Chapter 13: Formulation Development of Antibody-Drug Conjugates. Antibody-Drug Conjugates 1045:217-233 (2013).
Gibson et al. A novel method for real time quantitative RT-PCR. Genome Research 6:995-1001 (1996).
Goldspiel et al. Human gene therapy. Clin Pharm 12:488-505 (1993).
Guatelli et al. Isothermal, in vitro amplification of nucleic acids by a multienzyme reaction modeled after retroviral replication. PNAS USA 87(5):1874-1878 (1990).
Hanamura et al., Frequent gain of chromosome band 1q21 in plasma-cell dyscrasias detected by fluorescence in situ hybridization: incidence increases from MGUS to relapsed myeloma and is related to prognosis and disease progression following tandem stem-cell transplantation. Blood 108:1724-1732 (2006).
Hanes et al. In vitro selection and evolution of functional proteins by using ribosome display. PNAS USA 94:4937-4942 (1997).
Heid et al. Real time quantitative PCR. Genome Res. 6(10):986-994 (1996).
Hofer et al. Molecularly defined antibody conjugation through a selenocysteine interface. Biochem. 48:12047-12057 (2009).
Horn et al. Oligonucleotides with Alternating Anionic and Cationic Phosphoramidate Linkages: Synthesis and Hybridization of Sterouniform Isomers. Tetrahedron Letters 37(6):743-746 (1996).
Huse et al. Generation of a large combinatorial library of the immunoglobulin repertoire in phage lambda. Science 246(4935):1275-1281 (1989).
Huston et al. Protein engineering of antibody binding sites: recovery of specific activity in an anti-digoxin single-chain Fv analogue produced in *Escherichia coli*. PNAS USA 85(16):5879-5883 (1988).
Jayaraman et al. CAR-T: Elements and their synergistic function. EBioMedicine 58:102931 (2020).
Jeger et al. Site-specific and stoichiometric modification of antibodies by bacterial transglutaminase. Ange Chem Int. Ed. Engl 49:9995-9997 (2010).
Jenkins et al. The Biosynthesis of Carbocyclic Nucleosides. Chemical society reviews 24:169-176 (1995).

Jung et al. Hybridization of Alternating Cationic/Anionic Oligonucleotides to RNA Segments. Nucleosides & Nucleotides 13(6 &7):1597-1605 (1994).
Junutula et al. Rapid identification of reactive cysteine residues for site-specific labeling of antibody-Fabs. J. Immunol. Meth. 332:41-52 (2008).
Junutula et al. Site-specific conjugation of a cytotoxic drug to an antibody improves the therapeutic index. Nat Biotechnol. 26(8):925-32 (2008).
Kiedrowshi et al. Parabolic Growth of a Self-Replicating Hexadeoxynucleotide Bearing a 3'- 5'-Phosphoamidate Linkage Angew. Chem. Intl. Ed. English 30(4):423-426 (1991).
Kiick et al. Incorporation of azides into recombinant proteins for chemoselective modification by the Staudinger ligation. PNAS 99:1:19-24 (2002).
Kirkland et al. Analysis of the fine specificity and cross-reactivity of monoclonal anti-lipid A antibodies. J Immunol. 137(11):3614-3619 (1986).
Kobayashi et al.: Tryptophan H33 plays an important role in pyrimidine (6-4) pyrimidone photoproduct binding by a high-affinity antibody; Protein Engineering 12(10) 879-884 (1999).
Kohler et al. Continuous cultures of fused cells secreting antibody of predefined specificity. Nature 256:495-497 (1975).
Kozbor et al. The production of monoclonal antibodies from human lymphocytes. Immunology Today 4:72-79 (1983).
Krall et al. Small targeted cytotoxics: current state and promises from DNA-encoded chemical libraries. Angewandte Chem. Int. Ed. 52:1384-1402.
Kryukov et al. Characterization of mammalian selenoproteomes. Science 300:1439-1443 (2003).
Kutmeier et al. Assembly of humanized antibody genes from synthetic oligonucleotides using a single-round PCR. BioTechniques 17:242 (1994).
Kwoh et al. Transcription-based amplification system and detection of amplified human immunodeficiency virus type 1 with a bead-based sandwich hybridization format. PNAS USA 86:1173-1177 (1989).
Landegren et al. A Ligase-Mediated Gene Detection Technique. Science 241:1077-1080 (1988).
Letsinger et al. Cationic Oligonucleotides. J Am Chem Soc 110:4470-4471 (1988).
Letsinger et al. Effects of pendant groups at phosphorus on binding properties of d-ApA analogues. Nucleic Acids Research 14(8):3487-3499 (1986).
Letsinger et al. Phosphoramidate Analogs of Oligonucleotides. J Org Chem 35(11):3800-3803 (1970).
Liu et al. Genetic incorporation of unnatural amino acids into proteins in mammalian cells. Nat. Meth. 4:239-244 (2007).
Lonberg, et al. Antigen-specific human antibodies from mice comprising four distinct genetic modifications. Nature. Apr. 28, 1994;368(6474):856-9.
Lowy et al., Isolation of transforming DNA: Cloning the hamster aprt gene. Cell 22:817-823 (1980).
Mag et al. Synthesis and selective cleavage of an oligodeoxynucleotide containing a bridged internucleotide 5'-phosphorothioate linkage. Nucleic Acids Research 19(7):1437-1441 (1991).
McDevitt et al. Tumor Therapy With Targeted Atomic Nanogenerators. Science 294:1537-1540 (2001).
Merrifield et al. Solid Phase Peptide Synthesis I. J Am Chem Soc 85:2149-2154 (1963).
Meyers et al. Optimal alignments in linear space. CABIOS 4:11-17 (1989).
Moldenhauer, et al. Identity of HML-1 antigen on intestinal intraepithelial T cells and of B-ly7 antigen on hairy cell leukaemia. Scand J Immunol. 32(2):77-82 (Aug. 1990).
Morel et al. Monoclonal antibodies to bovine serum albumin: Affinity and specificity determinations. Mol Immunol. 25(1):7-15 (1988).
Morgan et al. Human gene therapy. Ann Rev Biochem 62:191-217 (1993).
Morrison et al. Chimeric human antibody molecules: mouse antigen-binding domains with human constant region domains. PNAS USA 81(21):6851-6855 (1984).

(56) References Cited

OTHER PUBLICATIONS

Mulligan et al. Selection for animal cells that express the *Escherichia coli* gene coding for xanthine-guanine phosphoribosyltransferase. PNAS USA 78(4):2072-2076 (1981).
Mulligan. The basic science of gene therapy. Science. 260(5110):926-932 (1993).
Needleman et al. A general method applicable to the search for similarities in the amino acid sequence of two proteins. Journal of molecular biology 48(3):443-453 (1970).
Neuberger et al. Recombinant antibodies possessing novel effector functions. Nature 312(5995):604-608 (1984).
Nielsen et al. Advances in targeted delivery of small interfering RNA using simple bioconjugates. Expert Opinion On Drug Delivery 11(5):791-822 (2014).
O'Hare et al. Transformation of mouse fibroblasts to methotrexate resistance by a recombinant plasmid expressing a prokaryotic dihydrofolate reductase. PNAS USA 78:1527-1531 (1981).
Owais et al. Chloroquine encapsulated in malaria-infected erythrocyte-specific antibody-bearing liposomes effectively controls chloroquine-resistant Plasmodium berghei infections in mice. Antimicrob. Agents Chemother. 39:180-184 (1995).
Pastinen et al. Minisequencing: a specific tool for DNA analysis and diagnostics on oligonucleotide arrays. Genome Res. 7:606-614 (1997).
Pauwels et al. Biological activity of new 2-5A analogues. Chemica scripta 26:141-145 (1986).
PCT/US2021/044832 International Search Report and Written Opinion dated Nov. 22, 2021.
Pinkel et al. High resolution analysis of DNA copy number variation using comparative genomic hybridization to microarrays. Nat Genet 20:207-211 (1998).
Pollack et al. Genome-wide analysis of DNA copy-number changes using cDNA microarrays. Nat. Genet. 23(1):41-6 (1999).
Qasba et al. Substrate-induced conformational changes in glycosyltransferases. Trends Biochem. Sci. 30:53-62 (2005).
Ramakrishnan et al. Structure-based design of beta 1,4-galactosyltransferase I (beta 4Gal-T1) with equally efficient N-acetylgalactosaminyltransferase activity: point mutation broadens beta 4Gal-T1 donor specificity. J. Biol. Chem. 277:20833-20839 (2002).
Rande. Drug delivery systems. 1. site-specific drug delivery using liposomes as carriers. J. Clin. Pharmacol. 29:685 (1989).
Rawls. Optimistic About Antisense. C&E News Washington (pp. 35-39) (Jun. 2, 1997).
Reiter et al. Disulfide stabilization of antibody Fv: computer predictions and experimental evaluation. Protein Eng. 8:1323-1331 (1995).
Santerre et al. Expression of prokaryotic genes for hygromycin B and G418 resistance as dominant-selection markers in mouse L cells. Gene 30(1-3):147-156 (1984).
Shen et al. Conjugation site modulates the in vivo stability and therapeutic activity of antibody-drug conjugates. Nat Biotechnol. 22;30(2):184-9 (2012).
Siegall et al. Cytotoxic activities of a fusion protein comprised of TGF alpha and Pseudomonas exotoxin. FASEB J. 3:2647-2652 (1989).
Siegall et al. Functional Analysis of Domains II, Ib, and III of Pseudomonas Exotoxin. J Biol Chem 264(24):14256-14261 (Aug. 25, 1989).
Skerra et al. Assembly of a functional Immunoglobulin Fv fragment in *Escherichia coli*. Science 240(4855):1038-1041 (1988).
Sprinzl et al. Enzymatic Incorporation of ATP and CTP Analogues into the 3' End of tRNA. Eur J Biochem 81:579-589 (1977).
Stahli et al. Distinction of epitopes by monoclonal antibodies. Methods in Enzymology 92:242-253 (1983).
Strejan et al. Suppression of chronic-relapsing experimental allergic encephalomyelitis in strain-13 guinea pigs by administration of liposome-associated myelin basic protein. J Neuroimmunol 7:27 (1984).
Strop et al. Location matters: site of conjugation modulates stability and pharmacokinetics of antibody drug conjugates. Chem Biol 20(2):161-167 (2013).
Sunbul et al. Site specific protein labeling by enzymatic post-translational modification. Org. Biomol. Chem. 7:3361-3371 (2009).
Szybalska et al. Genetics of human cell line. IV. DNA-mediated heritable transformation of a biochemical trait. PNAS USA 48:2026-2034 (1962).
Takeda et al. Construction of chimaeric processed immunoglobulin genes containing mouse variable and human constant region sequences. Nature 314(6010):452-454 (1985).
Thorpe et al. Monoclonal Antibodies in Clinical Medicine, Academic Press, pp. 168-190 (1982).
Tolstoshev. Gene Therapy, Concepts, Current Trials and Future Directions. Ann. Rev. Pharmacol. Toxicol. 32:573-596 (1993).
Umezawa et al. Liposome targeting to mouse brain: mannose as a recognition marker. Biochem. Biophys. Res. Commun. 153:1038 (1988).
U.S. Appl. No. 16/348,135 Office Action dated Apr. 13, 2021.
U.S. Appl. No. 16/348,135 Office Action dated Oct. 25, 2021.
U.S. Appl. No. 16/596,684 Office Action dated Jul. 14, 2022.
U.S. Appl. No. 16/691,417 Office Action dated Apr. 14, 2022.
U.S. Appl. No. 16/691,417 Office Action dated Dec. 15, 2022.
Vitetta et al. Redesigning nature's poisons to create anti-tumor reagents. Science 238(4830):1098-1104 (1987).
Waldmann. Monoclonal antibodies in diagnosis and therapy. Science 252:1657-1662 (1991).
Wan et al. Cloning differentially expressed mRNAs. Nat Biotechnol 14:1685-91 (1996).
Wang et al. Addition of the keto functional group to the genetic code of *Escherichia coli*. PNAS USA 100:56-61 (2003).
Ward et al. Binding activities of a repertoire of single immunoglobulin variable domains secreted from *Escherichia coli*. Nature 341(6242):544-546 (1989).
Wigler et al. Transfer of purified herpes virus thymidine kinase gene to cultured mouse cells. Cell 11:223-232 (1977).
Wigler et al. Transformation of mammalian cells with an amplifiable dominant-acting gene. PNAS USA 77:3567-3570 (1980).
Wu et al. Delivery systems for gene therapy. Biotherapy 3:87-95 (1991).
Wu et al. The ligation amplification reaction (LAR)—amplification of specific DNA sequences using sequential rounds of template-dependent ligation. Genomics 4:560 (1989).
Yokoyama et al. Properties and applications of microbial transglutaminase. Appl. Microbial. Biotechnol. 64:447-454 (2004).
Young et al. An enhanced system for unnatural amino acid mutagenesis in *E. coli*. J Mol Biol 395(2):361-374 (2010).
Yu et al., The amplification of 1q21 is an adverse prognostic factor in patients with multiple myeloma in a Chinese population. OncoTarget Ther. 9:295-302 (2016).
Zhan et al. Gene-expression signature of benign monoclonal gammopathy evident in multiple myeloma is linked to good prognosis. Blood 109(4):1692-1700 (2007).
Zhan et al. Global gene expression profiling of multiple myeloma, monoclonal gammopathy of undetermined significance, and normal bone marrow plasma cells. Blood 99(5):1745-1757 (2002).

\* cited by examiner

CD8—hinge region
CD28/4-1BB- co-stimulatory domains
CD3z – CD3 Zeta domain (T-cell activating)
IRES – internal ribosome entry
4-1BB-L  - 41-BB ligand

SEQUENCE LISTING

<160> NUMBER OF SEQ ID NOS: 204

<210> SEQ ID NO 1
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Val Gln Ser Gly Gly Gly Val Val Gln Pro Gly Arg
1               5                   10                  15

Ser Leu Arg Leu Ala Cys Ala Ala Ser Gly Leu Thr Val Asn Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Gly Tyr Phe Asp Leu Trp Gly Arg Gly Thr Leu Val
            100                 105                 110

Thr Val Ser Ser
        115

<210> SEQ ID NO 2
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Ser Tyr Thr Ser Gly
                85                  90                  95

Thr Trp Leu Phe Gly Gly Gly Thr Lys Leu Thr Val Leu
            100                 105

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

```
Gly Leu Thr Val Asn Asn Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Ser Tyr Asp Gly Asn Asn Lys
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Lys Gly Gly Gly Tyr Phe Asp Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ser Asn Ile Gly Ala Gly Tyr Asp
1               5

<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Asn Asn
1

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Ser Tyr Thr Ser Gly Thr Trp Leu
1               5

<210> SEQ ID NO 9
<211> LENGTH: 120
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 9

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Leu
        35                  40                  45

Ser Phe Ile Ser Tyr Asp Gly Asp Glu Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Trp Cys
                85                  90                  95

Ala Lys Ala Ser Gly Tyr Gly Met Gly Ile Leu Asp Tyr Trp Gly Gln
            100                 105                 110

Gly Thr Leu Val Thr Val Ser Ser
        115                 120

<210> SEQ ID NO 10
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Val
            20                  25                  30

Ser Trp Phe Gln Gln Lys Pro Gly Gln Ala Pro Val Phe Val Met Tyr
        35                  40                  45

Gly Gln Asn Asn Arg Pro Ser Gly Ile Ser Glu Arg Phe Ser Gly Ser
50                  55                  60

Ser Ser Gly Asn Thr Ala Ser Leu Ile Ile Thr Gly Ala Gln Ala Glu
65                  70                  75                  80

Asp Glu Ala Asp Tyr Tyr Cys His Ser Arg Asp Ser Ser Gly Thr His
                85                  90                  95

Leu Arg Val Phe Gly Gly Gly Thr Lys Leu Thr Val Leu
            100                 105

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Phe Thr Phe Ser Thr Tyr Gly
1               5

<210> SEQ ID NO 12
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Phe Ile Ser Tyr Asp Gly Asp Glu Lys
1               5

<210> SEQ ID NO 13
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ala Lys Ala Ser Gly Tyr Gly Met Gly Ile Leu Asp Tyr
1               5                   10

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Leu Arg Ser Tyr Tyr
1               5

<210> SEQ ID NO 15
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gln Asn
1

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

His Ser Arg Asp Ser Ser Gly Thr His Leu Arg Val
1               5                   10

<210> SEQ ID NO 17
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Val Gln Ser Gly Gly Gly Val Val Gln Pro Gly Arg
```

```
                1               5                   10                  15
Ser Leu Arg Leu Ala Cys Ala Ala Ser Gly Phe Thr Val Asn Asn Tyr
                    20                  25                  30
Ala Met His Trp Val Arg Gln Ala Pro Gly Lys Gly Leu Glu Trp Val
            35                  40                  45
Ala Val Ile Ser Tyr Asp Gly Asn Asn Lys Tyr Tyr Ala Asp Ser Val
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Gly Gly Gly Tyr Phe Asp Leu Trp Gly Arg Gly Thr Leu Val
                    100                 105                 110
Thr Val Ser Ser
            115
```

<210> SEQ ID NO 18
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Ile Gly Ala Gly
                    20                  25                  30
Tyr Asp Val His Trp Tyr Gln Gln Leu Pro Gly Thr Ala Pro Lys Leu
            35                  40                  45
Leu Ile Tyr Gly Asp Asn Asn Arg Pro Ser Gly Val Pro Asp Arg Phe
        50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Ser Ser Tyr Thr Ser Gly
                85                  90                  95
Thr Trp Leu Phe Gly Gly Gly Thr Lys Leu Thr Val Leu
            100                 105
```

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Gly Phe Thr Val Asn Asn Tyr Ala
1               5
```

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Ile Ser Tyr Asp Gly Asn Asn Lys
1               5

<210> SEQ ID NO 21
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Lys Gly Gly Gly Tyr Phe Asp Leu
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Ser Asn Ile Gly Ala Gly Tyr Asp
1               5

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Asp Asn
1

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ser Ser Tyr Thr Ser Gly Thr Trp Leu
1               5

<210> SEQ ID NO 25
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Gln Gln Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45
```

Ala Phe Ile Arg Ser Asp Gly Ser Lys Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg His Gly Asn Tyr Phe Asp Ser Trp Gly Gln Gly Thr Leu Val
            100                 105                 110

Thr Val Ser Ser
        115

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Ser Pro Ser Phe Leu Ser Ala Ser Val Gly
 1               5                  10                  15

Asp Arg Val Thr Ile Thr Cys Arg Ala Ser Gln Gly Ile Ser Ser Tyr
                 20                  25                  30

Leu Ala Trp Tyr Gln Gln Lys Pro Gly Lys Ala Pro Lys Leu Leu Ile
             35                  40                  45

Tyr Ala Ala Ser Thr Leu Gln Ser Gly Val Pro Ser Ser Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Ala Ser Tyr Pro Leu
                 85                  90                  95

Thr Phe Gly Gly Gly Thr Lys Val Asp Ile Lys
            100                 105

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Phe Thr Phe Ser Ser Tyr Ala
 1               5

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ile Arg Ser Asp Gly Ser Lys Lys
 1               5

<210> SEQ ID NO 29
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Ala Arg His Gly Asn Tyr Phe Asp Ser
1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Gly Ile Ser Ser Tyr
1               5

<210> SEQ ID NO 31
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Ala Ser
1

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gln Leu Ala Ser Tyr Pro Leu Thr
1               5

<210> SEQ ID NO 33
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Val Gln Leu Val Gln Ser Gly Gly Val Val Gln Pro Gly Arg
1               5                   10                  15

Ser Leu Arg Leu Ala Cys Ala Ala Ser Gly Phe Thr Val Asn Asn Tyr
                20                  25                  30

Ala Met His Trp Val Arg Gln Ala Pro Gly Lys Gly Leu Glu Trp Val
            35                  40                  45

Ala Val Ile Ser Tyr Asp Gly Asn Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                 85                  90                  95

Ala Lys Gly Gly Gly Tyr Phe Asp Leu Trp Gly Arg Gly Thr Leu Val
            100                 105                 110

Thr Val Ser Ser
        115

<210> SEQ ID NO 34
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Gly Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Ser Ser Tyr Thr Ser Gly
                85                  90                  95

Thr Trp Leu Phe Gly Gly Gly Thr Lys Leu Thr Val Leu
            100                 105

<210> SEQ ID NO 35
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gly Phe Thr Val Asn Asn Tyr Ala
1               5

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ile Ser Tyr Asp Gly Asn Asn Lys
1               5

<210> SEQ ID NO 37
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37
```

Ala Lys Gly Gly Gly Tyr Phe Asp Leu
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ser Ser Asn Ile Gly Ala Gly Tyr Asp
1               5

<210> SEQ ID NO 39
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Asn Asn
1

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Ser Tyr Thr Ser Gly Thr Trp Leu
1               5

<210> SEQ ID NO 41
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Arg Ile Ala Ala Ala Gly Arg Arg Tyr Trp Gly
            100                 105                 110

Gln Gly Thr Leu Val Thr Val Ser Ser

```
              115                 120

<210> SEQ ID NO 42
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Ser Ala Leu Thr Gln Pro Pro Ser Ala Ser Ala Thr Pro Gly Gln
1               5                   10                  15

Arg Val Thr Ile Ser Cys Ser Gly Arg Thr Ser Asn Ile Gly Ser Asn
            20                  25                  30

His Val Tyr Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Thr Trp Asp Asp Ser Leu
                85                  90                  95

Ser Gly Glu Val Phe Gly Gly Gly Thr Lys Leu Thr Val Leu
            100                 105                 110

<210> SEQ ID NO 43
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Phe Thr Phe Ser Asp Tyr Tyr
1               5

<210> SEQ ID NO 44
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ile Ser Ser Ser Gly Ser Thr Ile
1               5

<210> SEQ ID NO 45
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Arg Asp Tyr Gly Arg Ile Ala Ala Ala Gly Arg Arg Tyr
1               5                   10

<210> SEQ ID NO 46
<211> LENGTH: 8
```

<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Ser Asn Ile Gly Ser Asn His
1               5

<210> SEQ ID NO 47
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Arg Asn Asn
1

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ala Thr Trp Asp Asp Ser Leu Ser Gly Glu Val
1               5                   10

<210> SEQ ID NO 49
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Gln Glu Ser Gly Gly Gly Val Val Arg Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Arg Ile Ala Ala Ala Gly Arg His Tyr Trp Gly
            100                 105                 110

Gln Gly Thr Leu Val Thr Val Ser Ser
        115                 120

<210> SEQ ID NO 50
<211> LENGTH: 109
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 50

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Thr His
                85                  90                  95

Leu Glu Val Phe Gly Gly Gly Thr Lys Val Thr Val Leu
            100                 105

<210> SEQ ID NO 51
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gly Phe Thr Phe Ser Asp Tyr Tyr
1               5

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ile Ser Ser Ser Gly Ser Thr Ile
1               5

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Arg Asp Tyr Gly Arg Ile Ala Ala Ala Gly Arg His Tyr
1               5                   10

<210> SEQ ID NO 54
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54
```

```
Ser Leu Arg Ser Tyr Tyr
1               5
```

<210> SEQ ID NO 55
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Gly Lys Asn
1
```

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Asn Ser Arg Asp Ser Ser Gly Thr His Leu Glu Val
1               5                   10
```

<210> SEQ ID NO 57
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Arg Ile Ala Ala Ala Gly Arg His Tyr Trp Gly
            100                 105                 110

Gln Gly Thr Leu Val Thr Val Ser Ser
        115                 120
```

<210> SEQ ID NO 58
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

```
Ser Ser Glu Leu Thr Gln Asp Pro Ala Val Ser Val Ala Leu Gly Gln
```

```
                1               5                  10                  15
Thr Val Arg Ile Thr Cys Gln Gly Asp Thr Leu Ser Thr Tyr Tyr Ala
                20                  25                  30

Asn Trp Tyr Gln Gln Lys Pro Gly Gln Ala Pro Val Leu Val Ile Tyr
                35                  40                  45

Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys His Ser Arg Asp Ile Ser Gly Asn Tyr
                85                  90                  95

Leu Phe Ala Ser Gly Thr Lys Leu Thr Val Leu
                100                 105
```

<210> SEQ ID NO 59
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

```
Gly Phe Thr Phe Ser Asp Tyr Tyr
 1               5
```

<210> SEQ ID NO 60
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Ile Ser Ser Ser Gly Ser Thr Ile
 1               5
```

<210> SEQ ID NO 61
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

```
Ala Arg Asp Tyr Gly Arg Ile Ala Ala Ala Gly Arg His Tyr
 1               5                  10
```

<210> SEQ ID NO 62
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Thr Leu Ser Thr Tyr Tyr
 1               5
```

<210> SEQ ID NO 63
<211> LENGTH: 3

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Gly Lys Asn
1

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

His Ser Arg Asp Ile Ser Gly Asn Tyr Leu
1               5                   10

<210> SEQ ID NO 65
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asp Ile Lys Gln Asp Gly Ser Glu Lys Tyr Tyr Val Asp Ser Val
    50                  55                  60

Lys Gly Arg Phe Thr Ile Ser Gly Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Val Gly Ser Thr Ala Ile Asn Tyr Val Arg Ala Tyr Thr
            100                 105                 110

Trp Phe Asp Pro Trp Gly Gln Gly Thr Leu Val Thr Val Ser Ser
        115                 120                 125

<210> SEQ ID NO 66
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Ser Arg Gln Leu Pro Gly Thr Ala Pro Lys Leu Leu
        35                  40                  45
```

```
Ile Tyr Ser Asn Asn Gln Arg Pro Ser Gly Val Pro Asp Arg Phe Ser
        50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Ala Ala Trp Asp Asp Ser Leu
                 85                  90                  95

Asn Val Tyr Val Phe Gly Thr Gly Thr Lys Val Thr Val Leu
            100                 105                 110

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gly Phe Thr Phe Ser Ser Tyr Trp
1               5

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ile Lys Gln Asp Gly Ser Glu Lys
1               5

<210> SEQ ID NO 69
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Lys Asp Val Gly Ser Thr Ala Ile Asn Tyr Val Arg Ala Tyr Thr
1               5                   10                  15

Trp Phe Asp Pro
            20

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Ser Asn Ile Gly Ser Asn Thr
1               5

<210> SEQ ID NO 71
<211> LENGTH: 3
<212> TYPE: PRT
<213> ORGANISM: Artificial Sequence
<220> FEATURE:
<223> OTHER INFORMATION: Description of Artificial Sequence: Synthetic
```

```
                        peptide

<400> SEQUENCE: 71

Ser Asn Asn
1

<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Ala Ala Trp Asp Asp Ser Leu Asn Val Tyr Val
1               5                   10

<210> SEQ ID NO 73
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Ser Thr Phe Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Gln Gly Leu Tyr Ser Ser Gly Trp Ala Asn Trp Phe Asp Pro Arg
            100                 105                 110

Gly Gln Gly Thr Leu Val Thr Val Ser Ser
        115                 120

<210> SEQ ID NO 74
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Lys Ile Val Leu Thr Gln Ser Pro Ser Ser Leu Ser Ala Ser Val Gly
1               5                   10                  15

Asp Thr Val Thr Ile Ala Cys Arg Ala Ser Arg Asp Ile Arg Asn Asp
            20                  25                  30

Leu Ala Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60
```

```
Ser Gly Ser Gly Thr Glu Phe Ile Leu Thr Ile Ser Ser Leu Gln Pro
65                  70                  75                  80

Glu Asp Phe Ala Thr Tyr Tyr Cys His Arg Leu Asn Ser Tyr Pro Leu
                85                  90                  95

Thr Phe Gly Gly Gly Thr Lys Val Asp Ile Lys
            100                 105
```

```
<210> SEQ ID NO 75
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gly Phe Thr Phe Ser Asn Tyr Ala
1               5

<210> SEQ ID NO 76
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Ile Ser Gly Ser Gly Ser Ser Thr
1               5

<210> SEQ ID NO 77
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ala Gln Gly Leu Tyr Ser Ser Gly Trp Ala Asn Trp Phe Asp Pro
1               5                   10                  15

<210> SEQ ID NO 78
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Arg Asp Ile Arg Asn Asp
1               5

<210> SEQ ID NO 79
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Gly Ala Ser
1
```

-continued

```
<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

His Arg Leu Asn Ser Tyr Pro Leu Thr
1               5

<210> SEQ ID NO 81
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Gln Val Gln Leu Gln Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Met Gly Leu Ala Ala Ala Gly Leu Asp Ala Phe Asp Ile
            100                 105                 110

Trp Gly Gln Gly Thr Thr Val Thr Val Ser Ser
        115                 120

<210> SEQ ID NO 82
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asn Phe Met Leu Thr Gln Pro Ala Ser Leu Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Tyr Ala Pro Lys Leu
        35                  40                  45

Met Ile Tyr Asp Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Ser Thr Pro Trp Val Phe Gly Gly Gly Thr Lys Leu Thr Val Leu
```

-continued

```
<210> SEQ ID NO 83
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Phe Thr Phe Ser Ser Tyr Gly
1               5

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Ile Ser Tyr Asp Gly Ser Asn Lys
1               5

<210> SEQ ID NO 85
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Lys Val Met Gly Leu Ala Ala Ala Gly Leu Asp Ala Phe Asp Ile
1               5                   10                  15

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ser Ser Asp Val Gly Gly Tyr Asn Tyr
1               5

<210> SEQ ID NO 87
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asp Val Ser
1

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 88

Ser Ser Tyr Thr Ser Ser Ser Thr Pro Trp Val
1               5                   10

<210> SEQ ID NO 89
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Ala Met His Trp Val Arg Gln Ala Pro Gly Lys Gly Leu Glu Trp Val
            35                  40                  45

Ala Val Ile Ser Tyr Asp Gly Ser Asn Lys Tyr Tyr Ala Asp Ser Val
        50                  55                  60

Lys Gly Arg Phe Thr Ile Ser Arg Asp Thr Ser Thr Asn Thr Leu Tyr
65                  70                  75                  80

Leu Gln Met Asn Ser Leu Arg Ala Asp Asp Thr Ala Val Tyr Tyr Cys
                85                  90                  95

Gly Arg Glu Ser Ser Gly Ser Pro Gly Val Trp Gly Gln Gly Thr Thr
            100                 105                 110

Val Thr Val Ser Ser
        115

<210> SEQ ID NO 90
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Ser Tyr Val Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Gln
                85                  90                  95

Phe Gly Gly Gly Thr Lys Leu Thr Val Leu
            100                 105

<210> SEQ ID NO 91
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 91

Gly Phe Thr Phe Ser Ser Tyr Ala
1               5

<210> SEQ ID NO 92
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ile Ser Tyr Asp Gly Ser Asn Lys
1               5

<210> SEQ ID NO 93
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Arg Glu Ser Ser Gly Ser Pro Gly Val
1               5                   10

<210> SEQ ID NO 94
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ser Leu Arg Ser Tyr Tyr
1               5

<210> SEQ ID NO 95
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Lys Asn
1

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asn Ser Arg Asp Ser Ser Gly Asn Gln
1               5
```

<210> SEQ ID NO 97
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Thr Asp Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Ile Tyr Tyr Cys Ala
                85                  90                  95

Arg Asp Arg Gly Thr Ser Gly Tyr Asp Trp Ala Trp Phe Asp Leu Trp
            100                 105                 110

Gly Gln Gly Thr Leu Val Thr Val Ser Ser
        115                 120

<210> SEQ ID NO 98
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Thr Tyr Tyr Ala
            20                  25                  30

Ser Trp Tyr Gln Gln Arg Pro Gly Gln Ala Pro Ile Leu Val Leu Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Val Val Phe Gly Gly Gly Thr Lys Leu Thr Val Leu
            100                 105

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Phe Thr Val Ser Ser Asn Tyr

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Ile Tyr Thr Asp Gly Ser Thr
1               5

<210> SEQ ID NO 101
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ala Arg Asp Arg Gly Thr Ser Gly Tyr Asp Trp Ala Trp Phe Asp Leu
1               5                   10                  15

<210> SEQ ID NO 102
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Ser Leu Arg Thr Tyr Tyr
1               5

<210> SEQ ID NO 103
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gly Lys Asn
1

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Asn Ser Arg Asp Ser Ser Gly Asn His Val Val
1               5                   10

<210> SEQ ID NO 105
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 105

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Met Gln Met Asn Ser Leu Arg Ala Glu Asp Thr Ala Val Tyr Tyr Cys
                85                  90                  95

Ala Lys Asp Arg Tyr Tyr Tyr Gly Ser Gly Lys Asp Ala Phe Asp Ile
            100                 105                 110

Trp Gly Arg Gly Thr Met Val Thr Val Ser Ser
            115                 120

<210> SEQ ID NO 106
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Ser Val Leu Thr Gln Pro Ala Ser Val Ser Gly Ser Pro Gly Gln
1               5                   10                  15

Ser Ile Thr Ile Ser Cys Thr Gly Thr Gly Ser Asp Val Gly Ser Tyr
            20                  25                  30

Asn Tyr Val Ser Trp Tyr Gln Gln Asn Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Ser
                85                  90                  95

Ser Thr Leu Val Phe Gly Gly Gly Thr Lys Val Thr Val Leu
            100                 105                 110

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Phe Thr Phe Ser Ser Tyr Ala
1               5

<210> SEQ ID NO 108
<211> LENGTH: 8
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 108

Ile Ser Gly Ser Gly Gly Ser Thr
1               5

<210> SEQ ID NO 109
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Ala Lys Asp Arg Tyr Tyr Tyr Gly Ser Gly Lys Asp Ala Phe Asp Ile
1               5                   10                  15

<210> SEQ ID NO 110
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Gly Ser Asp Val Gly Ser Tyr Asn Tyr
1               5

<210> SEQ ID NO 111
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Glu Val Ser
1

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ser Ser Tyr Thr Thr Ser Ser Thr Leu Val
1               5                   10

<210> SEQ ID NO 113
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gln Val Gln Leu Val Glu Ser Gly Gly Gly Leu Val Gln Pro Gly Gly
1               5                   10                  15
```

Ser Leu Gly Leu Ser Cys Ala Ala Ser Gly Phe Thr Phe Ser Asn Tyr
            20                  25                  30

Trp Met Ser Trp Val Arg Gln Ala Pro Gly Lys Gly Leu Glu Trp Val
        35                  40                  45

Ala Asn Val Arg Gln Asp Gly Gly Gln Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Thr Glu Asp Thr Ala Val Tyr Phe Cys
                85                  90                  95

Val Ser Gln Arg Asn Ser Gly Glu His Asp Tyr Trp Gly Gln Gly Thr
            100                 105                 110

Leu Val Thr Val Ser Ser
            115

<210> SEQ ID NO 114
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Glu Asn Ser Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Trp Asp Ser Ser Gly Asn His Val
                85                  90                  95

Val Phe Gly Gly Gly Thr Lys Leu Thr Val Leu
            100                 105

<210> SEQ ID NO 115
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gly Phe Thr Phe Ser Asn Tyr Trp
1               5

<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Val Arg Gln Asp Gly Gly Gln Lys

```
1               5
```

<210> SEQ ID NO 117
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

```
Val Ser Gln Arg Asn Ser Gly Glu His Asp Tyr
1               5                   10
```

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

```
Ser Leu Arg Ser Tyr Tyr
1               5
```

<210> SEQ ID NO 119
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

```
Gly Glu Asn
1
```

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

```
Asn Ser Trp Asp Ser Ser Gly Asn His Val Val
1               5                   10
```

<210> SEQ ID NO 121
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
```

50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Gly Arg Ile Ala Ala Gly Arg His Tyr Trp Gly
            100                 105                 110

Gln Gly Thr Leu Val Thr Val Ser Ser
        115                 120

<210> SEQ ID NO 122
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Ala Ile Arg Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Arg
                 85                  90                  95

Thr Phe Gly Gln Gly Thr Lys Leu Glu Ile Lys
            100                 105

<210> SEQ ID NO 123
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Phe Thr Phe Ser Asp Tyr Tyr
 1               5

<210> SEQ ID NO 124
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Ile Ser Ser Ser Gly Ser Thr Ile
 1               5

<210> SEQ ID NO 125
<211> LENGTH: 14
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 125

Ala Arg Asp Tyr Gly Arg Ile Ala Ala Ala Gly Arg His Tyr
1               5                   10

<210> SEQ ID NO 126
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Gln Ser Ile Ser Ser Tyr
1               5

<210> SEQ ID NO 127
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Ala Ala Ser
1

<210> SEQ ID NO 128
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Tyr Cys Gln Gln Ser Tyr Ser Thr Pro Arg Thr
1               5                   10

<210> SEQ ID NO 129
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Asp Tyr Gly Arg Ile Ala Ala Ala Gly Arg Asn Tyr Trp Gly
            100                 105                 110

Gln Gly Thr Leu Val Thr Val Ser Ser
        115                 120

<210> SEQ ID NO 130
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asp Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Val Gly Ile Tyr Tyr Cys Met Gln Gly
                85                  90                  95

Leu Gln Thr Pro Ser Phe Gly Gln Gly Thr Lys Leu Glu Ile Lys
            100                 105                 110

<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Phe Thr Phe Ser Asp Tyr Tyr
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Ile Ser Ser Ser Gly Ser Thr Ile
1               5

<210> SEQ ID NO 133
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Arg Asp Tyr Gly Arg Ile Ala Ala Ala Gly Arg Asn Tyr
```

```
<210> SEQ ID NO 134
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gln Ser Leu Leu His Ser Asn Gly Tyr Asp Tyr
1               5                   10

<210> SEQ ID NO 135
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Leu Gly Ser
1

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Met Gln Gly Leu Gln Thr Pro Ser
1               5

<210> SEQ ID NO 137
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Gln Val Gln Leu Gln Glu Ser Gly Gly Gly Val Val Arg Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Gly Arg Ile Ala Ala Ala Gly Arg His Tyr Trp Gly
            100                 105                 110

Gln Gly Thr Leu Val Thr Val Ser Ser
        115                 120
```

```
<210> SEQ ID NO 138
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Pro Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Thr His
                85                  90                  95

Arg Gly Val Phe Gly Gly Gly Thr Lys Leu Thr Val Leu
            100                 105

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Phe Thr Phe Ser Asp Tyr Tyr
1               5

<210> SEQ ID NO 140
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Ile Ser Ser Ser Gly Ser Thr Ile
1               5

<210> SEQ ID NO 141
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Ala Arg Asp Tyr Gly Arg Ile Ala Ala Ala Gly Arg His Tyr
1               5                   10

<210> SEQ ID NO 142
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 142

Ser Leu Arg Ser Tyr Tyr
1               5

<210> SEQ ID NO 143
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

Gly Lys Asn
1

<210> SEQ ID NO 144
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Asn Ser Arg Asp Ser Ser Ser Thr His Arg Gly Val
1               5                   10

<210> SEQ ID NO 145
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Ser Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Ala Glu Asp Thr Ala Val Tyr Tyr Cys
                85                  90                  95

Ala Arg Asp Ile Thr Asp Val Val Gly Val Ser Phe Asp Tyr Trp Gly
            100                 105                 110

Gln Gly Thr Leu Val Thr Val Ser Ser
        115                 120

<210> SEQ ID NO 146
<211> LENGTH: 107
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 146

Asp Ile Gln Leu Thr Gln Ser Pro Ser Ser Leu Ser Ala Ser Val Gly
1               5                   10                  15

Asp Arg Val Thr Ile Thr Cys Arg Ala Ser Arg Ser Ile Ser Thr Tyr
            20                  25                  30

Leu Ser Trp Tyr Gln Gln Lys Pro Gly Lys Ala Pro Lys Leu Leu Ile
        35                  40                  45

Tyr Asp Ala Ser Arg Leu Gln Asn Gly Val Pro Ser Arg Phe Ser Gly
50                  55                  60

Ser Gly Ser Asp Thr Asp Phe Thr Leu Thr Ile Ser Ser Leu Gln Pro
65                  70                  75                  80

Glu Asp Phe Ala Thr Tyr Phe Cys Gln Gln Ser Tyr Asn Pro Pro Trp
                85                  90                  95

Thr Phe Gly Gln Gly Thr Lys Leu Glu Ile Lys
            100                 105

<210> SEQ ID NO 147
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Phe Thr Phe Ser Asp Tyr Tyr
1               5

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ile Ser Ser Ser Gly Ser Ser Ile
1               5

<210> SEQ ID NO 149
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Ala Arg Asp Ile Thr Asp Val Val Gly Val Ser Phe Asp Tyr
1               5                   10

<210> SEQ ID NO 150
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Arg Ser Ile Ser Thr Tyr

<210> SEQ ID NO 151
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 151

Asp Ala Ser
1

<210> SEQ ID NO 152
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 152

Gln Gln Ser Tyr Asn Pro Pro Trp Thr
1               5

<210> SEQ ID NO 153
<211> LENGTH: 123
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 153

Glu Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Glu Tyr Tyr Cys
                85                  90                  95

Ala Lys Val Met Gly Leu Ala Ala Ala Gly Leu Asp Ala Phe Asp Ile
            100                 105                 110

Trp Gly Gln Gly Thr Leu Val Thr Val Ser Ser
        115                 120

<210> SEQ ID NO 154
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 154

Gln Ser Ala Leu Thr Gln Pro Ala Ser Val Ser Gly Ser Pro Gly Gln
1               5                   10                  15

```
Ser Ile Thr Ile Ser Cys Thr Gly Thr Ser Ser Asp Val Gly Gly Tyr
             20                  25                  30

Asn Tyr Val Ser Trp Tyr Gln Gln His Pro Gly Lys Ala Pro Lys Leu
         35                  40                  45

Met Ile Tyr Asp Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
65              70                  75                  80

Gln Ala Glu Asp Glu Ala Tyr Tyr Tyr Cys Ser Ser Tyr Thr Ser Ser
                 85                  90                  95

Ser Asp Pro Trp Val Phe Gly Gly Gly Thr Gln Leu Thr Val Leu
            100                 105                 110

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Gly Phe Thr Phe Ser Ser Tyr Gly
1               5

<210> SEQ ID NO 156
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Ile Ser Tyr Asp Gly Ser Asn Lys
1               5

<210> SEQ ID NO 157
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Ala Lys Val Met Gly Leu Ala Ala Ala Gly Leu Asp Ala Phe Asp Ile
1               5                   10                  15

<210> SEQ ID NO 158
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Ser Ser Asp Val Gly Gly Tyr Asn Tyr Val Ser
1               5                   10

<210> SEQ ID NO 159
<211> LENGTH: 3
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 159

Asp Val Ser
1

<210> SEQ ID NO 160
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 160

Ser Ser Tyr Thr Ser Ser Ser Asp Pro Trp Val
1               5                   10

<210> SEQ ID NO 161
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 161

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Phe
            20                  25                  30

Gly Met His Trp Val Arg Arg Ala Pro Gly Lys Gly Leu Glu Trp Val
        35                  40                  45

Ala Val Ile Ser Tyr Asp Gly Ser Asn Gln Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Gly Ser Arg Pro Gly Gly Gly Tyr Ala Ser Gly Ser Thr Val Ala Tyr
            100                 105                 110

Trp Gly Gln Gly Thr Leu Val Thr Val Ser Ser
        115                 120

<210> SEQ ID NO 162
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Asn Ile Gln Met Thr Gln Ser Pro Ser Ser Leu Ser Ala Ser Val Gly
1               5                   10                  15

Asp Arg Val Thr Ile Thr Cys Arg Ala Gly Gln Pro Ile Ser Thr Tyr
            20                  25                  30

Val Asn Trp Tyr Gln His Lys Pro Gly Lys Ala Pro Lys Leu Leu Ile
        35                  40                  45

Tyr Gly Ala Ser Asn Leu Gln Ser Gly Val Pro Ser Arg Phe Ser Gly
```

```
                50                  55                  60
Gly Gly Ser Ala Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Ser Leu Leu
                 85                  90                  95

Thr Phe Gly Asp Gly Thr Lys Val Glu Ile Lys
            100                 105
```

```
<210> SEQ ID NO 163
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Gly Phe Thr Phe Ser Ser Phe Gly
 1               5
```

```
<210> SEQ ID NO 164
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Ile Ser Tyr Asp Gly Ser Asn Gln
 1               5
```

```
<210> SEQ ID NO 165
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Gly Ser Arg Pro Gly Gly Gly Tyr Ala Ser Gly Ser Thr Val Ala Tyr
 1               5                  10                  15
```

```
<210> SEQ ID NO 166
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Gln Pro Ile Ser Thr Tyr Val Asn
 1               5
```

```
<210> SEQ ID NO 167
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Gly Ala Ser
```

<210> SEQ ID NO 168
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Gln Gln Ser Tyr Ser Ser Leu Leu Thr
1               5

<210> SEQ ID NO 169
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Gln Val Gln Leu Gln Glu Pro Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Gly Arg Ile Lys Ser Lys Thr Asp Glu Gly Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Gly Val Tyr
                85                  90                  95

Tyr Cys Thr Ala Thr Lys Gly Leu Gly Gly Ser Lys Leu Gly Gln Gly
            100                 105                 110

Thr Leu Val Thr Val Ser Ser
        115

<210> SEQ ID NO 170
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

Gln Ser Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ser Asn
            20                  25                  30

Thr Val Ser Trp Ser Arg Gln Leu Pro Gly Thr Ala Pro Lys Leu Leu
        35                  40                  45

Ile Tyr Ser Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Pro Glu Asp Glu Ala Asp Tyr Tyr Cys Gly Thr Trp Asp Ser Ser Leu
                85                  90                  95

```
Ser Ala Tyr Val Phe Gly Thr Gly Thr Lys Leu Thr Val Leu
            100                 105                 110

<210> SEQ ID NO 171
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Asp Tyr Ala Met His
1               5

<210> SEQ ID NO 172
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Arg Ile Lys Ser Lys Thr Asp Glu Gly Thr Thr Asp Tyr Ala Ala Pro
1               5                   10                  15

Val Lys Gly

<210> SEQ ID NO 173
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Thr Lys Gly Leu Gly Gly Ser Lys
1               5

<210> SEQ ID NO 174
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ser Gly Ser Ser Ser Asn Ile Gly Ser Asn Thr Val Ser
1               5                   10

<210> SEQ ID NO 175
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Tyr Ser Asn Asp Gln Arg Pro Ser
1               5

<210> SEQ ID NO 176
<211> LENGTH: 11
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Gly Thr Trp Asp Ser Ser Leu Ser Ala Tyr Val
1               5                   10

<210> SEQ ID NO 177
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Asn Trp Val Arg Gln Ala Pro Gly Lys Gly Leu Glu Trp Val
        35                  40                  45

Gly Arg Ile Lys Ser Lys Thr Asp Glu Gly Thr Thr Asp Tyr Ala Ala
    50                  55                  60

Pro Val Lys Gly Arg Phe Ser Ile Ser Arg Asp Asp Ser Lys Asn Thr
65                  70                  75                  80

Leu Tyr Leu Gln Met Asn Ser Leu Lys Thr Glu Asp Thr Gly Val Tyr
                85                  90                  95

Tyr Cys Thr Ala Thr Lys Gly Leu Gly Gly Ser Lys Leu Gly Gln Gly
            100                 105                 110

Thr Leu Val Thr Val Ser Ser
        115

<210> SEQ ID NO 178
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Thr Val Asn Trp Ser Arg Gln Leu Pro Gly Thr Ala Pro Lys Leu Leu
        35                  40                  45

Ile Tyr Ser Asn Asp Gln Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Pro Glu Asp Glu Ala Asp Tyr Tyr Cys Gly Thr Trp Asp Ser Ser Leu
                85                  90                  95

Ser Ala Tyr Val Phe Gly Thr Gly Thr Lys Leu Thr Val Leu
            100                 105                 110
```

```
<210> SEQ ID NO 179
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Asn Ala Trp Met Asn
1               5

<210> SEQ ID NO 180
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Arg Ile Lys Ser Lys Thr Asp Glu Gly Thr Thr Asp Tyr Ala Ala Pro
1               5                   10                  15

Val Lys

<210> SEQ ID NO 181
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 181

Thr Lys Gly Leu Gly Gly Ser Lys
1               5

<210> SEQ ID NO 182
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Ser Gly Ser Ser Ser Asn Ile Gly Asn Asn Thr Val Asn
1               5                   10

<210> SEQ ID NO 183
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Tyr Ser Asn Asp Gln Arg Pro Ser
1               5

<210> SEQ ID NO 184
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 184

Gly Thr Trp Asp Ser Ser Leu Ser Ala Tyr Val
1               5                   10

<210> SEQ ID NO 185
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Gly Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Ser Arg Ser Leu Leu Asp Tyr Trp Gly Gln Gly Thr Leu Val Thr
            100                 105                 110

Val Ser Ser
        115

<210> SEQ ID NO 186
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Asn Phe Met Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Leu Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Pro
                85                  90                  95

Val Phe Gly Gly Gly Thr Lys Val Thr Val Leu
            100                 105

<210> SEQ ID NO 187
<211> LENGTH: 5
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 187

Ser Tyr Ala Met Gly
1               5

<210> SEQ ID NO 188
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ala Ile Ser Gly Ser Gly Gly Ser Thr Tyr Tyr Ala Asp Ser Val Lys
1               5                   10                  15

Gly

<210> SEQ ID NO 189
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Arg Ser Leu Leu Asp Tyr
1               5

<210> SEQ ID NO 190
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gln Gly Asp Ser Leu Arg Ser Tyr Tyr Ala Ser
1               5                   10

<210> SEQ ID NO 191
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Tyr Gly Lys Asn Asn Arg Pro Ser
1               5

<210> SEQ ID NO 192
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Asn Ser Arg Asp Ser Ser Gly Asn Pro Val
1               5                   10
```

<210> SEQ ID NO 193
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Asn Ser Leu Arg Ala Glu Asp Thr Ala Val Tyr Tyr Cys
                85                  90                  95

Ala Ser Arg Ser Leu Leu Asp Tyr Trp Gly Gln Gly Thr Leu Val Thr
            100                 105                 110

Val Ser Ser
        115

<210> SEQ ID NO 194
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Asn Phe Met Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Leu Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn Pro
                85                  90                  95

Val Phe Gly Gly Gly Thr Lys Val Thr Val Leu
            100                 105

<210> SEQ ID NO 195
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

```
Ser Tyr Ala Met Ser
1               5
```

<210> SEQ ID NO 196
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

```
Ala Ile Ser Gly Ser Gly Gly Ser Thr Tyr Tyr Ala Asp Ser Val Lys
1               5                   10                  15

Gly
```

<210> SEQ ID NO 197
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

```
Arg Ser Leu Leu Asp Tyr
1               5
```

<210> SEQ ID NO 198
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

```
Gln Gly Asp Ser Leu Arg Ser Tyr Tyr Ala Ser
1               5                   10
```

<210> SEQ ID NO 199
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

```
Tyr Gly Lys Asn Asn Arg Pro Ser
1               5
```

<210> SEQ ID NO 200
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

```
Asn Ser Arg Asp Ser Ser Gly Asn Pro Val
1               5                   10
```

<210> SEQ ID NO 201
<211> LENGTH: 32
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 201

```
Lys Pro Tyr Tyr Glu Ile Gly Glu Arg Val Asp Tyr Lys Cys Lys Lys
1               5                   10                  15

Gly Tyr Phe Tyr Ile Pro Pro Leu Ala Thr His Thr Ile Cys Asp Arg
            20                  25                  30
```

<210> SEQ ID NO 202
<211> LENGTH: 750
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 202

```
gctagccagg tgcagctggt gcagtctggg ggaggcgtgg tccagcctgg gaggtccctg      60
agactcgcct gtgcagcctc tggactcacc gtcaacaatt atgctatgca ctgggtccgc     120
caggctccag gcaagggact ggagtgggtg gcagttatat catatgatgg aaacaataaa     180
tactatgcag actccgtgaa gggccgattc accatctcca gagacaattc caagaacacg     240
ctgtatctgc aaatgaacag cctgagagct gaggacacgg ctgtgtatta ctgtgcgaaa     300
gggggtggat acttcgatct ctggggccgt ggcaccctgg tcaccgtctc ctcaggtgga     360
ggcggttcag gcggaggtgg ctctggcggt ggcggatcgc agtctgtgtt gacgcagccg     420
ccctcagtgt ctgggccccc agggcagagg gtcaccatct cctgcactgg gagcagctcc     480
aacatcgggg caggttatga tgtacactgg taccagcagc ttccaggaac agcccccaaa     540
ctcctcatct atggtaacaa caatcggccc tcaggggtcc ctgatcgatt ctctggctcc     600
aagtctggca cctcagcctc cctggccatc actgggctcc aggctgagga tgaggctgat     660
tattactgca gctcatatac aagcggcact tggctgttcg gcgggggggac caagctgacc     720
gtcctacatc atcaccatca ccatctcgag                                      750
```

<210> SEQ ID NO 203
<211> LENGTH: 246
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 203

```
Gln Val Gln Leu Val Gln Ser Gly Gly Gly Val Val Gln Pro Gly Arg
1               5                   10                  15

Ser Leu Arg Leu Ala Cys Ala Ala Ser Gly Leu Thr Val Asn Asn Tyr
            20                  25                  30

Ala Met His Trp Val Arg Gln Ala Pro Gly Lys Gly Leu Glu Trp Val
        35                  40                  45

Ala Val Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Gly Gly Gly Tyr Phe Asp Leu Trp Gly Arg Gly Thr Leu Val
            100                 105                 110

Thr Val Ser Ser Gly Gly Gly Ser Gly Gly Gly Ser Gly Gly
        115                 120                 125

Gly Gly Ser Gln Ser Val Leu Thr Gln Pro Pro Ser Val Ser Gly Ala
    130                 135                 140

Pro Gly Gln Arg Val Thr Ile Ser Cys Thr Gly Ser Ser Ser Asn Ile
145                 150                 155                 160

Gly Ala Gly Tyr Asp Val His Trp Tyr Gln Gln Leu Pro Gly Thr Ala
                165                 170                 175

Pro Lys Leu Leu Ile Tyr Gly Asn Asn Asn Arg Pro Ser Gly Val Pro
            180                 185                 190

Asp Arg Phe Ser Gly Ser Lys Ser Gly Thr Ser Ala Ser Leu Ala Ile
        195                 200                 205

Thr Gly Leu Gln Ala Glu Asp Glu Ala Asp Tyr Tyr Cys Ser Ser Tyr
    210                 215                 220

Thr Ser Gly Thr Trp Leu Phe Gly Gly Gly Thr Lys Leu Thr Val Leu
225                 230                 235                 240

His His His His His His
                245

<210> SEQ ID NO 204
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 204

His His His His His His
1               5
```

US 12,049,511 B2

ENGINEERED CD46-SPECIFIC EFFECTOR CELLS AND USES THEREOF IN THE TREATMENT OF CANCER

CROSS-REFERENCE

This application claims the benefit of U.S. Provisional Application No. 62/420,508, filed Nov. 10, 2016, which application is incorporated herein by reference.

SEQUENCE LISTING

The instant application contains a Sequence Listing which has been submitted electronically in ASCII format and is hereby incorporated by reference in its entirety, Said ASCII copy, created on Nov. 9, 2017, is named 39442-704_601_SL.txt and is 94,317 bytes in size.

BACKGROUND OF THE DISCLOSURE

Engineered effector cells, such as chimeric antigen receptors (CARs), combine the binding specificity of monoclonal antibodies with the potency of immune cells, such as T cells and natural killer (NK) cells. In some instances, an engineered effector cell is utilized for specific targeting of a cancer marker for treatment.

SUMMARY OF THE DISCLOSURE

Disclosed herein, in certain embodiments, are engineered effector cells and pharmaceutical compositions comprising one or more engineered effector cells. In some embodiments, also described herein are treatment methods targeting a patient population characterized by an overexpression of CD46 with one or more engineered effector cells.

Disclosed herein, in certain embodiments, is an engineered effector cell that specifically binds CD46, comprising an engineered antigen binding domain that binds to an epitope of CD46, wherein the engineered antigen binding domain is displayed on the surface of the engineered effector cell. In some embodiments, the engineered effector cell is an engineered T cell. In some embodiments, the engineered effector cell is an engineered natural killer T cell. In some embodiments, the engineered effector cell is an engineered natural killer cell. In some embodiments, the engineered antigen binding domain comprises Fab, Fab', F(ab')$_2$, scFv, sc(Fv)$_2$, dsFv, diabody or binding fragments thereof. In some embodiments, the engineered antigen binding domain comprises scFv. In some embodiments, the engineered antigen binding domain binds to an epitope of CD46 bound by one or more antibodies selected from SEQ ID NOs: 1, 2, 9, 10, 17, 18, 25, 26, 33, 34, 41, 42, 49, 50, 57, 58, 65, 66, 73, 74, 81, 82, 89, 90, 97, 98, 105, 106, 113, 114, 121, 122, 129, 130, 137, 138, 145, 146, 153, 154, 161, 162, 169, 170, 177, 178, 185, 186, 193 or 194. In some embodiments, the engineered antigen binding domain comprises a heavy chain variable region comprising three complementarity determining regions (CDRs) and a light chain variable region comprising three CDRs, wherein the heavy chain variable region comprises (i) a variable heavy (VH) CDR1 that has an amino acid sequence of SEQ ID NO: 3, (ii) a variable heavy (VH) CDR2 that has an amino acid sequence of SEQ ID NO: 4, and (iii) a variable heavy (VH) CDR3 that has an amino acid sequence of SEQ ID NO: 5, and wherein the light chain variable region comprises (iv) a variable light (VL) CDR 1 that has an amino acid sequence of SEQ ID NO: 6, (v) a variable light (VL) CDR 2 that has an amino acid sequence of SEQ ID NO: 7, and (vi) a variable light (VL) CDR 3 that has an amino acid sequence of SEQ ID NO: 8. In some embodiments, the engineered binding domain comprises a heavy chain variable region comprising three complementarity determining regions (CDRs) and a light chain variable region comprising three CDRs, wherein the heavy chain variable region comprises (i) a variable heavy (VH) CDR1 that has an amino acid sequence of SEQ ID NO: 11, (ii) a variable heavy (VH) CDR2 that has an amino acid sequence of SEQ ID NO: 12, and (iii) a variable heavy (VH) CDR3 that has an amino acid sequence of SEQ ID NO: 13, and wherein the light chain variable region comprises (iv) a variable light (VL) CDR 1 that has an amino acid sequence of SEQ ID NO: 14, (v) a variable light (VL) CDR 2 that has an amino acid sequence of SEQ ID NO: 15, and (vi) a variable light (VL) CDR 3 that has an amino acid sequence of SEQ ID NO: 16. In some embodiments, the engineered antigen binding domain comprises a heavy chain variable region comprising three complementarity determining regions (CDRs) and a light chain variable region comprising three CDRs, wherein the heavy chain variable region comprises (i) a variable heavy (VH) CDR1 that has an amino acid sequence of SEQ ID NO: 19, (ii) a variable heavy (VH) CDR2 that has an amino acid sequence of SEQ ID NO: 20, and (iii) a variable heavy (VH) CDR3 that has an amino acid sequence of SEQ ID NO: 21, and wherein the light chain variable region comprises (iv) a variable light (VL) CDR 1 that has an amino acid sequence of SEQ ID NO: 22, (v) a variable light (VL) CDR 2 that has an amino acid sequence of SEQ ID NO: 23, and (vi) a variable light (VL) CDR 3 that has an amino acid sequence of SEQ ID NO: 24. In some embodiments, the engineered antigen binding domain comprises a heavy chain variable region comprising three complementarity determining regions (CDRs) and a light chain variable region comprising three CDRs, wherein the heavy chain variable region comprises (i) a variable heavy (VH) CDR1 that has an amino acid sequence of SEQ ID NO: 27, (ii) a variable heavy (VH) CDR2 that has an amino acid sequence of SEQ ID NO: 28, and (iii) a variable heavy (VH) CDR3 that has an amino acid sequence of SEQ ID NO: 29, and wherein the light chain variable region comprises (iv) a variable light (VL) CDR 1 that has an amino acid sequence of SEQ ID NO: 30, (v) a variable light (VL) CDR 2 that has an amino acid sequence of SEQ ID NO: 31, and (vi) a variable light (VL) CDR 3 that has an amino acid sequence of SEQ ID NO: 32. In some embodiments, the engineered antigen binding domain comprises a heavy chain variable region having at least 80%, 85%, 90%, 95%, or 99% sequence identity to SEQ ID NOs: 1, 9, 17 and 25; and a light chain variable region having at least 80%, 85%, 90%, 95% or 99% sequence identity to SEQ ID NOs: 2, 10, 18 and 26. In some embodiments, the engineered antigen binding domain comprises a heavy chain variable region comprising an amino acid sequence of SEQ ID NO: 1 and a light chain variable region comprising an amino acid sequence of SEQ ID NO: 2. In some embodiments, the engineered effector cell further comprises a stalk region, a transmembrane domain, at least one costimulatory domains, and a signaling domain. In some embodiments, the at least one costimulatory signaling domain comprises CD8, CD27, CD28z, 4-1BB, ICOS, OX40 or fragment or combination thereof. In some embodiments, the at least one costimulatory signaling domain comprises CD28 and 4-1BB or fragments thereof. In some embodiments, the at least one costimulatory signaling domain comprises CD28 or fragment thereof. In some embodiments, a first costimulatory signaling domain is encoded by a first vector and a second costimulatory signaling domain is encoded by a second vector. In some embodiments, the engineered effector cell is prepared from an autologous effector cell. In some embodiments, the engineered effector cell is prepared from an allogeneic effector cell. In some embodiments, the engineered effector cell is a CAR-T cell. In some embodiments, the engineered effector cell is a CAR-NK cell.

Disclosed herein, in certain embodiments, is a pharmaceutical composition comprising an engineered effector cell described above; and an excipient.

Disclosed herein, in certain embodiments, is a method of treating a subject having a cancer characterized by an overexpression of CD46, comprising administering to the subject a pharmaceutical composition comprising a plurality of engineered effector cells, wherein each engineered effector cell comprises an engineered antigen binding domain that binds to an epitope of CD46, and wherein the engineered antigen binding domain is displayed on the surface of the engineered effector cell. In some embodiments, the engineered effector cell is an engineered T cell. In some embodiments, the engineered effector cell is an engineered natural killer T cell. In some embodiments, the engineered effector cell is an engineered natural killer cell. In some embodiments, the engineered antigen binding domain comprises Fab, Fab', F(ab')$_2$, scFv, sc(Fv)$_2$, dsFv, diabody or binding fragments thereof. In some embodiments, the engineered antigen binding domain comprises scFv. In some embodiments, the engineered antigen binding domain binds to an epitope of CD46 bound by one or more antibodies selected from SEQ ID NOs: 1, 2, 9, 10, 17, 18, 25, 26, 33, 34, 41, 42, 49, 50, 57, 58, 65, 66, 73, 74, 81, 82, 89, 90, 97, 98, 105, 106, 113, 114, 121, 122, 129, 130, 137, 138, 145, 146, 153, 154, 161, 162, 169, 170, 177, 178, 185, 186, 193 or 194. In some embodiments, the engineered antigen binding domain comprises a heavy chain variable region comprising three complementarity determining regions (CDRs) and a light chain variable region comprising three CDRs, wherein the heavy chain variable region comprises (i) a variable heavy (VH) CDR1 that has an amino acid sequence of SEQ ID NO: 3, (ii) a variable heavy (VH) CDR2 that has an amino acid sequence of SEQ ID NO: 4, and (iii) a variable heavy (VH) CDR3 that has an amino acid sequence of SEQ ID NO: 5, and wherein the light chain variable region comprises (iv) a variable light (VL) CDR 1 that has an amino acid sequence of SEQ ID NO: 6, (v) a variable light (VL) CDR 2 that has an amino acid sequence of SEQ ID NO: 7, and (vi) a variable light (VL) CDR 3 that has an amino acid sequence of SEQ ID NO: 8. In some embodiments, the engineered antigen binding domain comprises a heavy chain variable region comprising three complementarity determining regions (CDRs) and a light chain variable region comprising three CDRs, wherein the heavy chain variable region comprises (i) a variable heavy (VH) CDR1 that has an amino acid sequence of SEQ ID NO: 11, (ii) a variable heavy (VH) CDR2 that has an amino acid sequence of SEQ ID NO: 12, and (iii) a variable heavy (VH) CDR3 that has an amino acid sequence of SEQ ID NO: 13, and wherein the light chain variable region comprises (iv) a variable light (VL) CDR 1 that has an amino acid sequence of SEQ ID NO: 14, (v) a variable light (VL) CDR 2 that has an amino acid sequence of SEQ ID NO: 15, and (vi) a variable light (VL) CDR 3 that has an amino acid sequence of SEQ ID NO: 16. In some embodiments, the engineered antigen binding domain comprises a heavy chain variable region comprising three complementarity determining regions (CDRs) and a light chain variable region comprising three CDRs, wherein the heavy chain variable region comprises (i) a variable heavy (VH) CDR1 that has an amino acid sequence of SEQ ID NO: 19, (ii) a variable heavy (VH) CDR2 that has an amino acid sequence of SEQ ID NO: 20, and (iii) a variable heavy (VH) CDR3 that has an amino acid sequence of SEQ ID NO: 21, and wherein the light chain variable region comprises (iv) a variable light (VL) CDR 1 that has an amino acid sequence of SEQ ID NO: 22, (v) a variable light (VL) CDR 2 that has an amino acid sequence of SEQ ID NO: 23, and (vi) a variable light (VL) CDR 3 that has an amino acid sequence of SEQ ID NO: 24. In some embodiments, the engineered antigen binding domain comprises a heavy chain variable region comprising three complementarity determining regions (CDRs) and a light chain variable region comprising three CDRs, wherein the heavy chain variable region comprises (i) a variable heavy (VH) CDR1 that has an amino acid sequence of SEQ ID NO: 27, (ii) a variable heavy (VH) CDR2 that has an amino acid sequence of SEQ ID NO: 28, and (iii) a variable heavy (VH) CDR3 that has an amino acid sequence of SEQ ID NO: 29, and wherein the light chain variable region comprises (iv) a variable light (VL) CDR 1 that has an amino acid sequence of SEQ ID NO: 30, (v) a variable light (VL) CDR 2 that has an amino acid sequence of SEQ ID NO: 31, and (vi) a variable light (VL) CDR 3 that has an amino acid sequence of SEQ ID NO: 32. In some embodiments, the engineered antigen binding domain comprises a heavy chain variable region having at least 80%, 85%, 90%, 95%, or 99% sequence identity to SEQ ID NOs: 1, 9, 17 and 25; and a light chain variable region having at least 80%, 85%, 90%, 95% or 99% sequence identity to SEQ ID NOs: 2, 10, 18 and 26. In some embodiments, the engineered antigen binding domain comprises a heavy chain variable region comprising an amino acid sequence of SEQ ID NO: 1 and a light chain variable region comprising an amino acid sequence of SEQ ID NO: 2. In some embodiments, the engineered effector cell further comprises a stalk region, a transmembrane domain, at least one costimulatory domains, and a signaling domain. In some embodiments, the at least one costimulatory signaling domain comprises CD8, CD27, CD28z, 4-1BB, ICOS, OX40 or fragment or combination thereof. In some embodiments, the at least one costimulatory signaling domain comprises CD28 and 4-1BB or fragments thereof. In some embodiments, the at least one costimulatory signaling domain comprises CD28 or fragment thereof. In some embodiments, a first costimulatory signaling domain is encoded by a first vector and a second costimulatory signaling domain is encoded by a second vector. In some embodiments, the engineered effector cell is prepared from an autologous effector cell. In some embodiments, the engineered effector cell is prepared from an allogeneic effector cell. In some embodiments, the CAR effector cell is a CAR-T cell. In some embodiments, the CAR effector cell is a CAR-NK cell. In some embodiments, the cancer comprises breast cancer, cervical cancer, colorectal cancer, kidney cancer, liver cancer, lung cancer, ovarian cancer, pancreatic cancer, prostate cancer or urothelial cancer. In some embodiments, the cancer comprises mesothelioma, lymphoma, or leukemia. In some embodiments, the cancer is prostate cancer. In some embodiments, the cancer is multiple myeloma. In some embodiments, the pharmaceutical composition further comprises an excipient. In some embodiments, the method further comprises an additional therapeutic agent. In some embodiments, the additional therapeutic agent comprises a cytokine. In some embodiments, the cytokine comprises IL2, IL7, IL12, IL15, IL21, IFNγ or TNF-α. In some embodiments, the additional therapeutic agent comprises chemotherapeutic agent. In some embodiments, the chemotherapeutic agent is selected from among bortezomib, CAL-101, chlorambucil, cyclophosphamide, dexamethasone, docetaxel, doxorubicin, endostatin, everolimus, fludarabine, fostamatinib, ifosfamide, ibritumomab, lenalidomide, mesalazine, ofatumumab, paclitaxel, pentostatin, prednisone, rituximab, temsirolimus, thalidomide, tositumomab or a combination thereof. In some embodiments, the engineered effector cell and the additional therapeutic agent is administered sequentially. In some embodiments, the engineered effector cell is administered after administering the additional therapeutic agent. In some embodiments, the additional therapeutic agent comprises cyclophosphamide and optionally further comprising fludarabine. In some embodiments, the additional therapeutic agent is administered to induce lymphopenia. In some embodiments, the pharmaceutical composition is formulated for parenteral administration. In some embodiments, the pharmaceutical composition is administered to the subject as an injection. In some embodiments, the pharmaceutical composition is administered to the subject as an infusion. In some embodiments, the subject is a human.

Disclosed herein, in certain embodiments, is a method of treating a subject having a cancer characterized by an overexpression of CD46, comprising administering to the subject a pharmaceutical composition comprising a plurality of chimeric antigen receptor (CAR) effector cells, wherein each CAR effector cell recognizes an epitope recognized by an antibody of SEQ ID NOs: 1, 2, 9, 10, 17, 18, 25, 26, 33, 34, 41, 42, 49, 50, 57, 58, 65, 66, 73, 74, 81, 82, 89, 90, 97, 98, 105, 106, 113, 114, 121, 122, 129, 130, 137, 138, 145, 146, 153, 154, 161, 162, 169, 170, 177, 178, 185, 186, 193 or 194.

Disclosed herein, in certain embodiments, is a method of depleting CD46 overexpressed cells, comprising (a) contacting an effector cell ex vivo with a vector comprising a polynucleotide encoding an engineered antigen binding domain that recognizes an epitope of CD46 to generate a CD46-specific effector cell, wherein the engineered antigen binding domain is displayed on the surface of the CD46-specific effector cell; and (b) administering the CD46-specific effector cell to a subject having CD46 overexpressed cells, thereby depleting the population of CD46 overexpressed cells. In some embodiments, the CD46 overexpressed cells are cancer cells. In some embodiments, the cancer cells comprise breast cancer cells, cervical cancer cells, colorectal cancer cells, kidney cancer cells, liver cancer cells, lung cancer cells, ovarian cancer cells, pancreatic cancer cells, prostate cancer cells or urothelial cancer cells. In some embodiments, the cancer cells comprise cells from mesothelioma, cells from lymphoma, or cells from leukemia. In some embodiments, the cancer cells comprise prostate cancer cells. In some embodiments, the cancer cells comprise cells from multiple myeloma. In some embodiments, the engineered effector cell is an engineered T cell. In some embodiments, the engineered effector cell is an engineered natural killer T cell. In some embodiments, the engineered effector cell is an engineered natural killer cell. In some embodiments, the engineered antigen binding domain comprises Fab, Fab', F(ab')$_2$, scFv, sc(Fv)$_2$, dsFv, diabody or binding fragments thereof. In some embodiments, the engineered antigen binding domain comprises scFv. In some embodiments, the engineered antigen binding domain comprises a heavy chain variable region comprising three complementarity determining regions (CDRs) and a light chain variable region comprising three CDRs, wherein the heavy chain variable region comprises (i) a variable heavy (VH) CDR1 that has an amino acid sequence of SEQ ID NO: 3, (ii) a variable heavy (VH) CDR2 that has an amino acid sequence of SEQ ID NO: 4, and (iii) a variable heavy (VH) CDR3 that has an amino acid sequence of SEQ ID NO: 5, and wherein the light chain variable region comprises (iv) a variable light (VL) CDR 1 that has an amino acid sequence of SEQ ID NO: 6, (v) a variable light (VL) CDR 2 that has an amino acid sequence of SEQ ID NO: 7, and (vi) a variable light (VL) CDR 3 that has an amino acid sequence of SEQ ID NO: 8. In some embodiments, the engineered antigen binding domain comprises a heavy chain variable region comprising three complementarity determining regions (CDRs) and a light chain variable region comprising three CDRs, wherein the heavy chain variable region comprises (i) a variable heavy (VH) CDR1 that has an amino acid sequence of SEQ ID NO: 11, (ii) a variable heavy (VH) CDR2 that has an amino acid sequence of SEQ ID NO: 12, and (iii) a variable heavy (VH) CDR3 that has an amino acid sequence of SEQ ID NO: 13, and wherein the light chain variable region comprises (iv) a variable light (VL) CDR 1 that has an amino acid sequence of SEQ ID NO: 14, (v) a variable light (VL) CDR 2 that has an amino acid sequence of SEQ ID NO: 15, and (vi) a variable light (VL) CDR 3 that has an amino acid sequence of SEQ ID NO: 16. In some embodiments, the engineered antigen binding domain comprises a heavy chain variable region comprising three complementarity determining regions (CDRs) and a light chain variable region comprising three CDRs, wherein the heavy chain variable region comprises (i) a variable heavy (VH) CDR1 that has an amino acid sequence of SEQ ID NO: 19, (ii) a variable heavy (VH) CDR2 that has an amino acid sequence of SEQ ID NO: 20, and (iii) a variable heavy (VH) CDR3 that has an amino acid sequence of SEQ ID NO: 21, and wherein the light chain variable region comprises (iv) a variable light (VL) CDR 1 that has an amino acid sequence of SEQ ID NO: 22, (v) a variable light (VL) CDR 2 that has an amino acid sequence of SEQ ID NO: 23, and (vi) a variable light (VL) CDR 3 that has an amino acid sequence of SEQ ID NO: 24. In some embodiments, the engineered antigen binding domain comprises a heavy chain variable region comprising three complementarity determining regions (CDRs) and a light chain variable region comprising three CDRs, wherein the heavy chain variable region comprises (i) a variable heavy (VH) CDR1 that has an amino acid sequence of SEQ ID NO: 27, (ii) a variable heavy (VH) CDR2 that has an amino acid sequence of SEQ ID NO: 28, and (iii) a variable heavy (VH) CDR3 that has an amino acid sequence of SEQ ID NO: 29, and wherein the light chain variable region comprises (iv) a variable light (VL) CDR 1 that has an amino acid sequence of SEQ ID NO: 30, (v) a variable light (VL) CDR 2 that has an amino acid sequence of SEQ ID NO: 31, and (vi) a variable light (VL) CDR 3 that has an amino acid sequence of SEQ ID NO: 32. In some embodiments, the engineered antigen binding domain comprises a heavy chain variable region having at least 80%, 85%, 90%, 95%, or 99% sequence identity to SEQ ID NOs: 1, 9, 17 and 25; and a light chain variable region having at least 80%, 85%, 90%, 95% or 99% sequence identity to SEQ ID NOs: 2, 10, 18 and 26. In some embodiments, the engineered antigen binding domain comprises a heavy chain variable region comprising an amino acid sequence of SEQ ID NO: 1 and a light chain variable region comprising an amino acid sequence of SEQ ID NO: 2. In some embodiments, the engineered effector cell further comprises a stalk region, a transmembrane domain, at least one costimulatory domains, and a signaling domain. In some embodiments, the at least one costimulatory signaling domain comprises CD8, CD27, CD28z, 4-1BB, ICOS, OX40 or fragment or combination thereof. In some embodiments, the at least one costimulatory signaling domain comprises CD28 and 4-1BB or fragments thereof. In some embodiments, the at least one costimulatory signaling domain comprises CD28 or fragment thereof. In some embodiments, a first costimulatory signaling domain is encoded by a first vector and a second costimulatory signaling domain is encoded by a second vector. In some embodiments, the engineered effector cell is prepared from an autologous effector cell. In some embodiments, the engineered effector cell is prepared from an allogeneic effector cell. In some embodiments, the CAR effector cell is a CAR-T cell. In some embodiments, the CAR effector cell is a CAR-NK cell. In some embodiments, the vector is a viral vector. In some embodiments, the vector is a non-viral vector.

Disclosed herein, in certain embodiments, is a method of depleting CD46 overexpressed cells, comprising (a) contacting a T cell ex vivo with a vector comprising a polynucleotide encoding an engineered antigen binding domain that recognizes an epitope of CD46 to generate a CD46-specific CAR-T cell, wherein the engineered antigen binding domain is displayed on the surface of the CD46-specific CAR-T cell; and (b) administering the CD46-specific CAR-T cell to a subject having CD46 overexpressed cells, thereby depleting the population of CD46 overexpressed cells.

Disclosed herein, in certain embodiments, is chimeric polynucleotide comprising a first polynucleotide segment encoding an antigen binding domain that binds to an epitope of CD46; and a second polynucleotide segment encoding a polypeptide comprising a stalk region, a transmembrane domain, at least one costimulatory domains, and a signaling domain; wherein the chimeric polynucleotide, upon transfection to an effector cell, expresses the CD46 antigen binding domain and the polypeptide as a continuous chain, and wherein expression of the CD46 antigen binding domain and the polypeptide triggers the effector cell to activate and/or proliferate.

Disclosed herein, in certain embodiments, is a vector comprising a chimeric polynucleotide comprising a first polynucleotide segment encoding an antigen binding domain that binds to an epitope of CD46; and a second polynucleotide segment encoding a polypeptide comprising a stalk region, a transmembrane domain, at least one costimulatory domains, and a signaling domain; wherein the chimeric polynucleotide, upon transfection to an effector cell, expresses the CD46 antigen binding domain and the polypeptide as a continuous chain, and wherein expression of the CD46 antigen binding domain and the polypeptide triggers the effector cell to activate and/or proliferate.

Disclosed herein, in certain embodiments, is a polynucleotide encoding a chimeric receptor comprising an antigen binding domain that binds to an epitope of CD46, a stalk region, a transmembrane domain, at least one costimulatory domains, and a signaling domain.

Disclosed herein, in certain embodiments, is a vector comprising a polynucleotide encoding a chimeric receptor comprising an antigen binding domain that binds to an epitope of CD46, a stalk region, a transmembrane domain, at least one costimulatory domains, and a signaling domain.

Disclosed herein, in certain embodiments, is an engineered single-chain polypeptide comprising an antigen binding domain that binds to an epitope of CD46, a stalk region, a transmembrane domain, at least one costimulatory domains, and a signaling domain.

Disclosed herein, in certain embodiments, is a vector comprising a polynucleotide encoding an engineered single-chain polypeptide comprising an antigen binding domain that binds to an epitope of CD46, a stalk region, a transmembrane domain, at least one costimulatory domains, and a signaling domain.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
FIG. 1 illustrates a schematic of a CAR cassette. "6xHis" is disclosed as SEQ ID NO: 204.

CD46, also known as CD46 complement regulatory protein, cluster of differentiation 46 and membrane cofactor protein, is an inhibitory complement receptor. Overexpression of CD46 has been observed in several cancers, such as breast cancer, colorectal cancer, liver cancer, lung cancer, or prostate cancer. In some cases, overexpression of CD46 has been characterized as a negative prognostic factor. For example, overexpression of CD46 has been correlated with shorter progression-free time and shorter overall survival time in breast cancer patients and ovarian cancer patients.

Chimeric antigen receptor (CAR) therapy comprises reprogramming of endogenous effector cells to target specific tumor antigens. In some instance, CAR therapy targeting CD19, a pan-B cell antigen present in most B cell leukemias and lymphomas, has shown efficacy in several clinical trials, for example, targeting acute lymphoblastic leukemia (ALL), chronic lymphocytic leukemia (CLL), or B-cell non-Hodgkin lymphoma (NHL).

In some embodiments, described herein are engineered effector cells and compositions comprising engineered effector cells. In some instances, also described herein include methods of targeting tumor antigen CD46 for treatment of a cancer characterized with an overexpression of CD46 or methods of depleting a cell with an overexpression of CD46.

In some cases, engineered effector cells binds specifically to CD46, and comprises an engineered antigen binding domain that binds to an epitope of CD46, wherein the engineered antigen binding domain is displayed on the surface of the engineered effector cell. In some embodiments, an engineered effector cell described herein comprises an engineered extracellular antigen recognition domain. In some instances, an engineered effector cell described herein further comprises a trans-membrane domain and at least one signaling region that controls engineered effector cell activation, generating a chimeric antigen receptor (CAR) architecture. In some embodiments, the at least one signaling region further comprises one or more co-stimulatory domains.

Disclosed herein, in certain embodiments, are engineered effector cells comprising an engineered antigen binding domain that specifically binds to CD46. In some embodiments, the engineered effector cell is an engineered T cell, an engineered natural killer T cell, an engineered natural killer cell, or an engineered chimeric antigen receptor (CAR). In some embodiments, the engineered CAR is an engineered CAR-T. In some embodiments, the engineered CAR is an engineered CAR-NK.

Engineered Antigen Binding Domain

In some embodiments, an engineered effector cell described herein comprises an engineered extracellular antigen binding domain. In some instances, an antigen binding domain is displayed on the surface of the effector cell. In other instances, an antigen binding domain is displayed near the surface or at a distal point away from the surface of the effector cell (e.g., for enhanced interaction with a target receptor). In some embodiments, an engineered antigen binding domain described herein is joined through a stalk region and a transmembrane domain to an intracellular signaling domain of the engineered effector cell.

In some embodiments, an engineered antigen binding domain described herein comprises a humanized antibody or binding fragment thereof, murine antibody or binding fragment thereof, chimeric antibody or binding fragment thereof, monoclonal antibody or binding fragment thereof, monovalent Fab', divalent Fab2, single-chain variable fragment (scFv), bis-scFv, (scFv)2, diabody, minibody, nanobody, triabody, tetrabody, disulfide stabilized Fv protein (dsFv), single-domain antibody (sdAb), Ig NAR, camelid antibody or binding fragment thereof. In some embodiments, the engineered antigen binding domain comprises Fab, Fab', F(ab')$_2$, scFv, sc(Fv)$_2$, dsFv, diabody or binding fragments thereof. In some embodiments, the engineered antigen binding domain comprises Fab, Fab', F(ab')$_2$, scFv, sc(Fv)$_2$ or binding fragments thereof. In some embodiments, the engineered antigen binding domain comprises a scFv.

In some embodiments, the engineered antigen binding domain binds to an epitope of CD46 bound by one or more antibodies selected from SEQ ID NOs: 1, 2, 9, 10, 17, 18, 25, 26, 33, 34, 41, 42, 49, 50, 57, 58, 65, 66, 73, 74, 81, 82, 89, 90, 97, 98, 105, 106, 113, 114, 121, 122, 129, 130, 137, 138, 145, 146, 153, 154, 161, 162, 169, 170, 177, 178, 185, 186, 193 or 194. In some embodiments, the engineered antigen binding domain binds to an epitope of CD46 bound by one or more antibodies selected from SEQ ID NOs: 1, 2, 9, 10, 17, 18, 25 or 26. In some embodiments, the engineered antigen binding domain binds to an epitope of CD46 bound by one or more antibodies selected from SEQ ID NOs: 33, 34, 41, 42, 49, 50, 57, 58, 65, 66, 73, 74, 81, 82, 89, 90, 97, 98, 105, 106, 113, 114, 121, 122, 129, 130, 137, 138, 145, 146, 153, 154, 161, 162, 169, 170, 177, 178, 185, 186, 193 or 194.

In some cases, the anti-CD46 antibody binds to at least a portion of sushi domain 1 of CD46 comprising the amino acid sequence KPYYEIGERVDYKCKKGYFYIPPLATHTICDR (SEQ ID NO: 201).

Antibody YS5 and Variants

In some embodiments, an engineered antigen binding domain described herein comprises a heavy chain variable region comprising three complementarity determining regions (CDRs) and a light chain variable region comprising three CDRs, wherein the heavy chain variable region comprises a variable heavy chain (VH) CDR1 that has an amino acid sequence of SEQ ID NO: 3, a variable heavy chain (VH) CDR2 that has an amino acid sequence of SEQ ID NO: 4, a variable heavy chain (VH) CDR3 that has an amino acid sequence of SEQ ID NO: 5, and wherein the light chain variable region comprises a variable light chain (VL) CDR1 that has an amino acid sequence of SEQ ID NO: 6, a variable light chain (VL) CDR2 that has an amino acid sequence of SEQ ID NO: 7, and a variable light chain (VL) CDR3 that has an amino acid sequence of SEQ ID NO: 8.

In some embodiments, an engineered antigen binding domain described herein comprises a heavy chain variable region having at least 80%, 85%, 90%, 95%, or 99% sequence identity to SEQ ID NO. 1. In some embodiments, an engineered antigen binding domain described herein comprises a heavy chain variable region having at least 80% sequence identity to SEQ ID NO: 1. In some embodiments, an engineered antigen binding domain described herein comprises a heavy chain variable region having at least 85% sequence identity to SEQ ID NO: 1. In some embodiments, an engineered antigen binding domain described herein comprises a heavy chain variable region having at least 90% sequence identity to SEQ ID NO: 1. In some embodiments, an engineered antigen binding domain described herein comprises a heavy chain variable region having at least 95% sequence identity to SEQ ID NO: 1. In some embodiments, an engineered antigen binding domain described herein comprises a heavy chain variable region having at least 99% sequence identity to SEQ ID NO: 1.

In some embodiments, an engineered antigen binding domain described herein comprises a light chain variable region having at least 80%, 85%, 90%, 95%, or 99% sequence identity to SEQ ID NO: 2. In some embodiments, an engineered antigen binding domain described herein comprises a light chain variable region having at least 80% sequence identity to SEQ ID NO: 2. In some embodiments, an engineered antigen binding domain described herein comprises a light chain variable region having at least 85% sequence identity to SEQ ID NO: 2. In some embodiments, an engineered antigen binding domain described herein comprises a light chain variable region having at least 90% sequence identity to SEQ ID NO: 2. In some embodiments, an engineered antigen binding domain described herein comprises a light chain variable region having at least 95% sequence identity to SEQ ID NO: 2. In some embodiments, an engineered antigen binding domain described herein comprises a light chain variable region having at least 99% sequence identity to SEQ ID NO: 2.

In some embodiments, an engineered antigen binding domain described herein comprises a heavy chain variable region of SEQ ID NO: 1 and a light chain variable region of SEQ ID NO: 2.

In some embodiments, an engineered antigen binding domain described herein comprises an antibody of SEQ ID NO: 203.

Antibody YS12 and Variants

In some embodiments, an engineered antigen binding domain described herein comprises a heavy chain variable region comprising three complementarity determining regions (CDRs) and a light chain variable region comprising three CDRs, wherein the heavy chain variable region comprises a variable heavy chain (VH) CDR1 that has an amino acid sequence of SEQ ID NO: 11, a variable heavy chain (VH) CDR2 that has an amino acid sequence of SEQ ID NO: 12, a variable heavy chain (VH) CDR3 that has an amino acid sequence of SEQ ID NO: 13, and wherein the light chain variable region comprises a variable light chain (VL) CDR1 that has an amino acid sequence of SEQ ID NO: 14, a variable light chain (VL) CDR2 that has an amino acid sequence of SEQ ID NO: 15, and a variable light chain (VL) CDR3 that has an amino acid sequence of SEQ ID NO: 16.

In some embodiments, an engineered antigen binding domain described herein comprises a heavy chain variable region having at least 80%, 85%, 90%, 95%, or 99% sequence identity to SEQ ID NO: 9. In some embodiments, an engineered antigen binding domain described herein comprises a heavy chain variable region having at least 80% sequence identity to SEQ ID NO: 9. In some embodiments, an engineered antigen binding domain described herein comprises a heavy chain variable region having at least 85% sequence identity to SEQ ID NO: 9. In some embodiments, an engineered antigen binding domain described herein comprises a heavy chain variable region having at least 90% sequence identity to SEQ ID NO: 9. In some embodiments, an engineered antigen binding domain described herein comprises a heavy chain variable region having at least 95% sequence identity to SEQ ID NO: 9. In some embodiments, an engineered antigen binding domain described herein comprises a heavy chain variable region having at least 99% sequence identity to SEQ ID NO: 9.

In some embodiments, an engineered antigen binding domain described herein comprises a light chain variable region having at least 80%, 85%, 90%, 95%, or 99% sequence identity to SEQ ID NO: 10. In some embodiments, an engineered antigen binding domain described herein comprises a light chain variable region having at least 80% sequence identity to SEQ ID NO: 10. In some embodiments, an engineered antigen binding domain described herein comprises a light chain variable region having at least 85% sequence identity to SEQ ID NO: 10. In some embodiments, an engineered antigen binding domain described herein comprises a light chain variable region having at least 90% sequence identity to SEQ ID NO: 10. In some embodiments, an engineered antigen binding domain described herein comprises a light chain variable region having at least 95% sequence identity to SEQ ID NO: 10. In some embodiments, an engineered antigen binding domain described herein comprises a light chain variable region having at least 99% sequence identity to SEQ ID NO: 10.

In some embodiments, an engineered antigen binding domain described herein comprises a heavy chain variable region of SEQ ID NO: 9 and a light chain variable region of SEQ ID NO: 10.

Antibody YS5iVD and Variants

In some embodiments, an engineered antigen binding domain described herein comprises a heavy chain variable region comprising three complementarity determining regions (CDRs) and a light chain variable region comprising three CDRs, wherein the heavy chain variable region comprises a variable heavy chain (VH) CDR1 that has an amino acid sequence of SEQ ID NO: 19, a variable heavy chain (VH) CDR2 that has an amino acid sequence of SEQ ID NO: 20, a variable heavy chain (VH) CDR3 that has an amino acid sequence of SEQ ID NO: 21, and wherein the light chain variable region comprises a variable light chain (VL) CDR1 that has an amino acid sequence of SEQ ID NO: 22, a variable light chain (VL) CDR2 that has an amino acid sequence of SEQ ID NO: 23, and a variable light chain (VL) CDR3 that has an amino acid sequence of SEQ ID NO: 24.

In some embodiments, an engineered antigen binding domain described herein comprises a heavy chain variable region having at least 80%, 85%, 90%, 95%, or 99% sequence identity to SEQ ID NO: 17. In some embodiments, an engineered antigen binding domain described herein comprises a heavy chain variable region having at least 80% sequence identity to SEQ ID NO: 17. In some embodiments, an engineered antigen binding domain described herein comprises a heavy chain variable region having at least 85% sequence identity to SEQ ID NO: 17. In some embodiments, an engineered antigen binding domain described herein comprises a heavy chain variable region having at least 90% sequence identity to SEQ ID NO: 17. In some embodiments, an engineered antigen binding domain described herein comprises a heavy chain variable region having at least 95% sequence identity to SEQ ID NO: 17. In some embodiments, an engineered antigen binding domain described herein comprises a heavy chain variable region having at least 99% sequence identity to SEQ ID NO: 17.

In some embodiments, an engineered antigen binding domain described herein comprises a light chain variable region having at least 80%, 85%, 90%, 95%, or 99% sequence identity to SEQ ID NO: 18. In some embodiments, an engineered antigen binding domain described herein comprises a light chain variable region having at least 80% sequence identity to SEQ ID NO: 18. In some embodiments, an engineered antigen binding domain described herein comprises a light chain variable region having at least 85% sequence identity to SEQ ID NO: 18. In some embodiments, an engineered antigen binding domain described herein comprises a light chain variable region having at least 90% sequence identity to SEQ ID NO: 18. In some embodiments, an engineered antigen binding domain described herein comprises a light chain variable region having at least 95% sequence identity to SEQ ID NO: 18. In some embodiments, an engineered antigen binding domain described herein comprises a light chain variable region having at least 99% sequence identity to SEQ ID NO: 18.

In some embodiments, an engineered antigen binding domain described herein comprises a heavy chain variable region of SEQ ID NO: 17 and a light chain variable region of SEQ ID NO: 18.

Antibody SB1HGNY and Variants

In some embodiments, an engineered antigen binding domain described herein comprises a heavy chain variable region comprising three complementarity determining regions (CDRs) and a light chain variable region comprising three CDRs, wherein the heavy chain variable region comprises a variable heavy chain (VH) CDR1 that has an amino acid sequence of SEQ ID NO: 27, a variable heavy chain (VH) CDR2 that has an amino acid sequence of SEQ ID NO: 28, a variable heavy chain (VH) CDR3 that has an amino acid sequence of SEQ ID NO: 29, and wherein the light chain variable region comprises a variable light chain (VL) CDR1 that has an amino acid sequence of SEQ ID NO: 30, a variable light chain (VL) CDR2 that has an amino acid sequence of SEQ ID NO: 31, and a variable light chain (VL) CDR3 that has an amino acid sequence of SEQ ID NO: 32.

In some embodiments, an engineered antigen binding domain described herein comprises a heavy chain variable region having at least 80%, 85%, 90%, 95%, or 99% sequence identity to SEQ ID NO: 25. In some embodiments, an engineered antigen binding domain described herein comprises a heavy chain variable region having at least 80% sequence identity to SEQ ID NO: 25. In some embodiments, an engineered antigen binding domain described herein comprises a heavy chain variable region having at least 85% sequence identity to SEQ ID NO: 25. In some embodiments, an engineered antigen binding domain described herein comprises a heavy chain variable region having at least 90% sequence identity to SEQ ID NO: 25. In some embodiments, an engineered antigen binding domain described herein comprises a heavy chain variable region having at least 95% sequence identity to SEQ ID NO: 25. In some embodiments, an engineered antigen binding domain described herein comprises a heavy chain variable region having at least 99% sequence identity to SEQ ID NO: 25.

In some embodiments, an engineered antigen binding domain described herein comprises a light chain variable region having at least 80%, 85%, 90%, 95%, or 99% sequence identity to SEQ ID NO: 26. In some embodiments, an engineered antigen binding domain described herein comprises a light chain variable region having at least 80% sequence identity to SEQ ID NO: 26. In some embodiments, an engineered antigen binding domain described herein comprises a light chain variable region having at least 85% sequence identity to SEQ ID NO: 26. In some embodiments, an engineered antigen binding domain described herein comprises a light chain variable region having at least 90% sequence identity to SEQ ID NO: 26. In some embodiments, an engineered antigen binding domain described herein comprises a light chain variable region having at least 95% sequence identity to SEQ ID NO: 26. In some embodiments, an engineered antigen binding domain described herein comprises a light chain variable region having at least 99% sequence identity to SEQ ID NO: 26.

In some embodiments, an engineered antigen binding domain described herein comprises a heavy chain variable region of SEQ ID NO: 25 and a light chain variable region of SEQ ID NO: 26.

In some embodiments, the engineered effector cell described herein comprises a sequence selected from Table 1.

TABLE 1

| Identifier | Sequence | SEQ ID NO: |
|---|---|---|
| YS5, VH | QVQLVQSGGGVVQPGRSLRLACAASGLTVNNYAMHWVR QAPGKGLEWVAVISYDGNNKYYADSVKGRFTISRDNSK NTLYLQMNSLRAEDTAVYYCAKGGGYFDLWGRGTLVTV SS | 1 |
| YS5, VL | QSVLTQPPSVSGAPGQRVTISCTGSSSNIGAGYDVHWY QQLPGTAPKLLIYGNNNRPSGVPDRFSGSKSGTSASLA ITGLQAEDEADYYCSSYTSGTWLFGGGTKLTVL | 2 |
| YS5, VH CDR1 | GLTVNNYA | 3 |
| YS5, VH CDR2 | ISYDGNNK | 4 |
| YS5, VH CDR3 | AKGGGYFDL | 5 |
| YS5, VL CDR1 | SSNIGAGYD | 6 |
| YS5, VL CDR2 | GNN | 7 |
| YS5, VL CDR3 | SSYTSGTWL | 8 |
| YS12, VH | QVQLVESGGGVVQPGRSLRLSCAASGFTFSTYGMHWVR QAPGKGLEWLSFISYDGDEKYYADSVKGRFTISRDNSK NTLYLQMNSLRAEDTAVYWCAKASGYGMGILDYWGQGT LVTVSS | 9 |
| YS12, VL | SSELTQDPAVSVALGQTVRITCQGDSLRSYYVSWFQQK PGQAPVFVMYGQNNRPSGISERFSGSSSGNTASLIITG AQAEDEADYYCHSRDSSGTHLRVFGGGTKLTVL | 10 |
| YS12, VH CDR1 | GFTFSTYG | 11 |
| YS12, VH CDR2 | FISYDGDEK | 12 |
| YS12, VH CDR3 | AKASGYGMGILDY | 13 |
| YS12, VL CDR1 | SLRSYY | 14 |
| YS12, VL CDR2 | GQN | 15 |
| YS12, VL CDR3 | HSRDSSGTHLRV | 16 |
| YS5vID, VH | QVQLVQSGGGVVQPGRSLRLACAASGFTVNNYAMHWVR QAPGKGLEWVAVISYDGNNKYYADSVKGRFTISRDNSK NTLYLQMNSLRAEDTAVYYCAKGGGYFDLWGRGTLVTV SS | 17 |
| YS5vID, VL | QSVLTQPPSVSGAPGQRVTISCTGSSSNIGAGYDVHWY QQLPGTAPKLLIYGDNNRPSGVPDRFSGSKSGTSASLA ITGLQAEDEADYYCSSYTSGTWLFGGGTKLTVL | 18 |
| YS5vID, VH CDR1 | GFTVNNYA | 19 |
| YS5vID, VH CDR2 | ISYDGNNK | 20 |
| YS5vID, VH CDR3 | AKGGGYFDL | 21 |
| YS5vID, VL CDR1 | SSNIGAGYD | 22 |
| YS5vID, VL CDR2 | GDN | 23 |
| YS5vID, VL CDR3 | SSYTSGTWL | 24 |

TABLE 1-continued

| Identifier | Sequence | SEQ ID NO: |
|---|---|---|
| SB1HGNY, VH | QVQLQQSGGGVVQPGRSLRLSCAASGFTFSSYAMHWVRQAPGKGLEWVAFIRSDGSKKYYADSVKGRFTISRDNSKNTLYLQMNSLRAEDTAVYYCARHGNYFDSWGQGTLVTVSS | 25 |
| SB1HGNY, VL | DIQMTQSPSFLSASVGDRVTITCRASQGISSYLAWYQQKPGKAPKLLIYAASTLQSGVPSSFSGSGSGTEFTLTISSLQPEDFATYYCQQLASYPLTFGGGTKVDIK | 26 |
| SB1HGNY, VH CDR1 | GFTFSSYA | 27 |
| SB1HGNY, VH CDR2 | IRSDGSKK | 28 |
| SB1HGNY, VH CDR3 | ARHGNYFDS | 29 |
| SB1HGNY, VL CDR1 | QGISSY | 30 |
| SB1HGNY, CV LDR2 | AAS | 31 |
| SB1HGNY, VL CDR3 | QQLASYPLT | 32 |

In some embodiments, the engineered effector cell described herein comprises a sequence selected from Table 2.

TABLE 2

| Identifier | Sequence | Variable chain SEQ ID NO: | CDR1 SEQ ID NO*: | CDR2 SEQ ID NO*: | CDR3 SEQ ID NO*: |
|---|---|---|---|---|---|
| YS5F, VH | QVQLVQSGGGVVQPGRSLRLACAASGFTVNNYAMHWVRQAPGKGLEWVAVISYDGNNKYYADSVKGRFTISRDNSKNTLYLQMNSLRAEDTAVYYCAKGGGYFDLWGRGTLVTVSS | 33 | 35 | 36 | 37 |
| YS5F, VL | QSVLTQPPSVSGAPGQRVTISCTGSSSNIGAGYDVHWYQQLPGTAPKLLIYGNNRPSGVPDRFSGSKSGTSASLAITGLQAEDEADYYCSSYTSGTWLFGGGTKLTVL | 34 | 38 | 39 | 40 |
| 3G7RY, VH | EVQLVESGGGLVQPGGSLRLSCAASGFTFSDYYMSWIRQAPGKGLEWVSYISSSGSTIYYADSVKGRFTISRDNSKNTLYLQMNSLRAEDTAVYYCARDYGRIAAAGRRYWGQGTLVTVSS | 41 | 43 | 44 | 45 |
| 3G7RY, VL | QSALTQPPSASATPGQRVTISCSGRTSNIGSNHVYWYQQLPGTAPKLLIYRNNQRPSGVPDRFSGSKSGTSASLAISGLRSEDEADYYCATWDDSLSGEVFGGGTKLTVL | 42 | 46 | 47 | 48 |
| YS6, VH | QVQLQESGGGVVRPGGSLRLSCAASGFTFSDYYMSWIRQAPGKGLEWVSYISSSGSTIYYADSVKGRFTISRDNSKNTLYLQMNSLRAEDTAVYYCARDYGRIAAAGRHYWGQGTLVTVSS | 49 | 51 | 52 | 53 |
| YS6, VL | SSELTQDPAVSVALGQTVRITCQGDSLRSYYASWYQQKPGQAPVLVIYGKNNRPSGIPDRFSGSSSGNTASLTITGAQAEDEADYYCNSRDSSGTHLEVFGGGTKVTVL | 50 | 54 | 55 | 56 |
| YS1, VH | EVQLVESGGGLVQPGGSLRLSCAASGFTFSDYYMSWIRQAPGKGLEWVSYISSSGSTIYYADSVKGRFTISRDNSKNTLYLQMNSLRAEDTAVYYCARDYGRIAAAGRHYWGQGTLVTVSS | 57 | 59 | 60 | 61 |
| YS1, VL | SSELTQDPAVSVALGQTVRITCQGDTLSTYYANWYQQKPGQAPVLVIYGKNNRPSGIPDRFSGSSSGNTASLTITGAQAEDEADYYCHSRDISGNYLFASGTKLTVL | 58 | 62 | 63 | 64 |
| YS3, VH | QVQLQESGGGLVQPGGSLRLSCAASGFTFSSYWMSWVRQAPGKGLEWVADIKQDGSEKYYVDSVKGRFTISGDNAKNSLYLQMNSLRAEDTAVYYCAKDVGSTAINYVRAYTWFDPWGQGTLVTVSS | 65 | 67 | 68 | 69 |
| YS3, VL | QSVLTQPPSASGTPGQRVTISCSGSSSNIGSNTVNWSRQLPGTAPKLLIYSNNQRPSGVPDRFSGSKSGTSASLAISGLQSEDEADYYCAAWDDSLNVYVFGTGTKVTVL | 66 | 70 | 71 | 72 |
| YS4, VH | QVQLQESGGGLVQPGGSLRLSCAASGFTFSNYAMSWVRQAPGKGLEWVSTISGSGSSTFYVDSVKGRFTISRDNSKNTLYLQMNSLRAEDTAVYYCAQGLYSSGWANWFDPRGQGTLVTVSS | 73 | 75 | 76 | 77 |
| YS4, VL | KIVLTQSPSSLSASVGDTVTIACRASRDIRNDLAWYQQKPGKAPKLLIYGASSLQSGVPSRFSGSGSGTEFILTISSLQPEDFATYYCHRLNSYPLTFGGGTKVDIK | 74 | 78 | 79 | 80 |
| YS8, VH | QVQLQESGGGVVQPGRSLRLSCAASGFTFSSYGMHWVRQAPGKGLEWVAVISYDGSNKYYADSVKGRFTISRDNSKNTLYLQMNSLRAEDTAVYYCAKVMGLAAAGLDAFDIWGQGTTVTVSS | 81 | 83 | 84 | 85 |
| YS8, VL | NFMLTQPASLSGSPGQSITISCTGTSSDVGGYNYVSWYQQHPGYAPKLMIYDVSNRPSGVSNRFSGSKSGNTASLTISGLQAEDEADYYCSSYTSSSTPWVFGGGTKLTVL | 82 | 86 | 87 | 88 |
| YS7, VH | QVQLVQSGGGVVQPGRSLRLSCAASGFTFSSYAMHWVRQAPGKGLEWVAVISYDGSNKYYADSVKGRFTISRDTSTNTLYLQMNSLRADDTAVYYCGRESSGSPGVWGQGTTVTVSS | 89 | 91 | 92 | 93 |
| YS7, VL | SYVLTQDPAVSVALGQTVRITCQGDSLRSYYASWYQQKPGQAPVLVIYGKNNRPSGIPDRFSGSSSGNTASLTITGAQAEDEADYYCNSRDSSGNQFGGGTKLTVL | 90 | 94 | 95 | 96 |

TABLE 2-continued

| Identifier | Sequence | Variable chain SEQ ID NO: | CDR1 SEQ ID NO*: | CDR2 SEQ ID NO*: | CDR3 SEQ ID NO*: |
|---|---|---|---|---|---|
| YS9, VH | QVQLVESGGGLIQPGGSLRLSCA ASGFTVSSNYMSWVRQAPGKGLE WVS<u>VIYTDGSTYYADSVKGRFTI SRDNSKNTLYLQMNSLRAEDTAI YYCARDRGTSGYDWAWFDLWGQG TLVTVSS</u> | 97 | 99 | 100 | 101 |
| YS9, VL | SSELTQDPAVSVALGQTVRITCQ GD<u>SLRTYYASWYQQRPGQAPILV LYGKNNRPSGIPDRFSGSSSGNT ASLTITGAQAEDEADYYCNSRDS SGNHVVFGGGTKLTVL</u> | 98 | 102 | 103 | 104 |
| YS10, VH | QVQLQESGGGLVQPGGSLRLSCA ASGFTFSSYAMSWVRQAPGKGLE WVS<u>AISGSGGSTYYADSVKGRFT ISRDNSKNTLYMQMNSLRAEDTA VYYCAKDRYYYGSGKDAFDIWGR GTMVTVSS</u> | 105 | 107 | 108 | 109 |
| YS10, VL | QSVLTQPASVSGSPGQSITISCT GTGSDVGSYNYVSWYQQNPGKAP KLMIYEVSNRPSGVSNRFSGSKS GNTASLTISGLQAEDEADYYCSS YTTSSTLVFGGGTKVTVL | 106 | 110 | 111 | 112 |
| YS11, VH | QVQLVESGGGLVQPGGSLGLSCA ASGFTFSNYWMSWVRQAPGKGLE WVA<u>NVRQDGGQKYYVDSVKGRFT ISRDNAKNSLYLQMNSLRTEDTA VYFCVSQRNSGEHDYWGQGTLVT VSS</u> | 113 | 115 | 116 | 117 |
| YS11, VL | SELTQDPAVSVALGQTVRITCQG D<u>SLRSYYASWYQQKPGQAPVLVI YGENSRPSGIPDRFSGSSSGNTA SLTITGAQAEDEADYYCNSWDSS GNHVVFGGGTKLTVL</u> | 114 | 118 | 119 | 120 |
| 3G7HY, VH | EVQLVESGGGLVQPGGSLRLSCA ASGFTFSDYYMSWIRQAPGKGLE WVS<u>YISSSGSTIYYADSVKGRFT ISRDNSKNTLYLQMNSLRAEDTA VYYCARDYGRIAAAGRHYWGQGT LVTVSS</u> | 121 | 123 | 124 | 125 |
| 3G7HY, VL | AIRMTQSPSSLSASVGDRVTITC RAS<u>QSISSYLNWYQQKPGKAPKL LIYAASSLQSGVPSRFSGSGSGT DFTLTISSLQPEDFATYYCQQSY STPRTFGQGTKLEIK</u> | 122 | 126 | 127 | 128 |
| 3G7NY, VH | EVQLVESGGGLVQPGGSLRLSCA ASGFTFSDYYMSWIRQAPGKGLE WVS<u>YISSSGSTIYYADSVKGRFT ISRDNSKNTLYLQMNSLRAEDTA VYYCARDYGRIAAAGRNYWGQGT LVTVSS</u> | 129 | 131 | 132 | 133 |
| 3G7NY, VL | DIVMTQSPLSLPVTPGEPASISC RSS<u>QSLLHSNGYDLDWYLQKPG QSPQLLIYLGSNRASGVPDRFSG SGSGTDFTLKISRVETEDVGIYY CMQGLQTPSFGQGTKLEIK</u> | 130 | 134 | 135 | 136 |
| 3G7, VH | QVQLQESGGGVVRPGGSLRLSCA ASGFTFSDYYMSWIRQAPGKGLE WVS<u>YISSSGSTIYYADSVKGRFT ISRDNSKNTLYLQMNSLRAEDTA VYYCARDYGRIAAAGRHYWGQGT LVTVSS</u> | 137 | 139 | 140 | 141 |
| 3G7, VL | SSELTQDPAVSVALGQTVRITCQ GD<u>SLRSYYASWYQQKPGQAPVPV IYGKNNRPSGIPDRFSGSSSGNT ASLTITGAQAEDEADYYCNSRDS SSTHRGVFGGGTKLTVL</u> | 138 | 142 | 143 | 144 |
| SB2, VH | EVQLVESGGGLVKPGGSLRLSCA ASGFTFSDYYMSWIRQAPGKGLE WVS<u>YISSSGSSIYYADSVKGRFT ISRDNAKNSLYLQMNSLKAEDTA VYYCARDITDVVGVSFDYWGQGT LVTVSS</u> | 145 | 147 | 148 | 149 |
| SB2, VL | DIQLTQSPSSLSASVGDRVTITC RAS<u>RSISTYLSWYQQKPGKAPKL LIYDASRLQNGVPSRFSGSGSDT DFTLTISSLQPEDFATYFCQQSY NPPWTFGQGTKLEIK</u> | 146 | 150 | 151 | 152 |
| 2C8, VH | EVQLVESGGGVVQPGRSLRLSCA ASGFTFSSYGMHWVRQAPGKGLE WVA<u>VISYDGSNKYYADSVKGRFT ISRDNSKNTLYLQMNSLRAEDTA EYYCAKVMGLAAAGLDAFDIWGQ GTLVTVSS</u> | 153 | 155 | 156 | 157 |
| 2C8, VL | QSALTQPASVSGSPGQSITISCT GT<u>SSDVGGYNYVSWYQQHPGKAP KLMIYDVSNRPSGVSNRFSGSKS GNTASLTISGLQAEDEAYYYCSS YTSSSDPWVFGGGTQLTVL</u> | 154 | 158 | 159 | 160 |
| UA8 kappa, VH | EVQLVESGGGVVQPGRSLRLSCA ASGFTFSSFGMHWVRRAPGKGLE WVA<u>VISYDGSNQYYADSVKGRFT ISRDNSKNTLYLQMNSLRAEDTA VYYCGSRPGGGYASGSTVAYWGQ GTLVTVSS</u> | 161 | 163 | 164 | 165 |
| UA8 kappa, VL | NIQMTQSPSSLSASVGDRVTITC RAG<u>QPISTYVNWYQHKPGKAPKL LIYGASNLQSGVPSRFSGGGSAT DFTLTISSLQPEDFATYYCQQSY SSLLTFGDGTKVEIK</u> | 162 | 166 | 167 | 168 |
| 2B10, VH | QVQLQEPGGGLVQPGRSLRLSCA ASGFTFDDYAMHWVRQAPGKGLE WVG<u>RIKSKTDEGTTDYAAPVKGR FSISRDDSKNTLYLQMNSLKTED TGVYYCTATKGLGGSKLGQGTLV TVSS</u> | 169 | 171 | 172 | 173 |
| 2B10, VL | QSVLTQPPSASGTPGQRVTISCS GS<u>SSNIGSNTVSWSRQLPGTAPK LLIYSNDQRPSGVPDRFSGSKSG TSASLAITGLQPEDEADYYCGTW DSSLSAYVFGTGTKLTVL</u> | 170 | 174 | 175 | 176 |
| UA20, VH | QVQLQESGGGLVKPGGSLRLSCA ASGFTFSNAWMNWVRQAPGKGLE WVG<u>RIKSKTDEGTTDYAAPVKGR FSISRDDSKNTLYLQMNSLKTED TGVYYCTATKGLGGSKLGQGTLV TVSS</u> | 177 | 179 | 180 | 181 |
| UA20, VL | QSVLTQPPSASGTPGQRVTISCS GS<u>SSNIGNNTVNWSRQLPGTAPK LLIYSNDQRPSGVPDRFSGSKSG TSASLAITGLQPEDEADYYCGTW DSSLSAYVFGTGTKLTVL</u> | 178 | 182 | 183 | 184 |
| 585II41, | QVQLVESGGGLVQPGGSLRLSCA ASGFTFS<u>SYAMG</u>WVRQAPGKGLE | 185 | 187 | 188 | 189 |

TABLE 2-continued

| Identifier | Sequence | Variable chain SEQ ID NO: | CDR1 SEQ ID NO*: | CDR2 SEQ ID NO*: | CDR3 SEQ ID NO*: |
|---|---|---|---|---|---|
| VH | WVSAISGSGGSTYYADSVKGRFT ISRDNSKDTLYLQMNSLRAEDTA VYYCASRSLLDYWGQGTLVTVSS | | | | |
| 585II41, VL | NFMLTQDPAVSVALGQTVRITCQ GDSLRSYYASWYQQKPGQAPLLV IYGKNNRPSGIPDRFSGSSSGNT ASLTITGAQAEDEADYYCNSRDS SGNPVFGGGTKVTVL | 186 | 190 | 191 | 192 |
| 585II41.1, VH | QVQLVESGGGLVQPGGSLRLSCA ASGFTFSSYAMSWVRQAPGKGLE WVSAISGSGGSTYYADSVKGRFT ISRDNSKDTLYLQMNSLRAEDTA VYYCASRSLLDYWGQGTLVTVSS | 193 | 195 | 196 | 197 |
| 585II41.1 VL | NFMLTQDPAVSVALGQTVRITCQ GDSLRSYYASWYQQKPGQAPLLV IYGKNNRPSGIPDRFSGSSSGNT ASLTITGAQAEDEADYYCNSRDS SGNPVFGGGTKVTVL | 194 | 198 | 199 | 200 |

*CDR1, CDR2, and CDR3 of each of the VH and VL chains are represented by the first, second, and third underlined regions, respectively In some embodiments, an engineered effector cell comprises an antigen binding domain that binds to an epitope bound by antibody 3051.1, G12FC3, M6c42b, 4F3YW, M40pr146, UA8, 585II56, 3076, 3051, M49R, RCI-14, II79_4, II79_3, T5II-4B.1, T5II-4B.2, RCI-11, RCI-20, CI-11A, CI-14A and S95-2. In some embodiments, an engineered effector cell comprises an antibody selected from 3051.1, G12FC3, M6c42b, 4F3YW, M40pr146, UA8, 585II56, 3076, 3051, M49R, RCI-14, II79_4, II79.3, T5II-4B.1, T5II-4B.2, RCI-11, RCI-20, CI-11A, CI-14A and S95-2.

Stalk Region

In some embodiments, an engineered effector cell described herein further comprises a stalk region, also known as a hinge or a spacer. The stalk region is an extracellular component connecting the engineered antigen binding domain to the transmembrane region. In some embodiments, the stalk region provides flexibility to the engineered antigen binding domain. In some embodiments, the length of the stalk region is adjustable. In some embodiments, the engineered effector cell does not comprise a stalk region.

In some cases, a stalk region described herein is derived from an immunoglobulin molecule. In some embodiments, the immunoglobulin molecule comprises IgG1, IgG4, or IgD. In other instances, a stalk region described herein comprises CD3 or CD8. In some cases, the stalk region comprises the CH2CH3 region of an immunoglobulin and optionally portions of CD3. In some cases, the stalk region comprises CD8 (e.g., CD8α).

Transmembrane Domain

In some embodiments, an engineered effector cell described herein further comprises a transmembrane domain. In some embodiments, the transmembrane domain anchors the engineered antigen binding domain to a plasma membrane of the engineered effector cell. In some instances, suitable transmembrane domains include the transmembrane region(s) of alpha, beta or zeta chain of the T-cell receptor; or a transmembrane region from CD28, CD3 epsilon, CD3ζ, CD45, CD4, CD5, CD8alpha, CD9, CD16, CD22, CD33, CD37, CD64, CD80, CD86, CD134, CD137 or CD154. In alternative embodiments, a transmembrane domain is a synthetic transmembrane domain.

In some embodiments, a transmembrane domain comprises a native transmembrane portion of a CD3zeta, CD28, a CD4, or a CD8. In some cases, a transmembrane domain described herein comprises a CD3zeta transmembrane domain. In some cases, a transmembrane domain described herein comprises a CD8 transmembrane domain (e.g., a CD8a transmembrane domain).

Intracellular Signaling Domain

In some embodiments, the engineered effector cell further comprises an intracellular signaling domain. In some embodiments, the intracellular signaling domain is derived from a D3 zeta chain or an FcεRIγ. In some embodiments, the intracellular signaling domain is derived from a CD3zeta chain.

In some embodiments, the signaling domain comprises signaling motifs which are known as immunoreceptor tyrosine-based activation motifs (ITAMs). Examples of ITAM containing cytoplasmic signaling sequences include those derived from TCR zeta, FcR gamma, FcR beta, CD3 gamma, CD3 delta, CD3 epsilon, CD5, CD22, CD79a, CD79b, and CD66d.

In some embodiments, the intracellular signaling domain further comprises at least one co-stimulatory domain. In some embodiments, the at least one co-stimulatory domain is linked to the intracellular signaling domain. In some embodiments, the at least one co-stimulatory domain is linked to a cytoplasmic domain of the CD3 zeta chain. In some embodiments, the co-stimulatory domain provides greater strength of signaling and greater potency to the engineered effector cell.

In some embodiments, illustrative costimulatory domains comprise CD8, CD27, CD28, 4-1BB (CD137), DAP10, OX40 (CD134), ICOS, CD27, NKG2D, Lck, CD70, CD80 or CD86. In some embodiments, an engineered effector cell described herein comprises one or more costimulatory domains, or two or more costimulatory domains selected from CD8, CD27, CD28, 4-1BB (CD137), DAP10, OX40 (CD134), ICOS, CD27, NKG2D, Lck, CD70, CD80, CD86 or a combination thereof. In some cases, an engineered effector cell described herein comprises one or more costimulatory domains, or two or more costimulatory domains selected from CD28, 4-1BB or a combination thereof. In some cases, an engineered effector cell described herein comprises constimulatory domains CD28 and 4-1BB. In some cases, an engineered effector cell described herein comprises constimulatory domains CD28. In some cases, an engineered effector cell described herein comprises constimulatory domains 4-1BB.

Chimeric Antigen Receptor Architectures

In some embodiments, an engineered effector cell described herein comprises a first generation, a second generation, third generation or a fourth generation CAR. In some embodiments, an engineered effector cell described herein comprises a first generation CAR. In some cases, a first generation CAR comprises an antigen binding domain, a stalk region, a transmembrane domain and a signaling domain. In some cases, a co-stimulatory domain is not present within a chimeric antigen receptor (CAR) architecture.

In some embodiments, an engineered effector cell described herein comprises a second generation CAR. In some cases, a second generation CAR comprises an antigen binding domain, a stalk region, a transmembrane domain, a signaling domain and a costimulatory domain.

In some embodiments, an engineered effector cell described herein comprises a third generation CAR. In some cases, the third generation CAR comprises two costimulatory domains in additional to an antigen binding domain, a stalk region and a transmembrane domain. In some embodiments, the two costimulatory domains are engineered in tandem within the chimeric antigen receptor (CAR) architecture.

In some embodiments, an engineered effector cell described herein comprises a fourth generation CAR. In a fourth generation CAR, for example, CAR comprises at least one costimulatory domains and at least one additional cellular component comprising a cytokine transgene or a co-stimulatory ligand. In some instances, the fourth generation CAR comprises at least one costimulatory domain and at least one additional cellular component comprising a co-stimulatory ligand. In some instances, a co-stimulatory ligand comprises CD8, CD27, CD28, 4-1BB (CD137), DAP10, OX40 (CD134), ICOS, CD27, NKG2D, Lck, CD70, CD80, or CD86.

In some embodiments, an engineered effector cell described herein comprises a fourth generation CAR in which the additional cellular component comprises a co-stimulatory ligand. In some cases, the co-stimulatory ligand comprises CD8, CD27, CD28, 4-1BB (CD137), DAP10, OX40 (CD134), ICOS, CD27, NKG2D, Lck, CD70, CD80, or CD86. In some cases, an engineered effector cell described herein comprises a fourth generation CAR in which the additional cellular component comprises a co-stimulatory ligand comprising CD28 or 4-1BB (CD137). In some cases, an engineered effector cell described herein comprises a fourth generation CAR in which the additional cellular component comprises a co-stimulatory ligand comprising CD28. In some cases, an engineered effector cell described herein comprises a fourth generation CAR in which the additional cellular component comprises a co-stimulatory ligand comprising 4-1BB (CD137).

In some embodiments, the fourth generation CAR comprises at least one costimulatory domain and at least one additional cellular component comprising a cytokine transgene. Exemplary cytokines include, but are not limited to, IL2, IL7, IL12, IL15, IL21, IFNγ or TNF-α. In some cases, an engineered effector cell described herein comprises a fourth generation CAR in which the additional cellular component comprises a cytokine transgene. In some cases, an engineered effector cell described herein comprises a fourth generation CAR in which the additional cellular component comprises a cytokine transgene comprising IL2, IL7, IL12, IL15, IL21, IFNγ or TNF-α.

Figure 7:
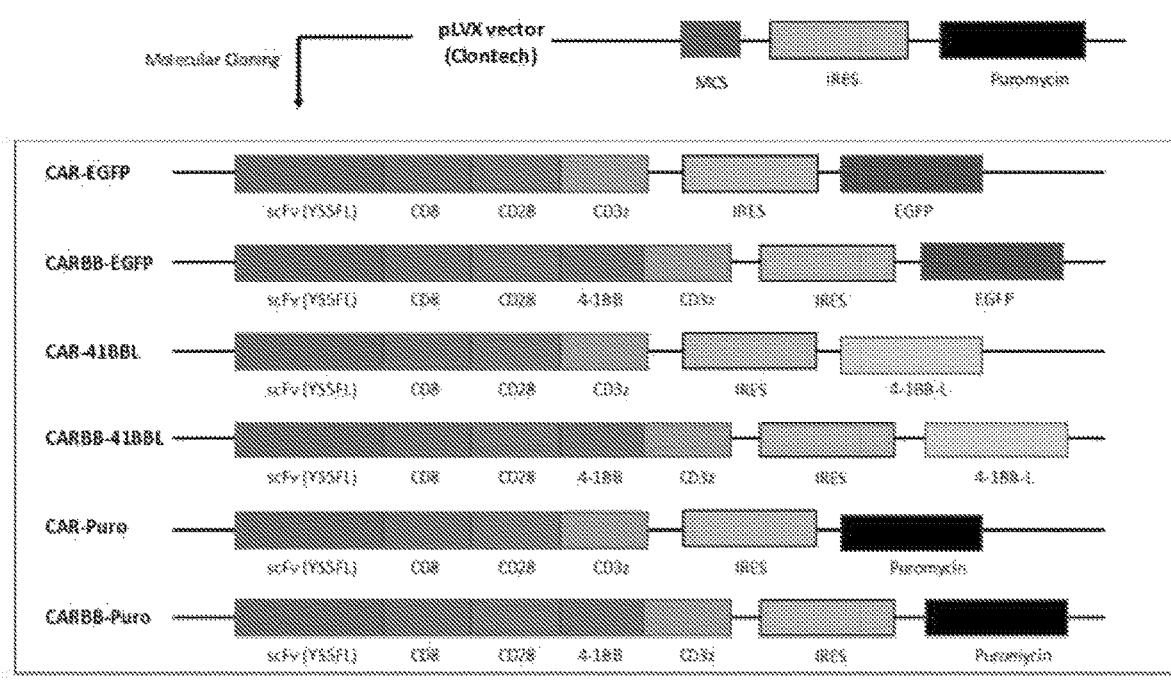
FIG. 7 illustrates six exemplary lentivirus-based CAR-T constructs.
Figure 8A:
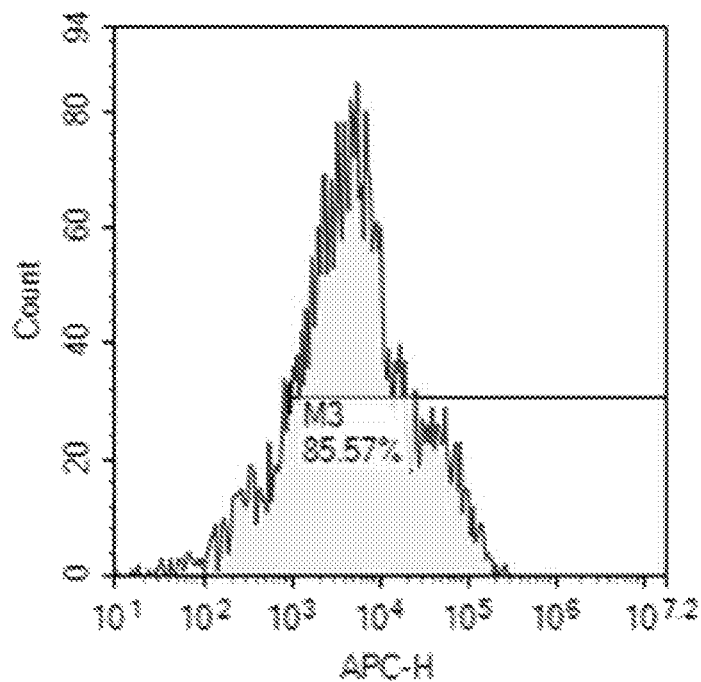
FIG. 8A-FIG. 8G show FACS analysis of CAR expression on T cells on the day of in vitro cytotoxicity assay.
Figure 8B:
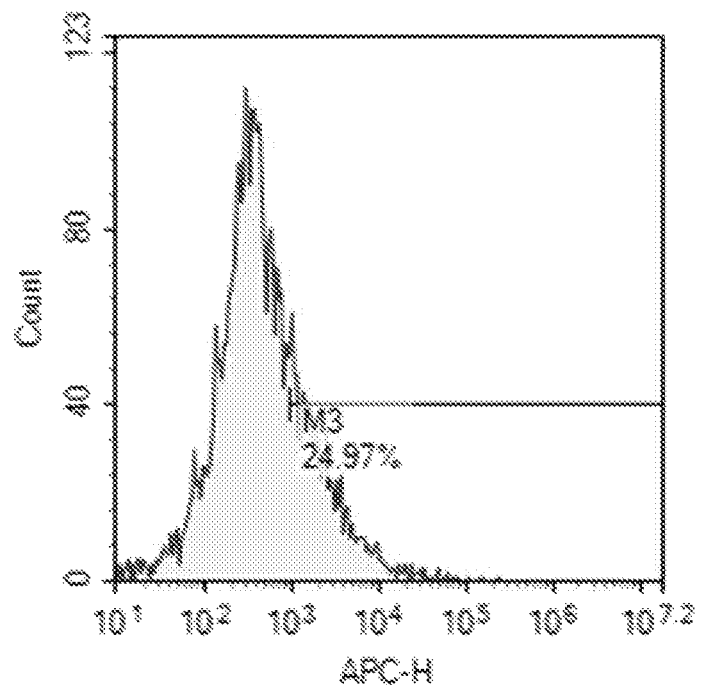
Figure 8C:
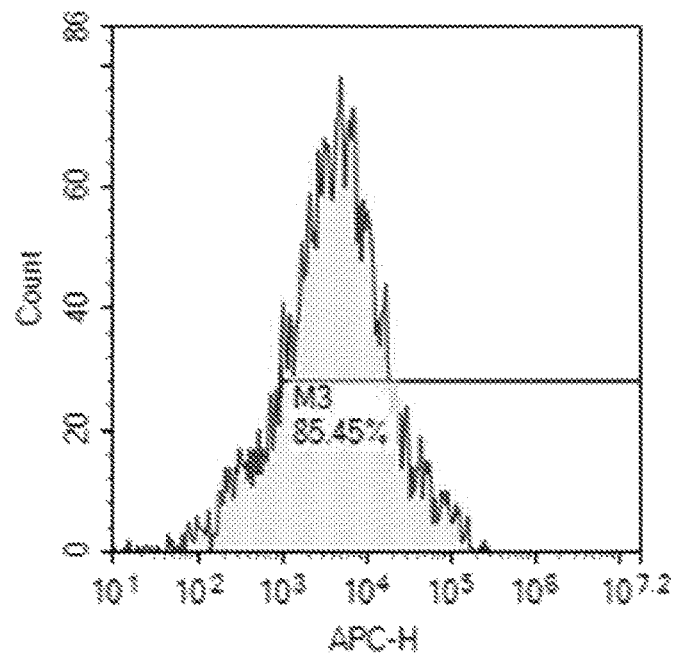
Figure 8D:
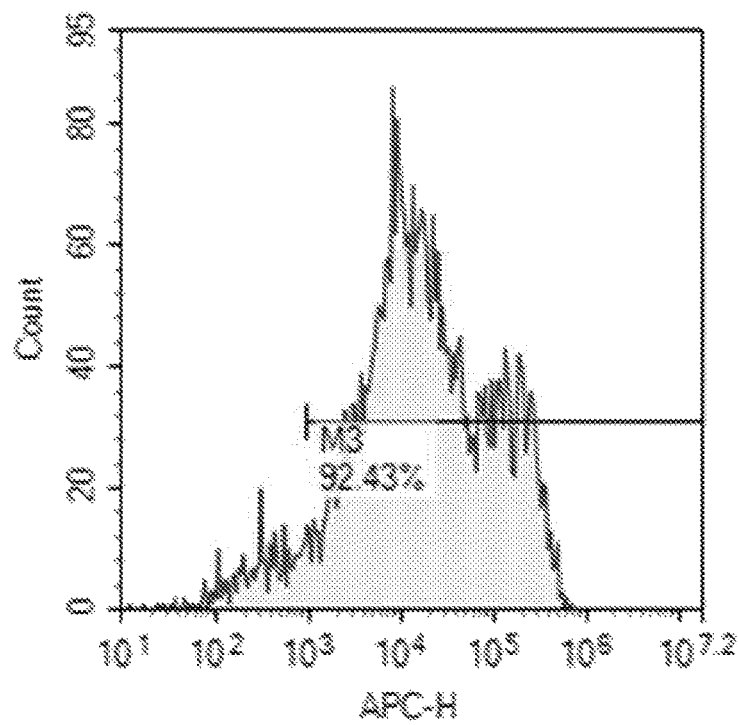
Figure 8E:
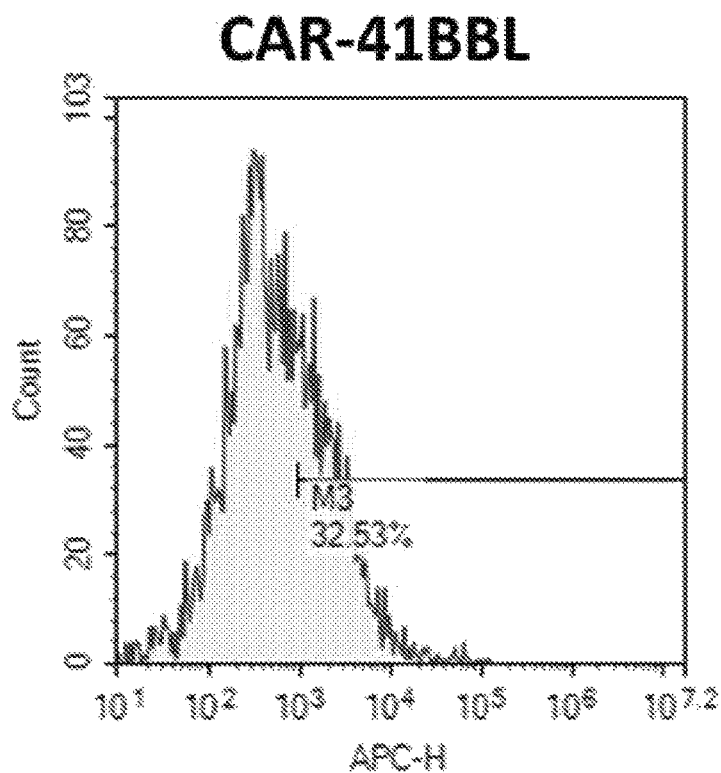
Figure 8F:
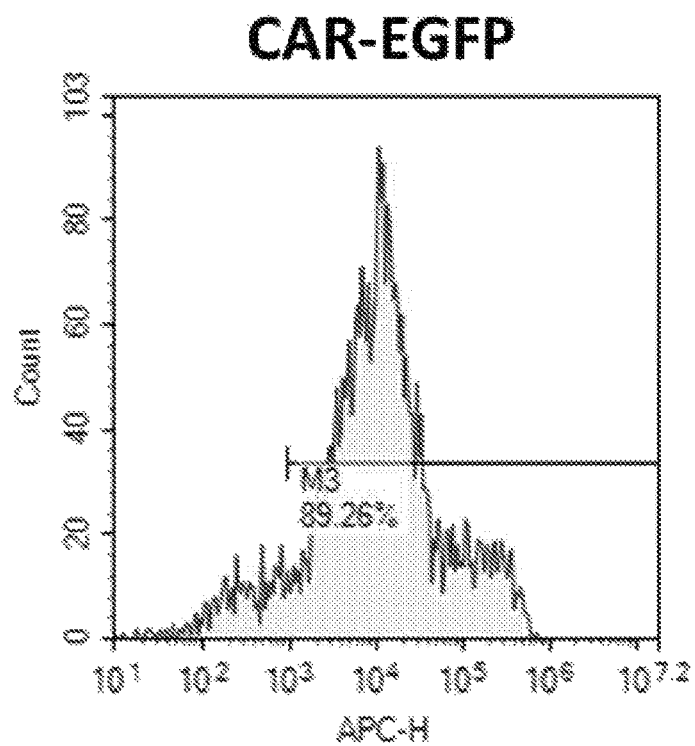
Figure 8G:
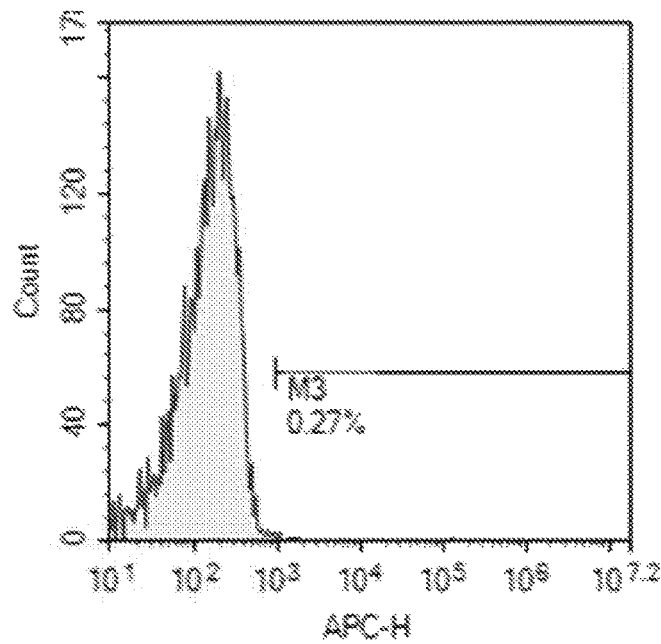
Figure 9A:
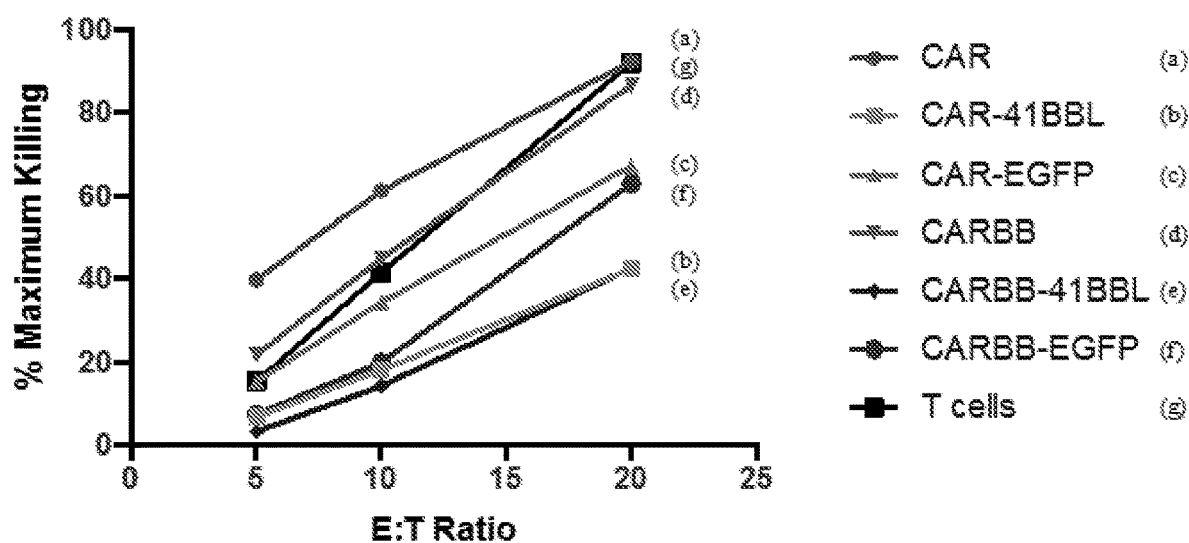
FIG. 9A-FIG. 9D show in vitro cytotoxicity assay on prostate cancer cell lines using six different variants of CAR-T cells targeted to CD46.
Figure 9B:
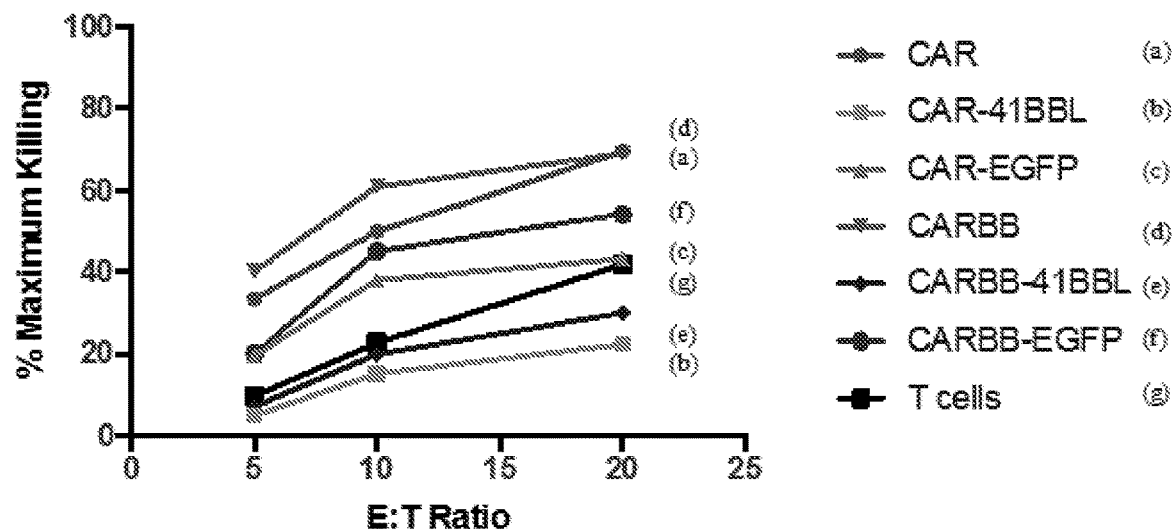
Figure 9C:
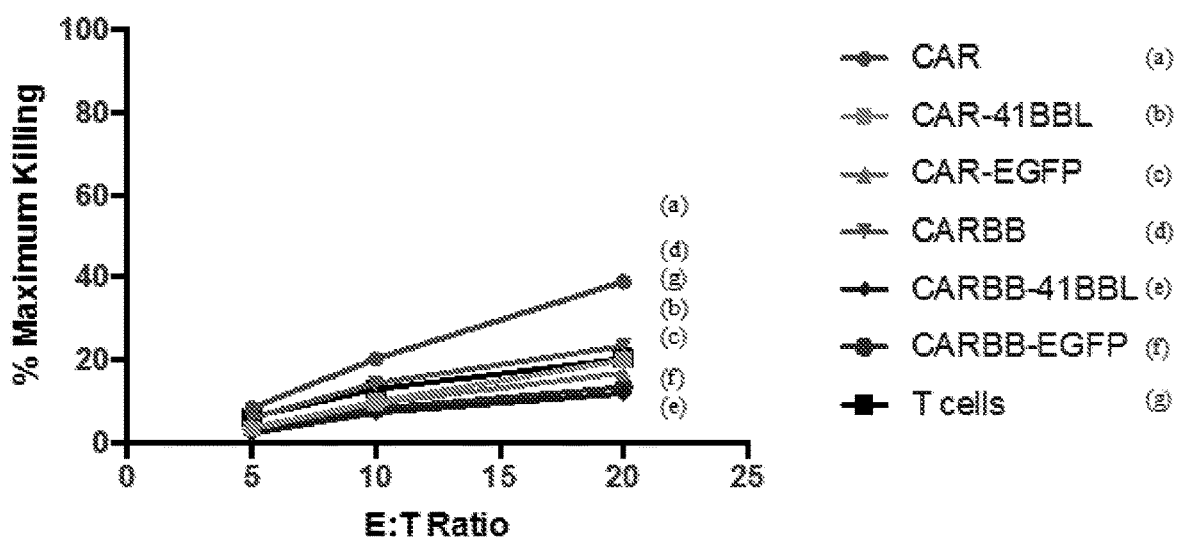
Figure 9D:
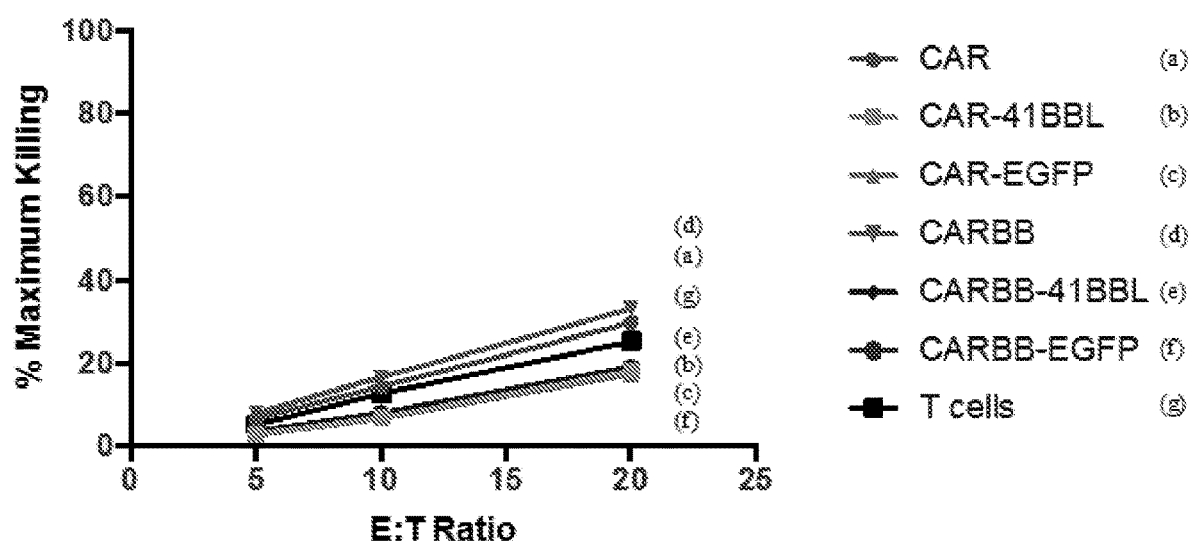

In some embodiments, an engineered effector cell described herein comprises a CAR encoded by a vector as illustrated in FIG. 7.

Engineered Single-Chain Polypeptide

In some embodiments, a chimeric antigen receptor comprises an engineered single-chain polypeptide. In some instances, the engineered single-chain polypeptide comprising an antigen binding domain that binds to an epitope of CD46, a stalk region, a transmembrane domain, at least one costimulatory domains, and a signaling domain.

In some instances, the antigen binding domain comprises Fab, Fab', F(ab')$_2$, scFv, sc(Fv)$_2$, dsFv, diabody or binding fragments thereof. In some cases, the antigen binding domain comprises scFv.

In some embodiments, the antigen binding domain binds to an epitope of CD46 bound by one or more antibodies selected from SEQ ID NOs: 1, 2, 9, 10, 17, 18, 25, 26, 33, 34, 41, 42, 49, 50, 57, 58, 65, 66, 73, 74, 81, 82, 89, 90, 97, 98, 105, 106, 113, 114, 121, 122, 129, 130, 137, 138, 145, 146, 153, 154, 161, 162, 169, 170, 177, 178, 185, 186, 193 or 194.

In some instances, the antigen binding domain comprises a heavy chain variable region comprising three complementarity determining regions (CDRs) and a light chain variable region comprising three CDRs, wherein the heavy chain variable region comprises i) a variable heavy (VH) CDR1 that has an amino acid sequence of SEQ ID NO: 3, ii) a variable heavy (VH) CDR2 that has an amino acid sequence of SEQ ID NO: 4, and iii) a variable heavy (VH) CDR3 that has an amino acid sequence of SEQ ID NO: 5, and wherein the light chain variable region comprises iv) a variable light (VL) CDR 1 that has an amino acid sequence of SEQ ID NO: 6, v) a variable light (VL) CDR 2 that has an amino acid sequence of SEQ ID NO: 7, and vi) a variable light (VL) CDR 3 that has an amino acid sequence of SEQ ID NO: 8.

In some instances, the binding domain comprises a heavy chain variable region comprising three complementarity determining regions (CDRs) and a light chain variable region comprising three CDRs, wherein the heavy chain variable region comprises i) a variable heavy (VH) CDR1 that has an amino acid sequence of SEQ ID NO: 11, ii) a variable heavy (VH) CDR2 that has an amino acid sequence of SEQ ID NO: 12, and iii) a variable heavy (VH) CDR3 that has an amino acid sequence of SEQ ID NO: 13, and wherein the light chain variable region comprises iv) a variable light (VL) CDR 1 that has an amino acid sequence of SEQ ID NO: 14, v) a variable light (VL) CDR 2 that has an amino acid sequence of SEQ ID NO: 15, and vi) a variable light (VL) CDR 3 that has an amino acid sequence of SEQ ID NO: 16.

In some instances, the antigen binding domain comprises a heavy chain variable region comprising three complementarity determining regions (CDRs) and a light chain variable region comprising three CDRs, wherein the heavy chain variable region comprises i) a variable heavy (VH) CDR1 that has an amino acid sequence of SEQ ID NO: 19, ii) a variable heavy (VH) CDR2 that has an amino acid sequence of SEQ ID NO: 20, and iii) a variable heavy (VH) CDR3 that has an amino acid sequence of SEQ ID NO: 21, and wherein the light chain variable region comprises iv) a variable light (VL) CDR 1 that has an amino acid sequence of SEQ ID NO: 22, v) a variable light (VL) CDR 2 that has an amino acid sequence of SEQ ID NO: 23, and vi) a variable light (VL) CDR 3 that has an amino acid sequence of SEQ ID NO: 24.

In some instances, the antigen binding domain comprises a heavy chain variable region comprising three complementarity determining regions (CDRs) and a light chain variable region comprising three CDRs, wherein the heavy chain variable region comprises i) a variable heavy (VH) CDR1 that has an amino acid sequence of SEQ ID NO: 27, ii) a variable heavy (VH) CDR2 that has an amino acid sequence of SEQ ID NO: 28, and iii) a variable heavy (VH) CDR3 that has an amino acid sequence of SEQ ID NO: 29, and wherein the light chain variable region comprises iv) a variable light (VL) CDR 1 that has an amino acid sequence of SEQ ID NO: 30, v) a variable light (VL) CDR 2 that has an amino acid sequence of SEQ ID NO: 31, and vi) a variable light (VL) CDR 3 that has an amino acid sequence of SEQ ID NO: 32.

In some cases, the antigen binding domain comprises a heavy chain variable region having at least 80%, 85%, 90%, 95%, or 99% sequence identity to SEQ ID NOs: 1, 9, 17 and 25; and a light chain variable region having at least 80%, 85%, 90%, 95% or 99% sequence identity to SEQ ID NOs: 2, 10, 18 and 26.

In some cases, the antigen binding domain comprises a heavy chain variable region comprising an amino acid sequence of SEQ ID NO: 1 and a light chain variable region comprising an amino acid sequence of SEQ ID NO: 2.

In some embodiments, the at least one costimulatory signaling domain comprises CD8, CD27, CD28z, 4-1BB, ICOS, OX40, or a fragment or combination thereof. In some instances, the at least one costimulatory signaling domain comprises CD28 and 4-1BB or fragments thereof. In some cases, the at least one costimulatory signaling domain comprises CD28 or fragment thereof.

In some embodiments, the engineered single-chain polypeptide is encoded by a vector and further transfected in an effector cell. In some instances, the transfected effector cell is prepared from an autologous effector cell. In other instances, the transfected effector cell is prepared from an allogeneic effector cell. In some cases, the transfected effector cell is a CAR-T cell. In some cases, the transfected effector cell is a CAR-NK cell.

In some embodiments, the engineered single-chain polypeptide is encoded by a vector as illustrated in FIG. 7.

Polynucleotide Encoding a Chimeric Antigen Receptor

In some embodiments, a chimeric antigen receptor is encoded by a chimeric polynucleotide. In such embodiments, the chimeric polynucleotide comprises a first polynucleotide segment encoding an antigen binding domain that binds to an epitope of CD46; and a second polynucleotide segment encoding a polypeptide comprising a stalk region, a transmembrane domain, at least one costimulatory domains, and a signaling domain; in which the chimeric polynucleotide, upon transfection to an effector cell, expresses the CD46 antigen binding domain and the polypeptide as a continuous chain, and wherein expression of the CD46 antigen binding domain and the polypeptide triggers the effector cell to activate and/or proliferate.

In some instances, the effector cell is a T cell, optionally a natural killer T cell; or a natural killer cell.

In some instances, the first polynucleotide segment encodes Fab, Fab', F(ab')$_2$, scFv, sc(Fv)$_2$, dsFv, diabody or binding fragments thereof. In some cases, the first polynucleotide segment encodes scFv.

In some embodiments, the antigen binding domain binds to an epitope of CD46 bound by one or more antibodies selected from SEQ ID NOs: 1, 2, 9, 10, 17, 18, 25, 26, 33, 34, 41, 42, 49, 50, 57, 58, 65, 66, 73, 74, 81, 82, 89, 90, 97, 98, 105, 106, 113, 114, 121, 122, 129, 130, 137, 138, 145, 146, 153, 154, 161, 162, 169, 170, 177, 178, 185, 186, 193 or 194.

In some instances, the first polynucleotide segment encodes a heavy chain variable region comprising three complementarity determining regions (CDRs) and a light chain variable region comprising three CDRs, wherein the heavy chain variable region comprises i) a variable heavy (VH) CDR1 that has an amino acid sequence of SEQ ID NO: 3, ii) a variable heavy (VH) CDR2 that has an amino acid sequence of SEQ ID NO: 4, and iii) a variable heavy (VH) CDR3 that has an amino acid sequence of SEQ ID NO: 5, and wherein the light chain variable region comprises iv) a variable light (VL) CDR 1 that has an amino acid sequence of SEQ ID NO: 6, v) a variable light (VL) CDR 2 that has an amino acid sequence of SEQ ID NO: 7, and vi) a variable light (VL) CDR 3 that has an amino acid sequence of SEQ ID NO: 8.

In some instances, the first polynucleotide segment encodes a heavy chain variable region comprising three complementarity determining regions (CDRs) and a light chain variable region comprising three CDRs, wherein the heavy chain variable region comprises i) a variable heavy (VH) CDR1 that has an amino acid sequence of SEQ ID NO: 11, ii) a variable heavy (VH) CDR2 that has an amino acid sequence of SEQ ID NO: 12, and iii) a variable heavy (VH) CDR3 that has an amino acid sequence of SEQ ID NO: 13, and wherein the light chain variable region comprises iv) a variable light (VL) CDR 1 that has an amino acid sequence of SEQ ID NO: 14, v) a variable light (VL) CDR 2 that has an amino acid sequence of SEQ ID NO: 15, and vi) a variable light (VL) CDR 3 that has an amino acid sequence of SEQ ID NO: 16.

In some instances, the first polynucleotide segment encodes a heavy chain variable region comprising three complementarity determining regions (CDRs) and a light chain variable region comprising three CDRs, wherein the heavy chain variable region comprises i) a variable heavy (VH) CDR1 that has an amino acid sequence of SEQ ID NO: 19, ii) a variable heavy (VH) CDR2 that has an amino acid sequence of SEQ ID NO: 20, and iii) a variable heavy (VH) CDR3 that has an amino acid sequence of SEQ ID NO: 21, and wherein the light chain variable region comprises iv) a variable light (VL) CDR 1 that has an amino acid sequence of SEQ ID NO: 22, v) a variable light (VL) CDR 2 that has an amino acid sequence of SEQ ID NO: 23, and vi) a variable light (VL) CDR 3 that has an amino acid sequence of SEQ ID NO: 24.

In some instances, the first polynucleotide segment encodes a heavy chain variable region comprising three complementarity determining regions (CDRs) and a light chain variable region comprising three CDRs, wherein the heavy chain variable region comprises i) a variable heavy (VH) CDR1 that has an amino acid sequence of SEQ ID NO: 27, ii) a variable heavy (VH) CDR2 that has an amino acid sequence of SEQ ID NO: 28, and iii) a variable heavy (VH) CDR3 that has an amino acid sequence of SEQ ID NO: 29, and wherein the light chain variable region comprises iv) a variable light (VL) CDR 1 that has an amino acid sequence of SEQ ID NO: 30, v) a variable light (VL) CDR 2 that has an amino acid sequence of SEQ ID NO: 31, and vi) a variable light (VL) CDR 3 that has an amino acid sequence of SEQ ID NO: 32.

In some cases, the first polynucleotide segment encodes a heavy chain variable region having at least 80%, 85%, 90%, 95%, or 99% sequence identity to SEQ ID NOs: 1, 9, 17 and 25; and a light chain variable region having at least 80%, 85%, 90%, 95% or 99% sequence identity to SEQ ID NOs: 2, 10, 18 and 26.

In some cases, the first polynucleotide segment encodes a heavy chain variable region comprising an amino acid sequence of SEQ ID NO: 1 and a light chain variable region comprising an amino acid sequence of SEQ ID NO: 2.

In some embodiments, the at least one costimulatory signaling domain comprises CD8, CD27, CD28z, 4-1BB, ICOS, OX40, or a fragment or combination thereof. In some instances, the at least one costimulatory signaling domain comprises CD28 and 4-1BB or fragments thereof. In some cases, the at least one costimulatory signaling domain comprises CD28 or fragment thereof.

In some embodiments, a vector comprises the chimeric polynucleotide and is further transfected in an effector cell. In some instances, the transfected effector cell is prepared from an autologous effector cell. In other instances, the transfected effector cell is prepared from an allogeneic effector cell. In some cases, the transfected effector cell is a CAR-T cell. In some cases, the transfected effector cell is a CAR-NK cell.

In some embodiments, the transfected effector cell has MHC non-restricted antibody-type specificity.

In some embodiments, a polynucleotide described herein encodes a chimeric receptor comprising an antigen binding domain that binds to an epitope of CD46, a stalk region, a transmembrane domain, at least one costimulatory domains, and a signaling domain.

In such instances, the antigen binding domain comprises Fab, Fab', F(ab')$_2$, scFv, sc(Fv)$_2$, dsFv, diabody or binding fragments thereof. In some cases, the antigen binding domain comprises scFv.

In some embodiments, the antigen binding domain binds to an epitope of CD46 bound by one or more antibodies selected from SEQ ID NOs: 1, 2, 9, 10, 17, 18, 25, 26, 33, 34, 41, 42, 49, 50, 57, 58, 65, 66, 73, 74, 81, 82, 89, 90, 97, 98, 105, 106, 113, 114, 121, 122, 129, 130, 137, 138, 145, 146, 153, 154, 161, 162, 169, 170, 177, 178, 185, 186, 193 or 194.

In some instances, the antigen binding domain comprises a heavy chain variable region comprising three complementarity determining regions (CDRs) and a light chain variable region comprising three CDRs, wherein the heavy chain variable region comprises i) a variable heavy (VH) CDR1 that has an amino acid sequence of SEQ ID NO: 3, ii) a variable heavy (VH) CDR2 that has an amino acid sequence of SEQ ID NO: 4, and iii) a variable heavy (VH) CDR3 that has an amino acid sequence of SEQ ID NO: 5, and wherein the light chain variable region comprises iv) a variable light (VL) CDR 1 that has an amino acid sequence of SEQ ID NO: 6, v) a variable light (VL) CDR 2 that has an amino acid sequence of SEQ ID NO: 7, and vi) a variable light (VL) CDR 3 that has an amino acid sequence of SEQ ID NO: 8.

In some instances, the binding domain comprises a heavy chain variable region comprising three complementarity determining regions (CDRs) and a light chain variable region comprising three CDRs, wherein the heavy chain variable region comprises i) a variable heavy (VH) CDR1 that has an amino acid sequence of SEQ ID NO: 11, ii) a variable heavy (VH) CDR2 that has an amino acid sequence of SEQ ID NO: 12, and iii) a variable heavy (VH) CDR3 that has an amino acid sequence of SEQ ID NO: 13, and wherein the light chain variable region comprises iv) a variable light (VL) CDR 1 that has an amino acid sequence of SEQ ID NO: 14, v) a variable light (VL) CDR 2 that has an amino acid sequence of SEQ ID NO: 15, and vi) a variable light (VL) CDR 3 that has an amino acid sequence of SEQ ID NO: 16.

In some instances, the antigen binding domain comprises a heavy chain variable region comprising three complementarity determining regions (CDRs) and a light chain variable region comprising three CDRs, wherein the heavy chain variable region comprises i) a variable heavy (VH) CDR1 that has an amino acid sequence of SEQ ID NO: 19, ii) a variable heavy (VH) CDR2 that has an amino acid sequence of SEQ ID NO: 20, and iii) a variable heavy (VH) CDR3 that has an amino acid sequence of SEQ ID NO: 21, and wherein the light chain variable region comprises iv) a variable light (VL) CDR 1 that has an amino acid sequence of SEQ ID NO: 22, v) a variable light (VL) CDR 2 that has an amino acid sequence of SEQ ID NO: 23, and vi) a variable light (VL) CDR 3 that has an amino acid sequence of SEQ ID NO: 24.

In some instances, the antigen binding domain comprises a heavy chain variable region comprising three complementarity determining regions (CDRs) and a light chain variable region comprising three CDRs, wherein the heavy chain variable region comprises i) a variable heavy (VH) CDR1 that has an amino acid sequence of SEQ ID NO: 27, ii) a variable heavy (VH) CDR2 that has an amino acid sequence of SEQ ID NO: 28, and iii) a variable heavy (VH) CDR3 that has an amino acid sequence of SEQ ID NO: 29, and wherein the light chain variable region comprises iv) a variable light (VL) CDR 1 that has an amino acid sequence of SEQ ID NO: 30, v) a variable light (VL) CDR 2 that has an amino acid sequence of SEQ ID NO: 31, and vi) a variable light (VL) CDR 3 that has an amino acid sequence of SEQ ID NO: 32.

In some cases, the antigen binding domain comprises a heavy chain variable region having at least 80%, 85%, 90%, 95%, or 99% sequence identity to SEQ ID NOs: 1, 9, 17 and 25; and a light chain variable region having at least 80%, 85%, 90%, 95% or 99% sequence identity to SEQ ID NOs: 2, 10, 18 and 26.

In some cases, the antigen binding domain comprises a heavy chain variable region comprising an amino acid sequence of SEQ ID NO: 1 and a light chain variable region comprising an amino acid sequence of SEQ ID NO: 2.

In some embodiments, the at least one costimulatory signaling domain comprises CD8, CD27, CD28z, 4-1BB, ICOS, OX40, or a fragment or combination thereof. In some instances, the at least one costimulatory signaling domain comprises CD28 and 4-1BB or fragments thereof. In some cases, the at least one costimulatory signaling domain comprises CD28 or fragment thereof.

In some embodiments, a vector comprises the polynucleotide that encodes a chimeric receptor and is further transfected in an effector cell. In some instances, the transfected effector cell is prepared from an autologous effector cell. In other instances, the transfected effector cell is prepared from an allogeneic effector cell. In some cases, the transfected effector cell is a CAR-T cell. In some cases, the transfected effector cell is a CAR-NK cell.

In some embodiments, a vector comprising a polynucleotide described above is as illustrated in FIG. 7.

Methods of Use

In certain embodiments, described herein are methods of treating a subject having a cancer characterized by an overexpression of CD46 and methods of depleting CD46 overexpressed population of cells in a subject with an engineered effector cell described supra. In some embodiments, disclosed herein are methods of treating a subject having a cancer characterized by an overexpression of CD46, which comprises administering to the subject a pharmaceutical composition comprising a plurality of engineered effector cells, wherein each engineered effector cell comprises an engineered antigen binding domain that binds to an epitope of CD46, and wherein the engineered antigen binding domain is displayed on the surface of the engineered effector cell. In some instances, also described herein are methods of treating a subject having a cancer characterized by overexpression of CD46, which comprises administering to the subject a pharmaceutical composition comprising a plurality of chimeric antigen receptor (CAR) effector cells, wherein each CAR effector cell recognizes an epitope by an antibody of SEQ ID NOs: 1, 2, 9, 10, 17, 18, 25, 26, 33, 34, 41, 42, 49, 50, 57, 58, 65, 66, 73, 74, 81, 82, 89, 90, 97, 98, 105, 106, 113, 114, 121, 122, 129, 130, 137, 138, 145, 146, 153, 154, 161, 162, 169, 170, 177, 178, 185, 186, 193 or 194.

In some embodiments, a cancer characterized by an overexpression of CD46 comprises breast cancer, cervical cancer, colorectal cancer, kidney cancer, liver cancer, lung cancer, ovarian cancer, pancreatic cancer, prostate cancer, or urothelial cancer. In some instances, a cancer characterized by an overexpression of CD46 comprises breast cancer, liver cancer, lung cancer, ovarian cancer or prostate cancer. In some cases, a cancer characterized by an overexpression of CD46 comprises breast cancer, ovarian cancer or prostate cancer. In some cases, the cancer characterized by an overexpression of CD46 is a relapsed or refractory cancer (e.g., a relapsed or refractory breast cancer, cervical cancer, colorectal cancer, kidney cancer, liver cancer, lung cancer, ovarian cancer, pancreatic cancer, prostate cancer, or urothelial cancer). In other cases, the cancer characterized by an overexpression of CD46 is a metastatic cancer (e.g., a metastatic breast cancer, cervical cancer, colorectal cancer, kidney cancer, liver cancer, lung cancer, ovarian cancer, pancreatic cancer, prostate cancer, or urothelial cancer).

In some embodiments, a cancer characterized by an overexpression of CD46 comprises mesothelioma, a lymphoma, or a leukemia. In some instances, a cancer characterized by an overexpression of CD46 comprises mesothelioma. In some cases, a cancer characterized by an overexpression of CD46 comprises a lymphoma. In some cases, a cancer characterized by an overexpression of CD46 comprises a leukemia. In some cases, mesothelioma, a lymphoma, or a leukemia is a relapsed or refractory.

In some embodiments, a cancer characterized by an overexpression of CD46 is prostate cancer. In some embodiments, the prostate cancer is further classified into adenocarcinoma, a transition cell cancer, a squamous cell cancer, a small cell prostate cancer, a carcinoid, or a sarcoma.

In some embodiments, described herein is a method of treating a subject having prostate cancer, which comprises administering to the subject a pharmaceutical composition comprising a plurality of engineered effector cells, wherein each engineered effector cell comprises an engineered antigen binding domain that binds to an epitope of CD46, and wherein the engineered antigen binding domain is displayed on the surface of the engineered effector cell. In some instances, also described herein is a method of treating a subject having prostate cancer, which comprises administering to the subject a pharmaceutical composition comprising a plurality of chimeric antigen receptor (CAR) effector cells, wherein each CAR effector cell recognizes an epitope by an antibody of SEQ ID NOs: 1, 2, 9, 10, 17, 18, 25, 26, 33, 34, 41, 42, 49, 50, 57, 58, 65, 66, 73, 74, 81, 82, 89, 90, 97, 98, 105, 106, 113, 114, 121, 122, 129, 130, 137, 138, 145, 146, 153, 154, 161, 162, 169, 170, 177, 178, 185, 186, 193 or 194.

In some embodiments, a cancer characterized by an overexpression of CD46 is multiple myeloma. In some instances, multiple myeloma (MM) is further classified as smouldering (indolent) multiple myeloma (also known as asymptomatic myeloma), active (symptomatic) multiple myeloma, solitary plamacytoma of the bone, extramedullary plasmacytoma, light chain myeloma, non-secretory myeloma, immunoglobulin D (IgD) myeloma, or immunoglobulin E (IgE) myeloma. In some cases, multiple myeloma is characterized with a chromosomal aberration, e.g., such as an amplification of chromosome 1q. In some cases, multiple myeloma is characterized with a copy number gain at 1q21. In additional cases, the presence of 1q21 gain correlates with an overexpression of CD46 in multiple myeloma.

In some embodiments, described herein is a method of treating a subject having multiple myeloma, which comprises administering to the subject a pharmaceutical composition comprising a plurality of engineered effector cells, wherein each engineered effector cell comprises an engineered antigen binding domain that binds to an epitope of CD46, and wherein the engineered antigen binding domain is displayed on the surface of the engineered effector cell. In some instances, also described herein is a method of treating a subject having multiple myeloma, which comprises administering to the subject a pharmaceutical composition comprising a plurality of chimeric antigen receptor (CAR) effector cells, wherein each CAR effector cell recognizes an epitope by an antibody of SEQ ID NOs: 1, 2, 9, 10, 17, 18, 25, 26, 33, 34, 41, 42, 49, 50, 57, 58, 65, 66, 73, 74, 81, 82, 89, 90, 97, 98, 105, 106, 113, 114, 121, 122, 129, 130, 137, 138, 145, 146, 153, 154, 161, 162, 169, 170, 177, 178, 185, 186, 193 or 194.

In some embodiments, also described herein are methods of depleting CD46 overexpressed cells, which comprises a) contacting an effector cell ex vivo with a vector comprising a polynucleotide encoding an engineered antigen binding domain that recognizes an epitope of CD46 to generate a CD46-specific effector cell; and b) administering the CD46-specific effector cell to a subject having CD46 overexpressed cells, thereby depleting the population of CD46 overexpressed cells. In additional cases, described herein include methods of depleting CD46 overexpressed cells, which comprises a) contacting a T cell ex vivo with a vector comprising a polynucleotide encoding an engineered antigen binding domain that recognizes an epitope of CD46 to generate a CD46-specific CAR-T cell, wherein the engineered antigen binding domain is displayed on the surface of the CD46-specific CAR-T cell; and b) administering the CD46-specific CAR-T cell to a subject having CD46 overexpressed cells, thereby depleting the population of CD46 overexpressed cells.

In some cases, CD46 overexpressed cells are cancer cells. In some instances, cancer cells comprise breast cancer cells, cervical cancer cells, colorectal cancer cells, kidney cancer cells, liver cancer cells, lung cancer cells, ovarian cancer cells, pancreatic cancer cells, prostate cancer cells or urothelial cancer cells. In some cases, CD46 overexpressed cells comprise breast cancer cells, liver cancer cells, lung cancer cells, ovarian cancer cells, or prostate cancer cells. In some cases, CD46 overexpressed cells comprise breast cancer cells, ovarian cancer cells, or prostate cancer cells. In some cases, CD46 overexpressed cells comprise prostate cancer cells.

In some instances, CD46 overexpressed cells comprise cells from mesothelioma, cells from lymphoma, or cells from leukemia. In some instances, CD46 overexpressed cells comprise cells from mesothelioma. In some cases, CD46 overexpressed cells comprise cells from lymphoma. In some cases, CD46 overexpressed cells comprise cells from leukemia.

In some instances, CD46 overexpressed cells comprise cells from multiple myeloma.

In some embodiments, also described herein are methods of depleting prostate cancer cells, which comprises a) contacting an effector cell ex vivo with a vector comprising a polynucleotide encoding an engineered antigen binding domain that recognizes an epitope of CD46 to generate a CD46-specific effector cell; and b) administering the CD46-specific effector cell to a subject having prostate cancer, thereby depleting the population of prostate cancer cells. In additional cases, described herein include methods of depleting prostate cancer cells, which comprises a) contacting a T cell ex vivo with a vector comprising a polynucleotide encoding an engineered antigen binding domain that recognizes an epitope of CD46 to generate a CD46-specific CAR-T cell, wherein the engineered antigen binding domain is displayed on the surface of the CD46-specific CAR-T cell; and b) administering the CD46-specific CAR-T cell to a subject having prostate cancer, thereby depleting the population of prostate cancer cells.

In some embodiments, also described herein are methods of depleting cells from multiple myeloma, which comprises a) contacting an effector cell ex vivo with a vector comprising a polynucleotide encoding an engineered antigen binding domain that recognizes an epitope of CD46 to generate a CD46-specific effector cell; and b) administering the CD46-specific effector cell to a subject having multiple myeloma, thereby depleting the population of cells from multiple myeloma. In additional cases, described herein include methods of depleting cells from multiple myeloma, which comprises a) contacting a T cell ex vivo with a vector comprising a polynucleotide encoding an engineered antigen binding domain that recognizes an epitope of CD46 to generate a CD46-specific CAR-T cell, wherein the engineered antigen binding domain is displayed on the surface of the CD46-specific CAR-T cell; and b) administering the CD46-specific CAR-T cell to a subject having multiple myeloma, thereby depleting the population of cells from multiple myeloma.

Additional Therapeutic Agents

In some embodiments, one or more methods described herein further comprises administering an additional therapeutic agent. In some embodiments, the additional therapeutic agent comprises a cytokine. Cytokine is a category of small proteins between about 5-20 kDa that are involved in cell signaling. In some instances, cytokines include chemokines, interferons, interleukins, colony-stimulating factors or tumor necrosis factors. In some embodiments, chemokines play a role as a chemoattractant to guide the migration of cells, and is classified into four subfamilies: CXC, CC, CX3C, and XC. Exemplary chemokines include chemokines from the CC subfamily: CCL1, CCL2 (MCP-1), CCL3, CCL4, CCL5 (RANTES), CCL6, CCL7, CCL8, CCL9 (or CCL10), CCL11, CCL12, CCL13, CCL14, CCL15, CCL16, CCL17, CCL18, CCL19; CCL20, CCL21; CCL22, CCL23, CCL24, CCL25, CCL26, CCL27, and CCL28; the CXC subfamily: CXCL1, CXCL2, CXCL3, CXCL4, CXCL5, CXCL6, CXCL7, CXCL8, CXCL9, CXCL10, CXCL11, CXCL12; CXCL13, CXCL14, CXCL15, CXCL16, and CXCL17; the XC subfamily: XCL1 and XCL2; and the CX3C subfamily CX3CL1.

Interferons (IFNs) comprise interferon type I (e.g. IFN-α, IFN-β, IFN-ε, IFN-κ, and IFN-ω), interferon type II (e.g. IFN-γ), and interferon type III. In some embodiments, IFN-α is further classified into about 13 subtypes including IFNA1, IFNA2, IFNA5, IFNA6, IFNA7, IFNA8, IFNA10, IFNA13, IFNA14, IFNA16 IFNA17, and IFNA21.

Interleukins are expressed by leukocytes or white blood cells and they promote the development and differentiation of T and B lymphocytes and hematopoietic cells. Exemplary interleukins include IL-1, IL-2, IL-3, IL-4, IL-5, IL-6, IL-7, IL-8 (CXCL8). IL-9, IL-10, IL-11 IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, It-30, IL-31, IL-32, IL-33, IL-35, and IL-36.

Tumor necrosis factors (TNFs) are a group of cytokines that modulate apoptosis. In some instances, there are about 19 members within the TNF family, including, not limited to, TNFα, lymphotoxin-alpha. (LT-alpha), lymphotoxin-beta (LT-beta), T cell antigen gp39 (CD40L), CD27L, CD30L, FASL, 4-1BBL, OX40L, and TNF-related apoptosis inducing ligand (TRAIL).

Colony-stimulating factors (CSFs) are secreted glycoproteins that interact with receptor proteins on the surface of hemopoietic stem cells, which subsequently modulates cell proliferation and differentiation into specific kind of blood cells. In some instances, a CSF comprises macrophage colony-stimulating factor, granulocyte macrophage colony-stimulating factor (GM-CSF), granulocyte colony-stimulating factor (G-CSF) or promegapoietin.

In some embodiments, one or more methods described herein further comprises administration of a cytokine. In some instances, the cytokine comprises a chemokine, an interferon, an interleukin, a colony-stimulating factor or a tumor necrosis factor. In some cases, the cytokine comprises IL2, IL7, IL12, IL15, IL21, IFNγ, TNF-α, or a combination thereof.

In some embodiments, the additional therapeutic agent comprises a chemotherapeutic agent. In some embodiments, the chemotherapeutic agent is selected from among bortezomib, CAL-101, chlorambucil, cyclophosphamide, dexamethasone, docetaxel, doxorubicin, endostatin, everolimus, fludarabine, fostamatinib, ifosfamide, ibritumomab, lenalidomide, mesalazine, ofatumumab, paclitaxel, pentostatin, prednisone, rituximab, temsirolimus, thalidomide, tositumomab or a combination thereof.

In some embodiments, one or more methods described herein further comprises administration of a chemotherapeutic agent. In some cases, the chemotherapeutic agent is selected from among bortezomib, CAL-101, chlorambucil, cyclophosphamide, dexamethasone, docetaxel, doxorubicin, endostatin, everolimus, fludarabine, fostamatinib, ifosfamide, ibritumomab, lenalidomide, mesalazine, ofatumumab, paclitaxel, pentostatin, prednisone, rituximab, temsirolimus, thalidomide, tositumomab or a combination thereof. In some cases, the chemotherapeutic agent comprises cyclophosphamide and optionally with fludarabine.

In some embodiments, the engineered effector cell and the additional therapeutic agent are administered at the same time. In some embodiments, the engineered effector cell and the additional therapeutic agent are administered sequentially. In some embodiments, the engineered effector cell is administered after administering the additional therapeutic agent. In some embodiments, the engineered effector cell is administered before administering the additional therapeutic agent.

Vector Systems and Delivery Methods

In some embodiments, a vector comprises a polynucleotide encoding the engineered antigen binding domain, the stalk region, the transmembrane domain, the intracellular signaling domain, or a combination thereof. In some embodiments, the polynucleotide further comprises a promoter and a 3'untranslated region comprising a polyadenylation site (i.e. an expression cassette, as is shown in FIG. 1)

In some embodiments, any suitable vector system is used. In some embodiments, the vector system is a viral vector system. In some embodiments, the viral vector system is a retroviral vector, an adenovirus vector, a poxvirus vector, a herpesvirus vector, or an adeno-associated virus vector. In some embodiments, the retroviral vector is a gammaretrovirus vector or a lentivirus vector. In some embodiments, the vector system comprises a transcription factor, a nuclease, a transgene, or a combination thereof. In some embodiments, the vector system is a non-viral vector system. In some embodiments, the non-viral vector system is a plasmid vector, naked nucleic acid, or an mRNA. In some embodiments, the non-viral vector system is Sleeping Beauty (SB) Transposon System. In some embodiments, the naked nucleic acid is complexed with a delivery vehicle. In some embodiments, the delivery vehicle is a liposome or a poloxamer. In some embodiments, the naked nucleic acid is a DNA.

In some embodiments, methods of non-viral delivery of nucleic acids include electroporation, lipofection, nucleofection, gold nanoparticle delivery, microinjection, biolistics, virosomes, liposomes, immunoliposomes, polycation or lipid: nucleic acid conjugates, naked DNA, mRNA, artificial virions, and agent-enhanced uptake of DNA. In some embodiments, sonoporation using, e.g., the Sonitron 2000 system (Rich-Mar) is used for delivery of nucleic acids.

In some embodiments, the gene or portion of the gene is inserted using a restriction enzyme-based technique.

In some embodiments, vectors are delivered to cells ex vivo. In some embodiments, the cells are explanted from the subject. In some embodiments, the cells explanted from the subject comprises lymphocytes, T cells, bone marrow aspirates, or tissue biopsy. In some embodiments, cells are reimplanted into the subject, in which reimplanation of the cells into the subject occurs after selection for cells which have incorporated the vector. In some embodiments, prior to or after selection, the cells are expanded. In some embodiments, the vector further comprises a reporter gene so that the incorporation of the vector is detected via activation of the reporter gene. In some embodiments, any suitable reporter gene is used. In some embodiments, the reporter gene is a GFP, a resistance gene, a cell surface marker, or an endogenous tag. In some embodiments, suitable cells are selected using any suitable technology. In some embodiments, the technology to select suitable cells is flow cytometry or magnetic columns.

In some embodiments, the vector further encodes a suicide gene. In some embodiments, the suicide gene induces elimination of the engineered effector cell. In some embodiments, the suicide gene is any gene that induces apoptosis in the engineered effector cell. In some embodiments, the suicide gene encodes a factor able to convert a non-toxic prodrug into a toxic compound. In some embodiments, administration of the prodrug to the subject results in selective elimination of the engineered effector cell comprising the suicide gene.

Suitable Cells

In some embodiments, the engineered effector cells are derived from a source of cells. In some embodiments, the cells are autologous and the source is obtained from the subject. In other embodiments, the cells are allogenic. In some embodiments, the source of cells are obtained from PBMCs, bone marrow, lymph node tissue, cord blood, thymus tissue, tissue from a site of infection, ascites, pleural effusion, spleen tissue, tumors, or a combination thereof. In some embodiments, the source of cells are T cells or NK cells.

In certain embodiments, the source of cells is obtained from a unit of blood collected from the subject. In some embodiments, the blood is collected from the subject using any suitable technique, such as Ficoll™ separation. In some embodiments, cells from the circulating blood of the subject are obtained by apheresis. In some embodiments, the apheresis product contains lymphocytes, including T cells, monocytes, granulocytes, B cells, other nucleated white blood cells, red blood cells, and platelets. In some embodiments, the cells collected by apheresis are washed to remove the plasma fraction and to place the cells in an appropriate buffer or media for subsequent processing steps.

Pharmaceutical Composition and Formulation

In some embodiments, pharmaceutical compositions comprise a plurality of engineered effector cells described herein and a pharmaceutically acceptable carrier. In some embodiments, the pharmaceutically acceptable carrier is any suitable pharmaceutically acceptable carrier. The term "pharmaceutically acceptable carrier" as used herein means one or more compatible solid or liquid fillers, diluents, other excipients, or encapsulating substances which are suitable for administration into a human or veterinary patient (e.g., a physiologically acceptable carrier or a pharmacologically acceptable carrier). The term "carrier" denotes an organic or inorganic ingredient, natural or synthetic, with which the engineered effector cell is combined to facilitate the application. In some embodiments, the pharmaceutically acceptable carrier is co-mingled with one or more of the engineered effector cells and with each other, when more than one pharmaceutically acceptable carrier is present in the composition in a manner so as not to substantially impair the desired pharmaceutical efficacy.

"Pharmaceutically acceptable" materials typically are capable of administration to a subject without the production of significant undesirable physiological effects such as nausea, dizziness, rash, or gastric upset. It is, for example, desirable for a composition comprising a pharmaceutically acceptable carrier not to be immunogenic when administered to a human patient for therapeutic purposes.

In some embodiments, the pharmaceutical formulations include a carrier or carrier materials selected on the basis of compatibility with the composition disclosed herein, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. Pharmaceutically compatible carrier materials include, but are not limited to, acacia, gelatin, colloidal silicon dioxide, calcium glycerophosphate, calcium lactate, maltodextrin, glycerine, magnesium silicate, polyvinylpyrrollidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995), Hoover, John E., *Remington's Pharmaceutical Sciences*, Mack Publishing Co., Easton, Pennsylvania 1975, Liberman, H. A. and Lachman, L., Eds., *Pharmaceutical Dosage Forms*, Marcel Decker, New York, N.Y., 1980, and *Pharmaceutical Dosage Forms and Drug Delivery Systems*, Seventh Ed. (Lippincott Williams & Wilkins 1999).

In some instances, the pharmaceutical formulations further include pH adjusting agents or buffering agents which include acids such as acetic, boric, citric, lactic, phosphoric and hydrochloric acids, bases such as sodium hydroxide, sodium phosphate, sodium borate, sodium citrate, sodium acetate, sodium lactate and tris-hydroxymethylaminomethane, and buffers such as citrate/dextrose, sodium bicarbonate and ammonium chloride. Such acids, bases and buffers are included in an amount required to maintain pH of the composition in an acceptable range.

In some instances, the pharmaceutical formulation includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions, suitable salts include sodium chloride, potassium chloride, sodium thiosulfate, sodium bisulfite and ammonium sulfate.

In some embodiments, the pharmaceutical formulations include, but are not limited to, sugars like trehalose, sucrose, mannitol, maltose, glucose, or salts like potassium phosphate, sodium citrate, ammonium sulfate and/or other agents such as heparin to increase the solubility and in vivo stability of polypeptides.

In some instances, the pharmaceutical formulations further include diluent which are used to stabilize compounds because they can provide a more stable environment. Salts dissolved in buffered solutions (which also can provide pH control or maintenance) are utilized as diluents in the art, including, but not limited to a phosphate buffered saline solution.

In some cases, the pharmaceutical formulations include disintegration agents or disintegrants to facilitate the breakup or disintegration of a substance. The term "disintegrate" include both the dissolution and dispersion of the dosage form when contacted with gastrointestinal fluid. Examples of disintegration agents include a starch, e.g., a natural starch such as corn starch or potato starch, a pregelatinized starch such as National 1551 or Amijel®, or sodium starch glycolate such as Promogel® or Explotab®, a cellulose such as a wood product, methylcrystalline cellulose, e.g., Avicel®, Avicel® PH101, Avicer® PH102, Avicel® PH105, Elcema® P100, Emcocel®, Vivacel®, Ming Tia®, and Solka-Floc®, methylcellulose, croscarmellose, or a cross-linked cellulose, such as cross-linked sodium carboxymethylcellulose (Ac-Di-Sor), cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

Lubricants and glidants are also optionally included in the pharmaceutical formulations described herein for preventing, reducing or inhibiting adhesion or friction of materials. Exemplary lubricants include, e.g., stearic acid, calcium hydroxide, talc, sodium stearyl fumerate, a hydrocarbon such as mineral oil, or hydrogenated vegetable oil such as hydrogenated soybean oil)(Sterotex®, higher fatty acids and their alkali-metal and alkaline earth metal salts, such as aluminum, calcium, magnesium, zinc, stearic acid, sodium stearates, glycerol, talc, waxes, Stearowet®, boric acid, sodium benzoate, sodium acetate, sodium chloride, leucine, a polyethylene glycol (e.g., PEG-4000) or a methoxypolyethylene glycol such as Carbowax™, sodium oleate, sodium benzoate, glyceryl behenate, polyethylene glycol, magnesium or sodium lauryl sulfate, colloidal silica such as Syloid™, Cab-O-Sil®, a starch such as corn starch, silicone oil, a surfactant, and the like.

Solubilizers include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins, ethanol, n-butanol, isopropyl alcohol, cholesterol, bile salts, polyethylene glycol 200-600, glycofurol, transcutol, propylene glycol, and dimethyl isosorbide and the like.

Stabilizers include compounds such as any antioxidation agents, buffers, acids, preservatives and the like. Exemplary stabilizers include L-arginine hydrochloride, tromethamine, albumin (human), citric acid, benzyl alcohol, phenol, disodium biphosphate dehydrate, propylene glycol, metacresol or m-cresol, zinc acetate, polysorbate-20 or Tween® 20, or trometamol.

Suspending agents include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethyl cellulose, hydroxypropylmethylcellulose, hydroxyethyl cellulose, polysorbate-80, sodium alginate, polyethoxylated sorbitan monolaurate, polyethoxylated sorbitan monolaurate, povidone and the like.

Surfactants include compounds such as sodium lauryl sulfate, sodium docusate, Tween 60 or 80, triacetin, vitamin E TPGS, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like. Additional surfactants include polyoxyethylene fatty acid glycerides and vegetable oils, e.g., polyoxyethylene (60) hydrogenated castor oil, and polyoxyethylene alkylethers and alkylphenyl ethers, e.g., octoxynol 10, octoxynol 40. Sometimes, surfactants is included to enhance physical stability or for other purposes.

Viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

Wetting agents include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Dosage Forms

In some instances, a pharmaceutical composition described herein is formulated for parenteral administration. In some cases, parenteral administration comprises intravenous, subcutaneous, intramuscular, intra-arterial, intraosseous infusion, intracerebral, intracerebroventricular, or intrathecal administration. In some instances, a pharmaceutical composition described herein is formulated for intravenous, subcutaneous, intramuscular, intra-arterial, intraosseous infusion, intracerebral, intracerebroventricular, or intrathecal administration. In some cases, a pharmaceutical composition described herein is administered to a subject as an injection. In some cases, a pharmaceutical composition described herein is administered to a subject as an infusion.

In some instances, a pharmaceutical composition described herein is presented in any unit dosage form and is prepared by any suitable method, many of which are well known in the art of pharmacy. Such methods include the step of bringing the engineered effector cell into association with a carrier that constitutes one or more accessory ingredients.

In some embodiments, a composition suitable for parenteral administration comprises a sterile aqueous preparation of the inventive composition, which preferably is isotonic with the blood of the recipient. In some embodiments, the aqueous preparation is formulated according to known methods using suitable dispersing or wetting agents and suspending agents. In some embodiments the sterile injectable preparation is a sterile injectable solution or suspension in a non-toxic parenterally-acceptable diluent or solvent, for example, as a solution in 1,3-butane diol. In some embodiments, the vehicle or solvent is water, Ringer's solution, or isotonic sodium chloride solution. In some embodiments, sterile, fixed oils are conventionally employed as a solvent or suspending medium. In some embodiments, the oil is a synthetic mono- or di-glycerides. In some embodiments a fatty acids such as oleic acid is used in the preparation of injectables. In some embodiments, carrier formulations suitable for oral, subcutaneous, intravenous, intramuscular, etc. administrations are found in Remington's Pharmaceutical Sciences, Mack Publishing Co., Easton, PA.

Therapeutic Regimens

In some embodiments, one or more pharmaceutical compositions described herein are administered for therapeutic applications. In some embodiments, the pharmaceutical composition is administered once per day, twice per day, three times per day or more. The pharmaceutical composition is administered daily, every day, every alternate day, five days a week, once a week, every other week, two weeks per month, three weeks per month, once a month, twice a month, three times per month, or more. The pharmaceutical composition is administered for at least 1 month, 2 months, 3 months, 4 months, 5 months, 6 months, 7 months, 8 months, 9 months, 10 months, 11 months, 12 months, 18 months, 2 years, 3 years, or more.

In the case wherein the patient's status does improve, upon the doctor's discretion the administration of the composition is given continuously, alternatively, the dose of the composition being administered is temporarily reduced or temporarily suspended for a certain length of time (i.e., a "drug holiday"). In some instances, the length of the drug holiday varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday is from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. In some embodiments, the dosage or the frequency of administration, or both, is reduced, as a function of the symptoms, to a level at which the improved disease, disorder or condition is retained.

In some embodiments, the amount of a given agent that correspond to such an amount varies depending upon factors such as the particular compound, the severity of the disease, the identity (e.g., weight) of the subject or host in need of treatment, but nevertheless is routinely determined in a manner known in the art according to the particular circumstances surrounding the case, including, e.g., the specific agent being administered, the route of administration, and the subject or host being treated. In some instances, the desired dose is conveniently presented in a single dose or as divided doses administered simultaneously (or over a short period of time) or at appropriate intervals, for example as two, three, four or more sub-doses per day.

The foregoing ranges are merely suggestive, as the number of variables in regard to an individual treatment regime is large, and considerable excursions from these recommended values are not uncommon. Such dosages is altered depending on a number of variables, not limited to the activity of the compound used, the disease or condition to be treated, the mode of administration, the requirements of the subject, the severity of the disease or condition being treated, and the judgment of the practitioner.

In some embodiments, toxicity and therapeutic efficacy of such therapeutic regimens are determined by standard pharmaceutical procedures in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index and it is expressed as the ratio between LD50 and ED50. Compounds exhibiting high therapeutic indices are preferred. The data obtained from cell culture assays and animal studies are used in formulating a range of dosage for use in human. The dosage of such compounds lies preferably within a range of circulating concentrations that include the ED50 with minimal toxicity. The dosage varies within this range depending upon the dosage form employed and the route of administration utilized.

Kits/Article of Manufacture

Disclosed herein are kits and articles of manufacture suitable for carrying out the methods disclosed herein. In some embodiments, the kit comprises two or more components required for performing a therapeutic method described herein. In some embodiments, kit components include, but are not limited to, one or more engineered effector cells of the invention, appropriate reagents, and/or equipment. In some embodiments, the kit is packaged in a vial, pouch, ampoule, and/or any container suitable for a therapeutic method. Additional examples of pharmaceutical packaging materials include, but are not limited to, blister packs, bottles, tubes, bags, containers, bottles, and any packaging material suitable for a selected formulation and optionally intended mode of administration and treatment. In some embodiments, kit components are provided as concentrates (including lyophilized compositions), which are further diluted prior to use or provided at the concentration of use. In some embodiments, when the engineered effector cell is for use in vivo, a single dosage is provided in a sterilized container having the desired amount and concentration of the engineered effector cell.

In some cases, a kit includes labels listing contents and/or instructions for use, and package inserts with instructions for use. A set of instructions will also typically be included.

In some embodiments, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

Certain Terminologies

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviation, per the practice in the given value. Where particular values are described in the application and claims, unless otherwise stated the term "about" should be assumed to mean an acceptable error range for the particular value.

The terms "individual," "patient," or "subject" are used interchangeably. None of the terms require or are limited to situation characterized by the supervision (e.g. constant or intermittent) of a health care worker (e.g. a doctor, a registered nurse, a nurse practitioner, a physician's assistant, an orderly, or a hospice worker). Further, these terms refer to human or animal subjects. Animal subjects include, but are not limited to, animal models, such as, mammalian models of conditions or disorders associated with elevated CD46 expression such as breast cancer, cervical cancer, colorectal cancer, kidney cancer, liver cancer, lung cancer, multiple myeloma, ovarian cancer, pancreatic cancer, prostate cancer or urothelial cancer.

"Treating" or "treatment" of a state, disorder or condition (e.g., cancer) includes: (1) preventing or delaying the appearance of clinical or sub-clinical symptoms of the disorder developing in a human that is afflicted with or pre-disposed to the disorder but does not yet experience or display clinical or subclinical symptoms of the disorder; and/or (2) inhibiting the disorder, including arresting, reducing or delaying the clinical manifestation of the disorder or at least one clinical or sub-clinical symptom thereof; and/or (3) relieving the disorder, e.g., causing regression of the disorder or at least one of its clinical or sub-clinical symptoms; and/or (4) causing a decrease in the severity of one or more symptoms of the disorder. The benefit to a subject to be treated is either statistically significant or at least perceptible to the patient or to the physician.

The term "antibody" as used herein refers to immunoglobulin molecules and immunologically active portions of immunoglobulin molecules, i.e., molecules that contain an antigen binding site that immunospecifically binds an antigen. The term also refers to antibodies comprised of two immunoglobulin heavy chains and two immunoglobulin light chains as well as a variety of forms including full length antibodies and portions thereof; including, for example, an immunoglobulin molecule, a polyclonal antibody, a monoclonal antibody, a recombinant antibody, a chimeric antibody, a humanized antibody, a CDR-grafted antibody, F(ab)$_2$, Fv, scFv, IgGΔCH$_2$, F(ab')2, scFv2CH$_3$, F(ab), VL, VH, scFv4, scFv3, scFv2, dsFv, Fv, scFv-Fc, (scFv)2, a disulfide linked Fv, a single domain antibody (dAb), a diabody, a multispecific antibody, a dual specific antibody, an anti-idiotypic antibody, a bispecific antibody, any isotype (including, without limitation IgA, IgD, IgE, IgG, or IgM) a modified antibody, and a synthetic antibody (including, without limitation non-depleting IgG antibodies, T-bodies, or other Fc or Fab variants of antibodies). Each heavy chain is composed of a variable region of said heavy chain (abbreviated here as HCVR or VH) and a constant region of said heavy chain. Each light chain is composed of a variable region of said light chain (abbreviated here as LCVR or VL) and a constant region of said light chain. The VH and VL regions may be further divided into hypervariable regions referred to as complementarity-determining regions (CDRs) and interspersed with conserved regions referred to as framework regions (FR). Each VH and VL region thus consists of three CDRs and four FRs which are arranged from the N terminus to the C terminus in the following order: FR1, CDR1, FR2, CDR2, FR3, CDR3, FR4.

As used herein, the term "CDR" refers to the complementarity determining region within antibody variable sequences. There are three CDRs in each of the variable regions of the heavy chain and of the light chain, which are designated CDR1, CDR2 and CDR3, for each of the variable regions. The exact boundaries of these CDRs have been defined differently according to different systems, including those described by: Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), MacCallum et al., J. Mol. Biol. 262:732-745 (1996), "Antibody-antigen interactions: Contact analysis and binding site topography," J. Mol. Biol. 262, 732-745." ("Contact" numbering scheme), Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme), and Honegger A and Plückthun A, "Yet another numbering scheme for immunoglobulin variable domains: an automatic modeling and analysis tool," J Mol Biol, 2001 Jun. 8; 309(3):657-70, ("Aho" numbering scheme). The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The EU index or EU index as in Kabat or EU numbering scheme refers to the numbering of the EU antibody (Edelman et al., 1969, Proc Natl Acad Sci USA 63:78-85. In some embodiments, the methods used herein utilize CDRs defined according to any of these systems. In some embodiments, the methods used herein utilize CDRs defined according to the Kabat system.

As used herein, the term "engineered effector cell activation" or "engineered effector cell triggering" refers to the state of an engineered effector cell that has been sufficiently stimulated to induce detectable cellular proliferation, cytokine production and/or detectable effector function. Engineered effector cell activation can be measured using any suitable assay, such as an ELISA to measure cytokine secretion, an ELISPOT, flow cytometry assays to measure intracellular cytokine expression (CD107), flow cytometry assays to measure proliferation, and cytotoxicity assays (51Cr release assay) to determine target cell elimination. In some embodiments, these assays typically use controls (e.g. non-engineered cells) to compare to engineered effector cells (e.g. CAR-T) to determine relative activation of the engineered effector cell compared to a control. In some embodiments, these assays compare engineered effector cells incubated or put in contact with a target cell not expressing the target antigen.

As used herein, the term "affinity" refers to measures the strength of interaction between an epitope and an antibody's antigen binding site. Affinity is measured by the equilibrium dissociation constant ($K_D$). Lower values of $K_D$ indicate a higher affinity, and vice versa. In some embodiments, the antibody has affinity for CD46 of less than about $1.0 \times 10^{-6}$ M. In some embodiments, the dissociation constant is between about $1.0 \times 10^{-6}$ and $1.0 \times 10^{-7}$ M. In other embodiments, the dissociation constant is between about $1.0 \times 10^{-7}$ and $1.0 \times 10^{-8}$ M. In still other embodiments, the dissociation constant is between about $1.0 \times 10^{-8}$ and $1.0 \times 10^{-9}$ M. In yet other embodiments, the dissociation constant is less than $9.9 \times 10^{-10}$ M. In some embodiments, affinity is measured using art-known techniques, such as ELISA or BIACORE.

As used herein, the term "avidity" refers to measure of the overall strength of an antibody-antigen complex. In some embodiments, the antibody has avidity for CD46 of about 10 μM or less, 5 μM or less, 2 μM or less, 1 μM or less, 500 nM or less, 400 nM or less, 300 nM or less, or 200 nM or less. In some embodiments, the antibody has avidity for CD46 of about 100 nM or less, about 75 nM or less, about 50 nM or less, about 25 nM or less, about 10 nM or less, or about 5 nM or less. In some embodiments, the antibody has avidity for CD46 of about 1 nM or less, about 800 pM or less, about 700 pM or less, about 600 pM or less, about 500 pM or less, about 400 pM or less, about 300 pM or less, about 200 pM or less, or about 100 pM or less. In some embodiments, avidity is measured using art-known techniques, such as ELISA or BIACORE.

EXAMPLES

These examples are provided for illustrative purposes only and not to limit the scope of the claims provided herein.

Example 1: Illustrative CAR Configurations

VS5FL Fab sequence was converted into an scFv format and the resulting sequences were subsequently inserted into a second generation lentivirus CAR containing CD28 and CD3zeta (FIG. 1). High titer lentivirus stocks were used to transduce activated human T cells. CAR-T scFv expression was demonstrated by FACs and the resulting cells were used in T cell mediated cytotoxicity assays. Table 3 illustrates the nucleic acid sequence and polypeptide sequence of the YS5FL-scFV.

| YS5FL-scFV Sequences | SEQ ID NO: |
|---|---|
| GCTAGCCAGGTGCAGCTGGTGCAGTCTGGGGGAGGCGTGGTCCAGC CTGGGAGGTCCCTGAGACTCGCCTGTGCAGCCTCTGGACTCACCGT CAACAATTATGCTATGCACTGGGTCCGCCAGGCTCCAGGCAAGGGA CTGGAGTGGGTGGCAGTTATATCATATGATGGAAACAATAAATACT ATGCAGACTCCGTGAAGGGCCGATTCACCATCTCCAGAGACAATTC CAAGAACACGCTGTATCTGCAAATGAACAGCCTGAGAGCTGAGGA | 202 |

| YS5FL-scFV Sequences | SEQ ID NO: |
|---|---|
| CACGGCTGTGTATTACTGTGCGAAAGGGGGTGGATACTTCGATCTC TGGGGCCGTGGCACCCTGGTCACCGTCTCCTCAGGTGGAGGCGGTT CAGGCGGAGGTGGCTCTGGCGGTGGCGGATCGCAGTCTGTGTTGAC GCAGCCGCCCTCAGTGTCTGGGGCCCCAGGGCAGAGGGTCACCATC TCCTGCACTGGGAGCAGCTCCAACATCGGGGCAGGTTATGATGTAC ACTGGTACCAGCAGCTTCCAGGAACAGCCCCCAAACTCCTCATCTA TGGTAACAACAATCGGCCCTCAGGGGTCCCTGATCGATTCTCTGGC TCCAAGTCTGGCACCTCAGCCTCCCTGGCCATCACTGGGCTCCAGG CTGAGGATGAGGCTGATTATTACTGCAGCTCATATACAAGCGGCAC TTGGCTGTTCGGCGGGGGACCAAGCTGACCGTCCTACATCATCAC CATCACCATCTCGAG | |
| QVQLVQSGGGVVQPGRSLRLACAASGLTVNNYAMHWVRQAPGKGLE WVAVISYDGNNKYYADSVKGRFTISRDNSKNTLYLQMNSLRAEDTAV YYCAKGGGYFDLWGRGTLVTVSSGGGGSGGGGSGGGGSQSVLTQPPS VSGAPGQRVTISCTGSSSNIGAGYDVHWYQQLPGTAPKLLIYGNNNRP SGVPDRFSGSKSGTSASLAITGLQAEDEADYYCSSYTSGTWLFGGGTK LTVLHHHHHH | 203 |

Figure 2:
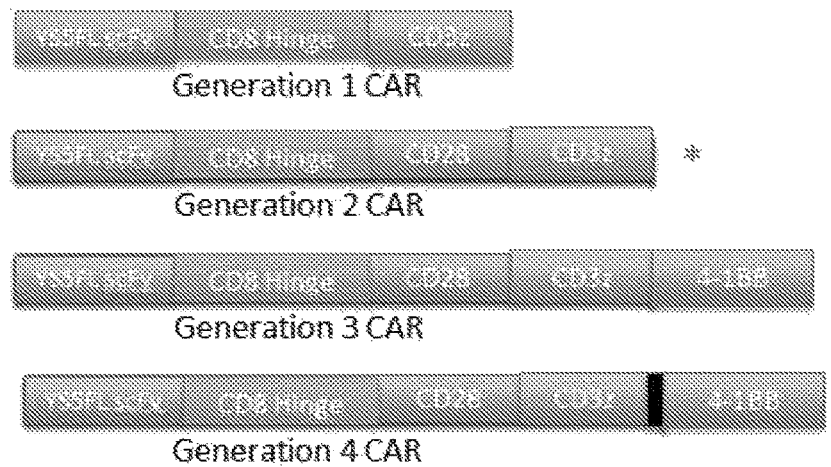
FIG. 2 illustrates exemplary configurations of a first, second, third, and fourth generation CAR.
Figure 3:
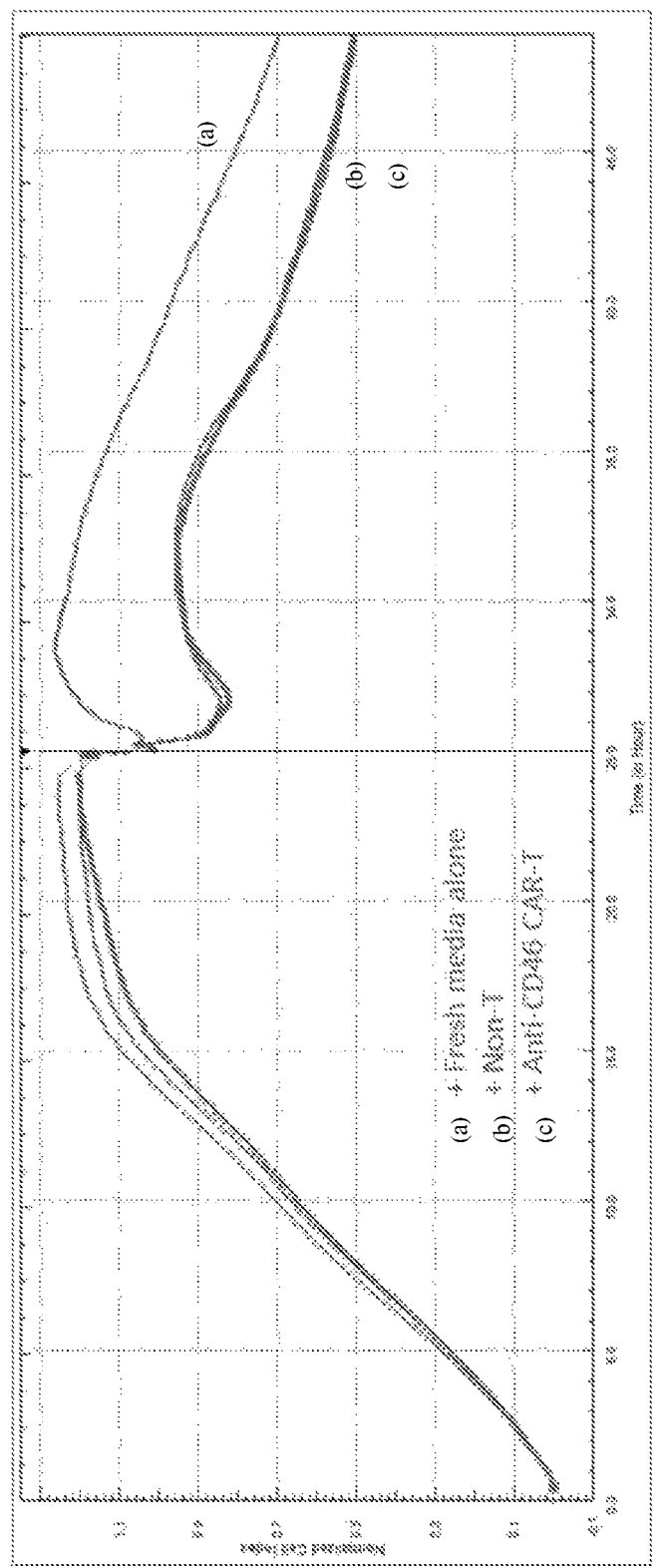
FIG. 3 illustrates impedance curves of BPH-1 cells, the vertical line at 25 hours indicating administration of the one of three treatments (fresh media alone, non-transduced T cells, or anti-CD46 CAR-T cells) to the BPH-1 cells.

FIG. 2 shows additional illustrative configurations of CD46-specific CARs. As shown in FIG. 2, a first generation CAR comprises a YS5FL scFv as the engineered antigen binding domain, a CD8 hinge, and a CD3zeta signaling domain. A second generation CAR comprises a YS5FL scFv as the engineered antigen binding domain, a CD8 hinge, a CD28 costimulatory domain, and a CD3zeta signaling domain. A third generation CAR comprises a YS5FL scFv as the engineered antigen binding domain, a CD8 hinge, a CD28 first costimulatory domain, a CD3zeta signaling domain, and a 4-1BB second costimulatory domain. A fourth generation CAR comprises a YS5FL scFv as the engineered antigen binding domain, a CD8 hinge, CD28 costimulatory domain, and a CD3zeta signaling domain, and further comprised a 4-1BB costimulatory ligand.

In some instances, use of two signaling domains (CD28 and CD3zeta) and the 4-1BB ligand provides therapeutic in vivo efficiency, showing balanced tumoricidal function (CD28), increased T cell persistence (4-1BB), and elevated CD8/CD4 ratio, and decreased exhaustion.

Example 2: Real Time Cytotoxicity Assay (RTCA) of Anti-CD46 CAR-T Cells

Effector cells were freshly activated and expanded on day 1. Viral transduction occurred on day 5 in CAR-T cells, but not in the non-transduced (Non-T) cells. On day 15, a real time cytotoxicity assay (RTCA) was performed. Target cells corresponding to each population of effector cells (Tables 4 and 5) were seeded at 10,000 cells/well at hour 0 of the RTCA. Effector cells were then added at the 25 hour mark of the RTCA. The effector cell: target cell ratio was 10:1. In some instances, during transduction, about 10% of the effector cells were transduced, yielding a ratio of transduced effector cell:target cell of 1:1. Data was collected by ACEA Biosciences software v2.0.

TABLE 4

| Experimental group | | |
|---|---|---|
| | Effector cells | Target cells |
| True | Anti-CD46 CAR-T | LNCAP-C4-B2 |
| Null | Non-T | BPH-1 |

TABLE 5

| | Control group | |
|---|---|---|
| | Effector cells | Target cells |
| True | Anti-CD19 CAR-T | CD-19 HeLa |
| Null | Non-T | HeLa |

Real Time Cell Analysis (RTCA) Assay

Electrical impedance was recorded every 5 minutes to provide a normalized Cell Index (CI) (FIGS. 3-6). Results were grouped by the target cell, with each cell line having a characteristic impedance curve over 82 hours. At 25 hours, the target cells were given one of the following: 1) fresh media alone; 2) fresh media plus non-transduced T cells; or 3) fresh media plus transduced T cells. In some instances, the additional of non-T cells initially lowered the Cell Index, but the cells continued to grow and after a period of time reach to a level relative to cells from the "Fresh media alone group."

Figure 4:
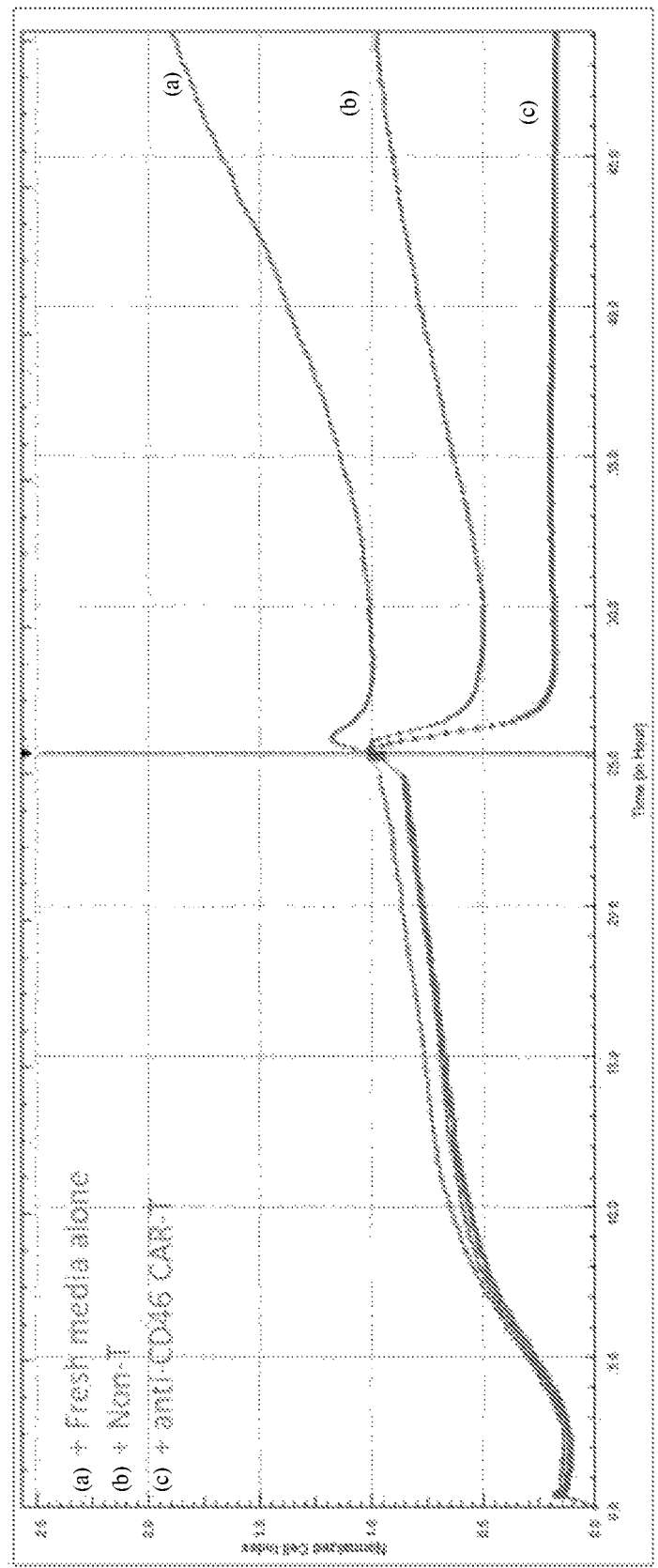
FIG. 4 illustrates impedance curves of LNCAP-C4-B2 cells, the vertical line at 25 hours indicating administration of the one of three treatments (fresh media alone, non-transduced T cells, or anti-CD46 CAR-T cells) to the LNCAP-C4-B2 cells.
Figure 5:
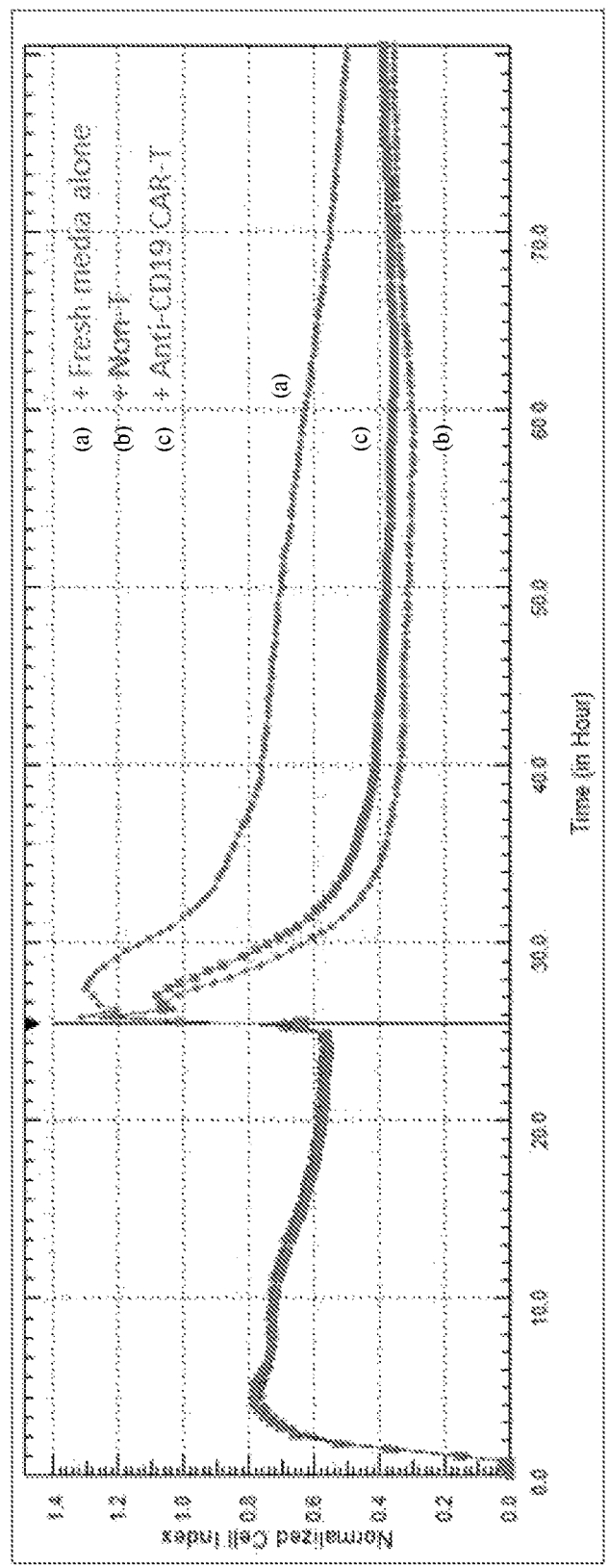
FIG. 5 illustrates impedance curves of HeLa cells, the vertical line at 25 hours indicating administration of the one of three treatments (fresh media alone, non-transduced T cells, or anti-CD19 CAR-T cells) to the HeLa cells.
Figure 6:
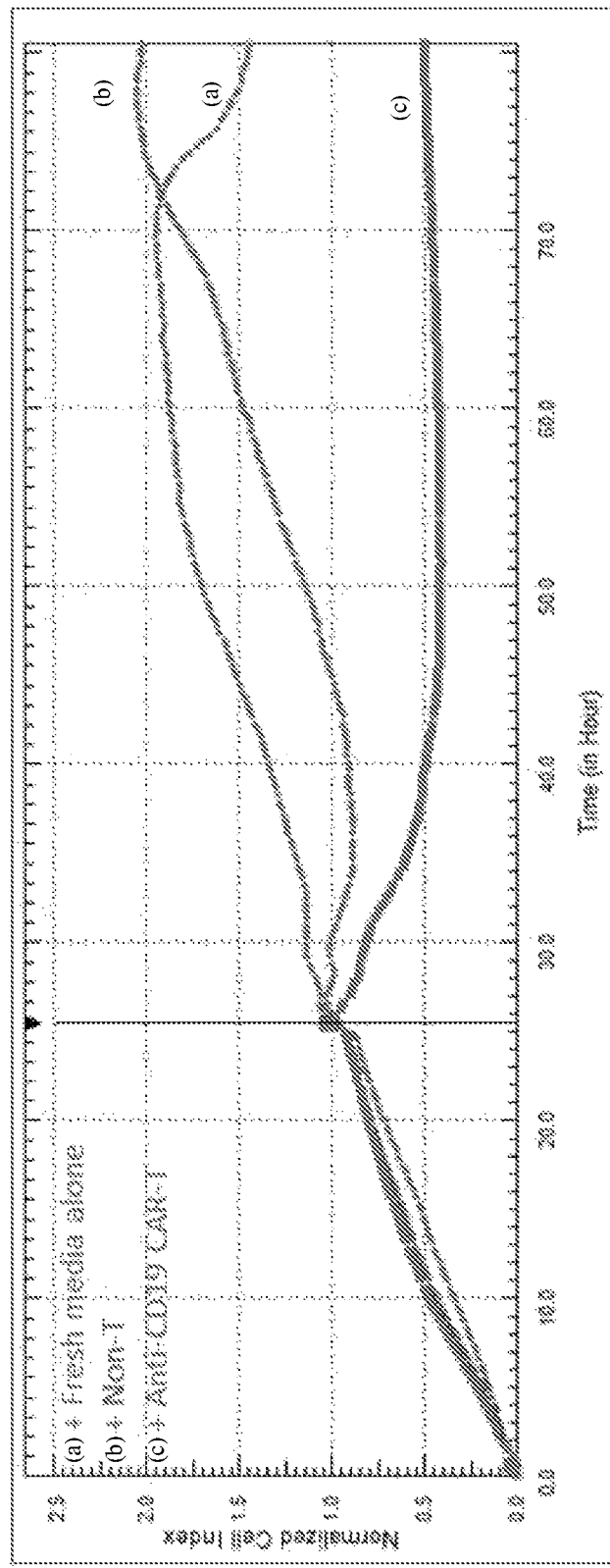
FIG. 6 illustrates impedance curves of CD19 HeLa cells, the vertical line at 25 hours indicating administration of the one of three treatments (fresh media alone, non-transduced T cells, or anti-CD19 CAR-T cells) to the CD19 HeLa cells.

The effect of anti-CD46 CARs was compared to anti-CD19 CARs for both control non-target cells (FIGS. 3 and 5, respectively) and target cells (FIGS. 4 and 6, respectively). The control non-target cells (BPH-1) for the anti-CD46 CAR-T cells responded similarly to transduced and non-transduced T cells (FIG. 3) LNCAP-C4-B2 were the target cells for the anti-CD46 CAR-T cells. These CARs showed a killing rate of over 99% of LNCAP-C4-B2 cells within the first 2 hours following administration of the anti-CD46CARs at the 25 hour mark (FIG. 4). This is compared to the anti-CD19 CARs, which showed a drop in target cell growth after approximately 10 hours following administration of the anti-CD19 CARs at the 25 hour mark (FIG. 5).

Example 3: In Vitro Cytotoxicity of CAR-T Cells

A number of different CAR-T expression vectors were generated and subsequently transduced into human T cells. The resulting CAR-T cells were analyzed for surface CD46 expression and compared for their ability to kill various prostate cancer cells in vitro. Various published reports have shown that different vectors have varying degrees of potency in vivo, but minimal effects in vitro.

FIG. 7 illustrates six exemplary lentivirus-based CAR-T constructs. The lentivirus vectors illustrate Generations 2, 3, and 4 CARs.

FIG. 8A-FIG. 8G show FACS analysis of CAR expression on T cells on the day of in vitro cytotoxicity assay. As illustrated in the figure, >85% CAR(BB) (or CARBB) expressions are observed for EGFP and Puro constructs while only 25-32% of CAR(BB) expression is detected for 4-1BBL constructs.

FIG. 9A-FIG. 9D show in vitro cytotoxicity assay on prostate cancer cell lines using six different variants of CAR-T cells targeted to CD46. Single time point cell viability measurements were done 24 hr after adding CAR-T (T-cells) A CytoTox 96 Non-Radioactive Cytotoxicity Assay (Promega) was used.

As illustrated in FIG. 9A-FIG. 9D, effector-to-target (E-T) ratio of 10:1 is effective at killing most prostate cancer cells, relative to the negative control cell line BPH which has minimum expression of CD46. In addition, T cells transduced with the second generation CAR is superior in cell kill effect relative to the remaining third and fourth generation CARs in vitro.

Example 4: In Vitro CAR-T Studies On PC-3 Cell Lines

Figure 10:
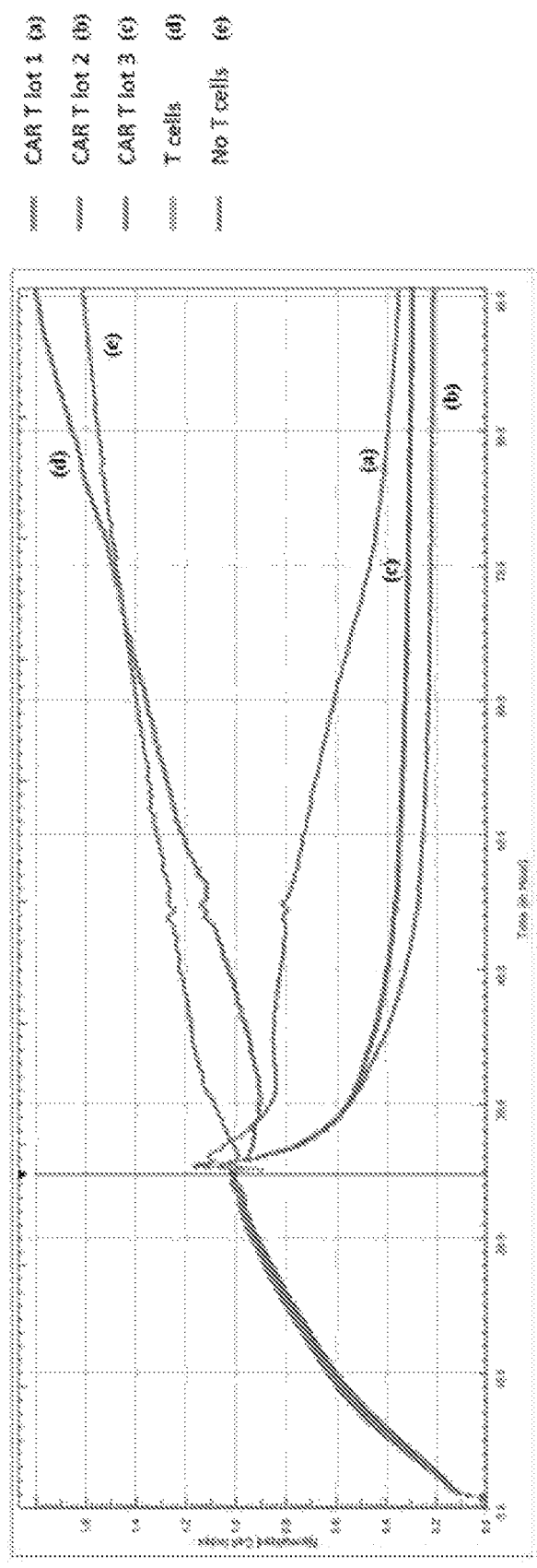
FIG. 10 illustrates 3 different lots of CAR-T cells compared with non-transduced T cells for their ability to kill PC-3 prostate cancer cells.

Prior to initiating in vivo xenograft studies at MiBio research (CRO), the MiBio PC-3 cell line was tested in vitro. Human T cells were transduced with Generation 3 lentivirus vector expressing a CD46 chimeric antigen receptor. 3 lots of transduced T cells were generated for anti-proliferation studies. To determine which lots, if any, were capable of killing PC-3 prostate cancer cells, a 10:1 effector (CAR-T)/tumor cell (PC-3) (T/C) was used (FIG. 10). Real Time Cell Analysis (RTCA) was used to measure viable cells. RTCA uses an electrical current that passes through the tumor cell monolayer. As cells die, the impedance id decreased and this is observed in the FIG. 10 and FIG. 11.

In FIG. 10, 3 different lots of CAR-T cells were compared with non-transduced T cells for their ability to kill PC-3 prostate cancer cells. Although all 3 lots effectively killed PC-3 cells, lots 2 and 3 appeared to be far more potent, severely reducing the number of tumor cells relative to untreated or non-transduced T cells. Lot 2 was selected for subsequent in vivo studies.

Figure 11:
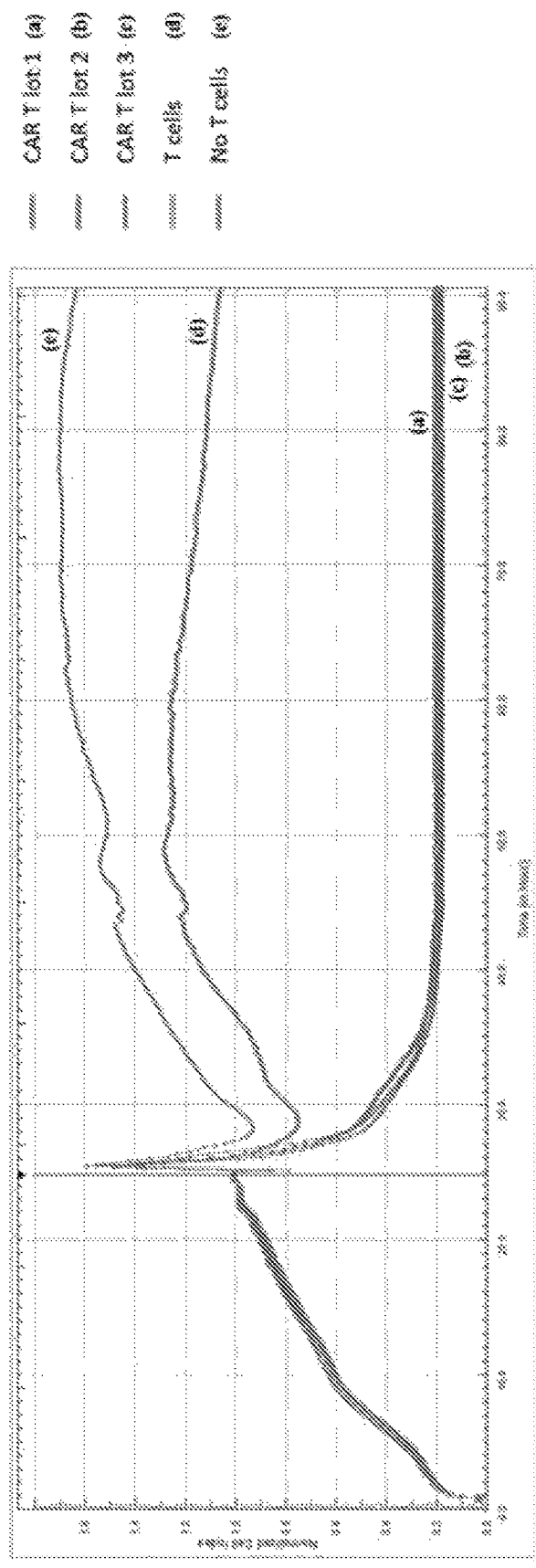
FIG. 11 illustrates MiBio PC-3 cells compared to a PC-3 luc cell line.

In FIG. 11, MiBio PC-3 cells were compared to a PC-3 luc cell line obtained from UCSF. PC-3 luc appears to be far more sensitive to killing by all three lots of CAR-T cells. Cells transfected with the firefly luciferase gene historically are more sensitive to anti-tumor agents.

Example 5: In Vitro Cytotoxicity of CAR-T Cells on MM.1S-Luc (MiBio Cell Line)

Figure 12:
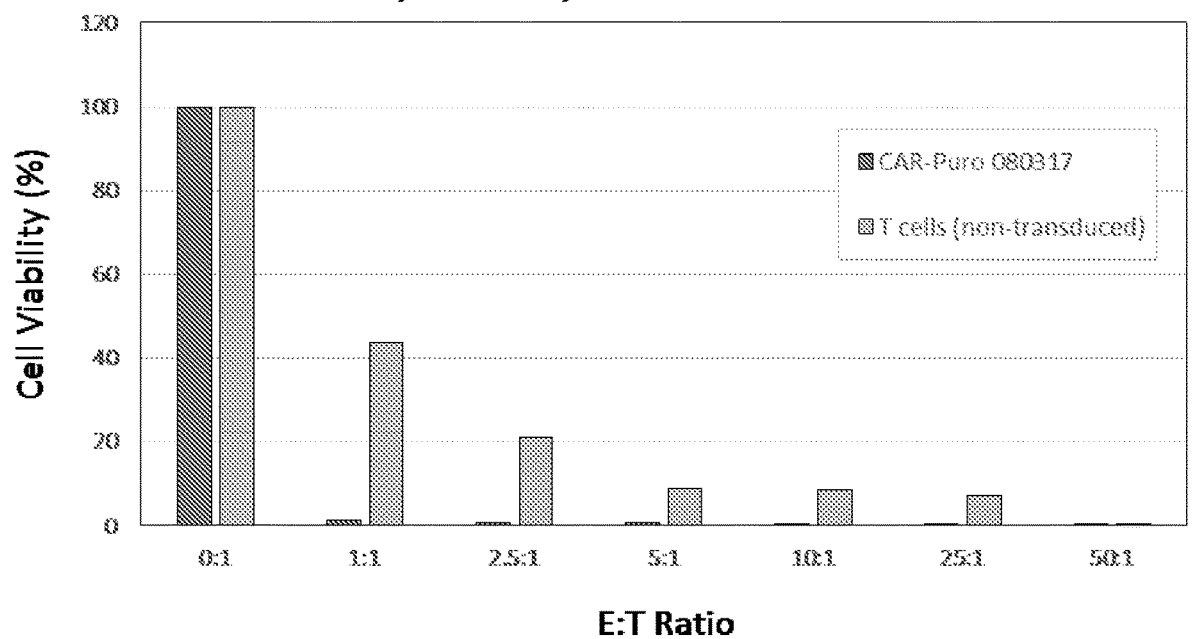
FIG. 12 illustrates the in vitro cytotoxicity of CAR T cells on MM.1S-luc.

Cell viability was measured 24 hr after co-culture using luciferin based assays. Table 6 illustrates the E-T ratio of two exemplary CAR constructs. FIG. 12 illustrates the in vitro cytotoxicity of CART cells on MM.1S-luc.

TABLE 6

| | Cell Viability (%) | |
|---|---|---|
| E:T ratio | CAR-Puro 080317 | T cells (non-transduced) |
| 0:1 | 100 | 100 |
| 1:1 | 1.4 | 44 |
| 2.5:1 | 0.76 | 21 |
| 5:1 | 0.56 | 8.7 |
| 10:1 | 0.37 | 8.4 |
| 25:1 | 0.31 | 7.2 |
| 50:1 | 0.45 | 0.47 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An engineered effector cell that specifically binds CD46, comprising:
an antibody that binds to an epitope of CD46,
wherein the antibody is displayed on the surface of the engineered effector cell,
wherein the antibody comprises:
  a heavy chain variable region comprising three complementarity determining regions (CDRs), and
  a light chain variable region comprising three CDRs;
i) wherein the heavy chain variable region comprises:
  a variable heavy (VH) CDR1 that has an amino acid sequence of SEQ ID NO: 3,
  a VH CDR2 that has an amino acid sequence of SEQ ID NO: 4, and
  a VH CDR3 that has an amino acid sequence of SEQ ID NO: 5; and
  wherein the light chain variable region comprises:
  a variable light (VL) CDR1 that has an amino acid sequence of SEQ ID NO: 6,
  a VL CDR2 that has an amino acid sequence of SEQ ID NO: 7, and
  a VL CDR3 that has an amino acid sequence of SEQ ID NO: 8; or
ii) wherein the heavy chain variable region comprises:
  a VH CDR1 that has an amino acid sequence of SEQ ID NO: 11,
  a VH CDR2 that has an amino acid sequence of SEQ ID NO: 12, and
  a VH CDR3 that has an amino acid sequence of SEQ ID NO: 13; and
  wherein the light chain variable region comprises:
  a VL CDR1 that has an amino acid sequence of SEQ ID NO: 14.
  a VL CDR2 that has an amino acid sequence of SEQ ID NO: 15, and
  a VL CDR3 that has an amino acid sequence of SEQ ID NO: 16; or
iii) wherein the heavy chain variable region comprises:
  a VH CDR1 that has an amino acid sequence of SEQ ID NO: 179,
  a VH CDR2 that has an amino acid sequence of SEQ ID NO: 180, and
  a VH CDR3 that has an amino acid sequence of SEQ ID NO: 181; and
  wherein the light chain variable region comprises:
  a VL CDR1 that has an amino acid sequence of SEQ ID NO: 182.
  a VL CDR2 that has an amino acid sequence of SEQ ID NO: 183, and
  a VL CDR3 that has an amino acid sequence of SEQ ID NO: 184.

2. The engineered effector cell of claim 1, wherein the engineered effector cell is an engineered T cell, optionally an engineered natural killer T cell; or an engineered natural killer cell.

3. The engineered effector cell of claim 1, wherein the antibody comprises an Fab, Fab', F(ab')$_2$, scFv, sc(Fv)$_2$, dsFv, diabody or binding fragments thereof.

4. The engineered effector cell of claim 1, wherein the antibody comprises an scFv.

5. The engineered effector cell of claim 1, wherein the antibody comprises:
   a) a heavy chain variable region having at least 90% sequence identity to SEQ ID NO: 1 and a light chain variable region having at least 90% sequence identity to SEQ ID NO: 2; or
   b) a heavy chain variable region having at least 90% sequence identity to SEQ ID NO: 9 and a light chain variable region having at least 90% sequence identity to SEQ ID NO: 10; or
   c) a heavy chain variable region having at least 90% sequence identity to SEQ ID NO: 177 and a light chain variable region having at least 90% sequence identity to SEQ ID NO: 178.

6. The engineered effector cell of claim 1, wherein the antibody further comprises a stalk region, a transmembrane domain, at least one costimulatory domain, and a signaling domain.

7. The engineered effector cell of claim 6, wherein the at least one costimulatory signaling domain comprises:
   a. CD8, CD27, CD28z, 4-1BB, ICOS, OX40, or a fragment or combination thereof;
   b. CD28 and 4-1BB or fragments thereof; or
   c. CD28 or fragment thereof.

8. The engineered effector cell of claim 6, wherein a first costimulatory signaling domain is encoded by a first vector and a second costimulatory signaling domain is encoded by a second vector.

9. The engineered effector cell of claim 6, wherein the signaling domain is derived from a CD3δ chain.

10. The engineered effector cell of claim 6, wherein a single polypeptide comprises the stalk region, the transmembrane domain, the at least one costimulatory domain, and the signaling domain.

11. The engineered effector cell of claim 10, wherein the single polypeptide comprises two costimulatory domains.

12. The engineered effector cell of claim 1, wherein the engineered effector cell is prepared from an autologous effector cell or an allogeneic effector cell.

13. The engineered effector cell of claim 1, wherein the engineered effector cell is a CAR-T cell or a CAR-NK cell.

14. A pharmaceutical composition comprising an engineered effector cell of claim 1; and an excipient.

15. The engineered effector cell of claim 1, wherein the cell comprises a cytokine transgene.

16. A method of treating a subject having a cancer characterized by an overexpression of CD46, comprising:
   administering to the subject a pharmaceutical composition comprising a plurality of the engineered effector cell of claim 1.

17. The method of claim 16, wherein the antibody of the engineered effector cell further comprises a stalk region, a transmembrane domain, at least one costimulatory domain, and a signaling domain.

18. The method of claim 17, wherein the at least one costimulatory signaling domain comprises:
   CD8, CD27, CD28z, 4-1BB, ICOS, OX40, or fragment or combination thereof;
   CD28 and 4-1BB or fragments thereof; or
   CD28 or fragment thereof.

19. A method of depleting CD46 overexpressed cells, comprising:
   a) contacting an effector cell ex vivo with a vector comprising a polynucleotide encoding an antibody that recognizes an epitope of CD46 to generate a CD46-specific effector cell, wherein the antibody is displayed on the surface of the CD46-specific effector cell; and
   b) administering the CD46-specific effector cell to a subject having CD46 overexpressed cells, thereby depleting the population of CD46 overexpressed cells, wherein the antibody comprises:
   a heavy chain variable region comprising three complementarity determining regions (CDRs), and
   a light chain variable region comprising three CDRs;
   i) wherein the heavy chain variable region comprises:
      a variable heavy (VH) CDR1 that has an amino acid sequence of SEQ ID NO: 3,
      a VH CDR2 that has an amino acid sequence of SEQ ID NO: 4, and
      a VH CDR3 that has an amino acid sequence of SEQ ID NO: 5; and
   wherein the light chain variable region comprises:
      a variable light (VL) CDR1 that has an amino acid sequence of SEQ ID NO: 6,
      a VL CDR2 that has an amino acid sequence of SEQ ID NO: 7, and
      a VL CDR3 that has an amino acid sequence of SEQ ID NO: 8; or
   ii) wherein the heavy chain variable region comprises:
      a VH CDR1 that has an amino acid sequence of SEQ ID NO: 11,
      a VH CDR2 that has an amino acid sequence of SEQ ID NO: 12, and
      a VH CDR3 that has an amino acid sequence of SEQ ID NO: 13; and
   wherein the light chain variable region comprises:
      a VL CDR 1 that has an amino acid sequence of SEQ ID NO: 14,
      a VL CDR2 that has an amino acid sequence of SEQ ID NO: 15, and
      a VL CDR3 that has an amino acid sequence of SEQ ID NO: 16; or
   iii) wherein the heavy chain variable region comprises:
      a VH CDR1 that has an amino acid sequence of SEQ ID NO: 179,
      a VH CDR2 that has an amino acid sequence of SEQ ID NO: 180, and
      a VH CDR3 that has an amino acid sequence of SEQ ID NO: 181; and
   wherein the light chain variable region comprises:
      a VL CDR 1 that has an amino acid sequence of SEQ ID NO: 182,
      a VL CDR2 that has an amino acid sequence of SEQ ID NO: 183, and
      a VL CDR3 that has an amino acid sequence of SEQ ID NO: 184.

* * * * *